United States Patent
Vishnudas et al.

(10) Patent No.: US 11,091,447 B2
(45) Date of Patent: Aug. 17, 2021

(54) UBE2K MODULATORS AND METHODS FOR THEIR USE

(71) Applicant: Berg LLC, Framingham, MA (US)

(72) Inventors: Vivek K. Vishnudas, Bedford, MA (US); Dinesh U. Chimmanamada, Arlington, MA (US); Santosh A. Khedkar, Lexington, MA (US)

(73) Assignee: Berg LLC, Framingham, MA (US)

( * ) Notice: Subject to any disclaimer, the term of this patent is extended or adjusted under 35 U.S.C. 154(b) by 0 days.

(21) Appl. No.: 17/139,188

(22) Filed: Dec. 31, 2020

(65) Prior Publication Data

US 2021/0214320 A1    Jul. 15, 2021

Related U.S. Application Data

(60) Provisional application No. 62/956,802, filed on Jan. 3, 2020.

(51) Int. Cl.
*C07D 249/08* (2006.01)
*C07D 405/12* (2006.01)

(52) U.S. Cl.
CPC .......... *C07D 249/08* (2013.01); *C07D 405/12* (2013.01)

(58) Field of Classification Search
CPC ........................ C07D 249/08; C07D 405/12
See application file for complete search history.

(56) References Cited

U.S. PATENT DOCUMENTS

| | | |
|---|---|---|
| 5,624,941 A | 4/1997 | Barth et al. |
| 5,656,606 A | 8/1997 | Nargund et al. |
| 6,300,456 B1 | 10/2001 | Musa |
| 6,495,677 B1 | 12/2002 | Ramasamy et al. |
| 6,521,610 B2 | 2/2003 | Tiebes et al. |
| 6,759,427 B2 | 7/2004 | Fick et al. |
| 6,815,542 B2 | 11/2004 | Hong et al. |
| 6,979,686 B1 | 12/2005 | Naraian et al. |
| 6,982,269 B2 | 1/2006 | Glasky et al. |
| 7,122,547 B1 | 10/2006 | Huth et al. |
| 7,169,797 B2 | 1/2007 | Xin et al. |
| 7,211,671 B2 | 5/2007 | Sheppeck et al. |
| 7,241,785 B2 | 7/2007 | Momose et al. |
| 7,319,108 B2 | 1/2008 | Schwink et al. |
| 7,531,670 B2 | 5/2009 | Glasky et al. |
| 7,781,471 B2 | 8/2010 | Barth et al. |
| 7,829,724 B2 | 11/2010 | Perrissoud et al. |
| 8,063,233 B2 | 11/2011 | Glasky et al. |
| 8,088,797 B2 | 1/2012 | Barth et al. |
| 8,299,104 B2 | 10/2012 | Schwink et al. |
| 8,329,708 B2 | 12/2012 | Sim et al. |
| 8,377,456 B2 | 2/2013 | Glasky et al. |
| 8,648,089 B2 | 2/2014 | Sim et al. |
| 8,710,089 B2 | 4/2014 | Perrissoud et al. |
| 8,734,818 B2 | 5/2014 | Glasky et al. |
| 8,791,139 B2 | 7/2014 | Fischer et al. |
| 8,889,732 B2 | 11/2014 | Shigeta et al. |
| 9,181,229 B2 | 11/2015 | Ono et al. |
| 9,382,236 B2 | 7/2016 | Ushioda et al. |
| 9,550,749 B2 | 1/2017 | Kita et al. |
| 9,920,017 B2 | 3/2018 | Heilmann et al. |
| 9,969,700 B2 | 5/2018 | Ushioda et al. |
| 10,017,490 B2 | 7/2018 | Kita et al. |
| 2002/0013326 A1 | 1/2002 | Tiebes et al. |
| 2002/0198218 A1 | 12/2002 | Fick et al. |
| 2003/0022892 A1 | 1/2003 | Glasky et al. |
| 2003/0162812 A1 | 8/2003 | Harmsen et al. |
| 2004/0002596 A1 | 1/2004 | Hong et al. |
| 2004/0063775 A1 | 4/2004 | Momose et al. |
| 2004/0082563 A1 | 4/2004 | Dorsch et al. |
| 2004/0138269 A1 | 7/2004 | Sun et al. |
| 2004/0167188 A1 | 8/2004 | Xin et al. |
| 2004/0214870 A1 | 10/2004 | Xin et al. |
| 2005/0075384 A1 | 4/2005 | Sheppeck et al. |
| 2005/0096317 A1 | 5/2005 | Glasky et al. |
| 2005/0176710 A1 | 8/2005 | Schwink et al. |
| 2007/0037857 A1 | 2/2007 | Perrissoud et al. |
| 2007/0208061 A2 | 9/2007 | Perrissoud et al. |
| 2008/0051578 A1 | 2/2008 | Dahmann et al. |
| 2008/0207707 A1 | 8/2008 | Schwink et al. |
| 2008/0293794 A1 | 11/2008 | Barth et al. |
| 2009/0156825 A1 | 6/2009 | Heidebrecht, Jr. et al. |
| 2009/0192319 A1 | 7/2009 | Glasky et al. |
| 2010/0041709 A1 | 2/2010 | Barth et al. |
| 2010/0144818 A1 | 6/2010 | Barth et al. |
| 2010/0331343 A1 | 12/2010 | Perrissoud et al. |
| 2011/0046370 A1 | 2/2011 | Sim et al. |
| 2011/0152236 A1 | 6/2011 | Bernardelli et al. |
| 2012/0015980 A1 | 1/2012 | Fischer et al. |
| 2012/0053180 A1 | 3/2012 | Kang et al. |
| 2012/0070385 A1 | 3/2012 | Glasky et al. |
| 2012/0209005 A1 | 8/2012 | Shigeta et al. |
| 2013/0079343 A1 | 3/2013 | Sim et al. |
| 2013/0225648 A1 | 8/2013 | Glasky et al. |
| 2013/0345419 A1 | 12/2013 | Ono et al. |
| 2014/0357858 A1 | 12/2014 | Ushioda et al. |
| 2015/0259322 A1 | 9/2015 | Kita et al. |

(Continued)

FOREIGN PATENT DOCUMENTS

| | | |
|---|---|---|
| AR | 57450 | 12/2007 |
| CA | 2973891 A1 | 1/2018 |

(Continued)

*Primary Examiner* — Robert H Havlin
(74) *Attorney, Agent, or Firm* — McCarter & English, LLP; Jill Mello; Michael J. DeGrazia

(57) ABSTRACT

Provided are compounds of Formula (I):

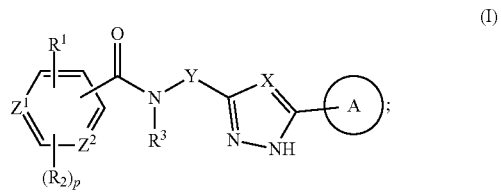

and pharmaceutically acceptable salts and compositions thereof, which are useful for treating conditions associated with modulation of UBE2K.

8 Claims, 4 Drawing Sheets

(56) References Cited

U.S. PATENT DOCUMENTS

| | | |
|---|---|---|
| 2016/0280667 A1 | 9/2016 | Ushioda et al. |
| 2017/0014395 A1 | 1/2017 | Kita et al. |
| 2017/0073318 A1 | 3/2017 | Heilmann et al. |
| 2018/0072708 A1 | 3/2018 | Yanagisawa et al. |
| 2018/0201587 A1 | 7/2018 | Ushioda et al. |

FOREIGN PATENT DOCUMENTS

| | | |
|---|---|---|
| CN | 1072211 A | 5/1993 |
| CN | 1188764 A | 7/1998 |
| CN | 104876912 A | 9/2015 |
| CN | 106831747 A | 6/2017 |
| CN | 108117518 A | 6/2018 |
| EP | 74229 A1 | 3/1983 |
| EP | 576357 A1 | 12/1993 |
| EP | 1568368 A1 | 8/2005 |
| JP | 62006248 A | 1/1987 |
| JP | 62133447 A | 6/1998 |
| JP | 2000256358 A | 9/2000 |
| JP | 2000297086 A | 10/2000 |
| JP | 2006151832 A | 6/2006 |
| JP | 2006182668 A | 7/2006 |
| JP | 2007045752 A | 2/2007 |
| JP | 2007126400 A | 5/2007 |
| JP | 2009040702 A | 2/2009 |
| WO | 8909212 A1 | 10/1989 |
| WO | 9608486 A1 | 3/1996 |
| WO | 9736886 A1 | 10/1997 |
| WO | 1998/00401 A1 | 1/1998 |
| WO | 9815345 A1 | 4/1998 |
| WO | 9816523 A2 | 4/1998 |
| WO | 9816524 A1 | 4/1998 |
| WO | 9816525 A1 | 4/1998 |
| WO | 9816547 A1 | 4/1998 |
| WO | 9828269 A1 | 7/1998 |
| WO | 9829119 A1 | 7/1998 |
| WO | 1998/52940 A1 | 11/1998 |
| WO | 9857937 A2 | 12/1998 |
| WO | 2000031063 A1 | 6/2000 |
| WO | 2000039108 A1 | 7/2000 |
| WO | 2000064888 A1 | 11/2000 |
| WO | 2001068663 A1 | 9/2001 |
| WO | 2002000651 A2 | 1/2002 |
| WO | 2002080928 A1 | 10/2002 |
| WO | 2002085856 A1 | 10/2002 |
| WO | 2002085904 A1 | 10/2002 |
| WO | 2003099793 A1 | 12/2003 |
| WO | 2004032846 A2 | 4/2004 |
| WO | 2004033632 A2 | 4/2004 |
| WO | 2004039795 A2 | 5/2004 |
| WO | 2004078746 A2 | 9/2004 |
| WO | 2004087653 A2 | 10/2004 |
| WO | 2004089303 A2 | 10/2004 |
| WO | 2005000309 A2 | 1/2005 |
| WO | 2005035551 A2 | 4/2005 |
| WO | 2005/044797 A1 | 5/2005 |
| WO | 2005044201 A2 | 5/2005 |
| WO | 2005082089 A2 | 9/2005 |
| WO | 2005110994 A2 | 11/2005 |
| WO | 2006/046024 A1 | 5/2006 |
| WO | 2006048771 A1 | 5/2006 |
| WO | 2006055503 A2 | 5/2006 |
| WO | 2006055553 A2 | 5/2006 |
| WO | 2006064277 A1 | 6/2006 |
| WO | 2006/074984 A1 | 7/2006 |
| WO | 2006108792 A1 | 10/2006 |
| WO | 2006123257 A2 | 11/2006 |
| WO | 2006124731 A2 | 11/2006 |
| WO | 2007/002559 A1 | 1/2007 |
| WO | 2007008895 A1 | 1/2007 |
| WO | 2007017125 A1 | 2/2007 |
| WO | 2007020013 A2 | 2/2007 |
| WO | 2007/030567 A2 | 3/2007 |
| WO | 2007025940 A1 | 3/2007 |
| WO | 2007/070514 A1 | 6/2007 |
| WO | 2007091396 A1 | 8/2007 |
| WO | 2007123953 A2 | 11/2007 |
| WO | 2008002490 A2 | 1/2008 |
| WO | 2008011557 A2 | 1/2008 |
| WO | 2008022013 A1 | 2/2008 |
| WO | 2008045668 A1 | 4/2008 |
| WO | 2008057681 A2 | 5/2008 |
| WO | 2008059207 A1 | 5/2008 |
| WO | 2008063609 A2 | 5/2008 |
| WO | 2008063912 A1 | 5/2008 |
| WO | 2008073459 A1 | 6/2008 |
| WO | 2008073670 A2 | 6/2008 |
| WO | 2008075013 A1 | 6/2008 |
| WO | 2008096005 A1 | 8/2008 |
| WO | 2008098977 A1 | 8/2008 |
| WO | 2008124651 A2 | 10/2008 |
| WO | 2008145616 A1 | 12/2008 |
| WO | 2009032277 A1 | 3/2009 |
| WO | 2009042294 A2 | 4/2009 |
| WO | 2009074782 A1 | 6/2009 |
| WO | 2009077766 A1 | 6/2009 |
| WO | 2009099670 A2 | 8/2009 |
| WO | 2009108766 A1 | 9/2009 |
| WO | 2009111502 A2 | 9/2009 |
| WO | 2009137081 A2 | 11/2009 |
| WO | 2009140517 A1 | 11/2009 |
| WO | 2009143018 A2 | 11/2009 |
| WO | 2010001365 A1 | 1/2010 |
| WO | 2010056585 A2 | 5/2010 |
| WO | 2010/075376 A2 | 7/2010 |
| WO | 2010075197 A1 | 7/2010 |
| WO | 2011041462 A2 | 4/2011 |
| WO | 2011042797 A1 | 4/2011 |
| WO | 2011061469 A1 | 5/2011 |
| WO | 2011/072275 A2 | 6/2011 |
| WO | 2011075613 A1 | 6/2011 |
| WO | 2011099832 A2 | 8/2011 |
| WO | 2011137022 A1 | 11/2011 |
| WO | 2011143129 A1 | 11/2011 |
| WO | 2011157748 A1 | 12/2011 |
| WO | 2012042433 A1 | 4/2012 |
| WO | 2012050868 A1 | 4/2012 |
| WO | 2012051117 A2 | 4/2012 |
| WO | 2012058531 A2 | 5/2012 |
| WO | 2012068234 A2 | 5/2012 |
| WO | 2012092471 A2 | 7/2012 |
| WO | 2012/129562 A2 | 9/2012 |
| WO | 2012120135 A1 | 9/2012 |
| WO | 2012149236 A1 | 11/2012 |
| WO | 2012154608 A1 | 11/2012 |
| WO | 2013/010880 A1 | 1/2013 |
| WO | 2013/010881 A1 | 1/2013 |
| WO | 2013066835 A2 | 5/2013 |
| WO | 2013092674 A1 | 6/2013 |
| WO | 2013155338 A2 | 10/2013 |
| WO | 2013161308 A1 | 10/2013 |
| WO | 2014033044 A1 | 3/2014 |
| WO | 2014044916 A1 | 3/2014 |
| WO | 2014071031 A1 | 5/2014 |
| WO | 2014/108679 A1 | 7/2014 |
| WO | 2014144017 A2 | 9/2014 |
| WO | 2014170677 A1 | 10/2014 |
| WO | 2014173904 A1 | 10/2014 |
| WO | 2015022546 A1 | 2/2015 |
| WO | 2015048316 A1 | 4/2015 |
| WO | 2015/067791 A1 | 5/2015 |
| WO | 2015/101957 A2 | 7/2015 |
| WO | 2015101958 A2 | 7/2015 |
| WO | 2016008010 A1 | 1/2016 |
| WO | 2016030310 A1 | 3/2016 |
| WO | 2016/057322 A1 | 4/2016 |
| WO | 2016153023 A1 | 9/2016 |
| WO | 2017040451 A1 | 3/2017 |
| WO | 2017096045 A1 | 6/2017 |
| WO | 2017106367 A1 | 6/2017 |
| WO | 2017122209 A2 | 7/2017 |
| WO | 2017142821 A1 | 8/2017 |
| WO | 2017147102 A1 | 8/2017 |
| WO | 2017/161028 A1 | 9/2017 |

(56) References Cited

FOREIGN PATENT DOCUMENTS

| | | |
|---|---|---|
| WO | 2017152117 A1 | 9/2017 |
| WO | 2017152126 A1 | 9/2017 |
| WO | 2017210685 A1 | 12/2017 |
| WO | 2018011090 A1 | 1/2018 |
| WO | 2018053267 A1 | 3/2018 |
| WO | 2018062978 A1 | 4/2018 |
| WO | 2018068295 A1 | 4/2018 |
| WO | 2018068297 A1 | 4/2018 |
| WO | 2018071313 A1 | 4/2018 |
| WO | 2018071317 A1 | 4/2018 |
| WO | 2018098206 A1 | 5/2018 |
| WO | 2018117034 A1 | 6/2018 |
| WO | 2018/127130 A1 | 7/2018 |
| WO | 2018132372 A1 | 7/2018 |
| WO | 2018138354 A1 | 8/2018 |
| WO | 2018138359 A1 | 8/2018 |
| WO | 2018207847 A1 | 11/2018 |
| WO | 2018212534 A1 | 11/2018 |
| WO | 2019013562 A1 | 1/2019 |
| WO | 2019071073 A1 | 4/2019 |
| WO | 2019091277 A1 | 5/2019 |
| WO | WO2020094363 * 5/2020 ........... C07D 403/04 |

* cited by examiner

UBE2K MODULATORS AND METHODS FOR THEIR USE

RELATED APPLICATIONS

This application claims the benefit of priority to U.S. Provisional Application No. 62/956,802, filed Jan. 3, 2020, the entire contents of which are incorporated herein by reference.

BACKGROUND

Cancer progression is a global concern with the later stage of metastasis accounting for the second leading cause of death throughout the world. Because of its role in cellular proliferation and survival, the ubiquitin-proteasome system (UPS) has recently gained attention as an important target for cancer therapy. Ubiquitin (Ub) is a small, highly conserved regulatory protein that is covalently tagged to proteins as a signal for proteasome degradation. Ubiquitination is a multi-step process that transfers Ub to specific target proteins. Ub conjugation occurs through an enzymatic cascade that involves Ub-activating (E1), Ub-conjugating (E2), and Ub-ligating (E3) enzymes. See e.g., Cancer Biol Ther. 2010 Oct. 15; 10(8): 737-747. As the addition and removal of Ub is a fundamental process in all eukaryotic cells, it is not surprising that Ub metabolism enzymes feature prominently as either oncogenes or tumor suppressors in a variety of cancers and many signaling/regulatory pathways relevant to cancer. See Cell Cycle 2017; 16(7): 634-648.

While progress has been made in this field (e.g., as in the FDA approved proteasome inhibitor bortezomib), there remains a need for improved small molecule modulators of UPS.

SUMMARY

Provided herein are compounds having the Formula I:

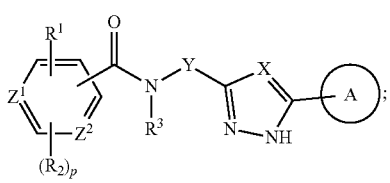

and pharmaceutically acceptable salts and compositions thereof, wherein $R^1$, $R^2$, p, $Z^1$, $Z^2$, X, ring A, and p are as described herein. The disclosed compounds and compositions modulate (e.g., inhibit) UBE2K and modified forms of UBE2K namely but not limited to mono ubiquitinated UBE2K, di, tri and tetra ubiquitinated UBE2K and are useful in treating various cancers.

DETAILED DESCRIPTION

1. General Description of Compounds

Figure 1:
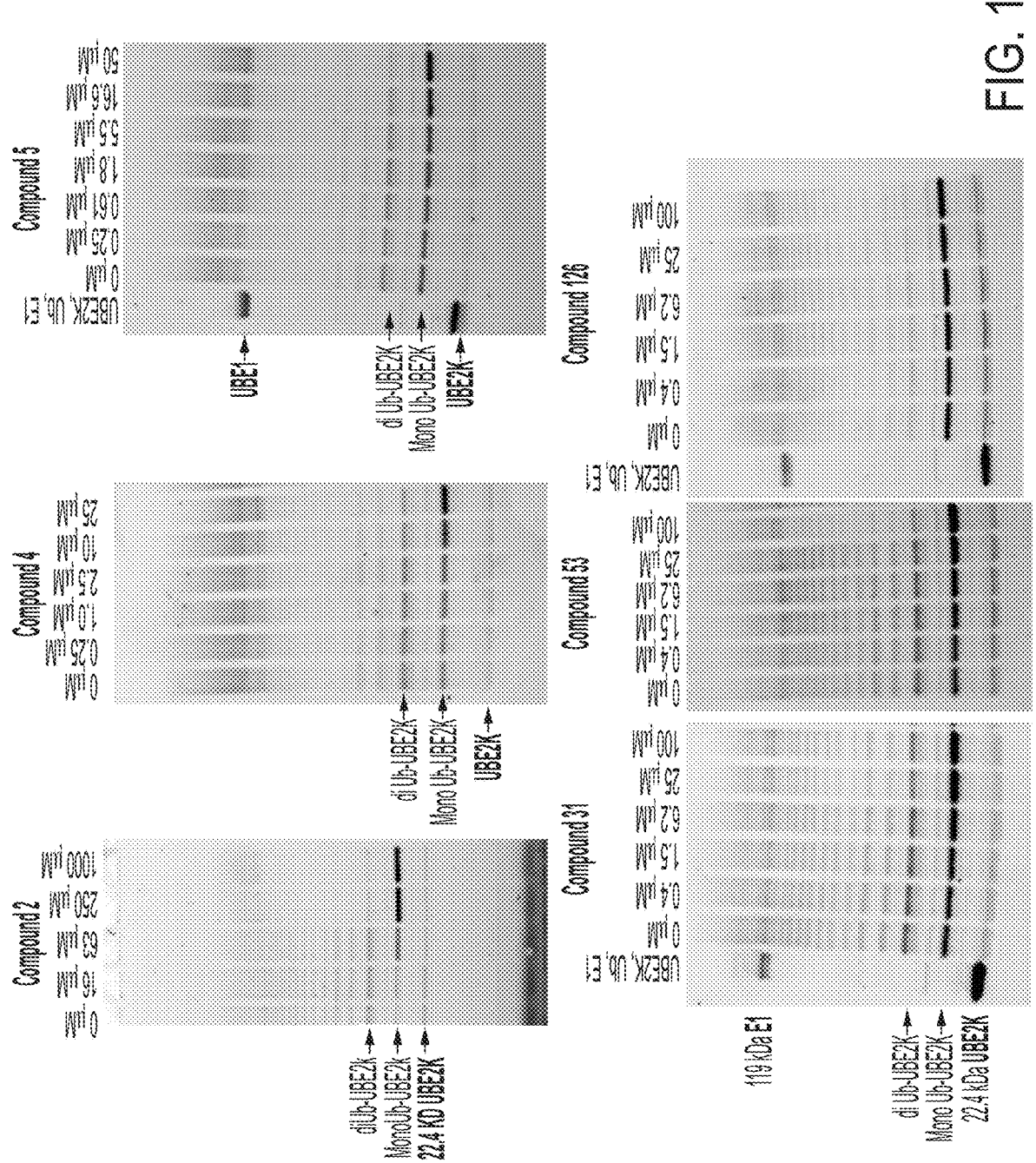
FIG. 1 illustrates UBE2K poly ubiqutination activity by certain inventive compounds.

Provided herein is a compound of Formula I

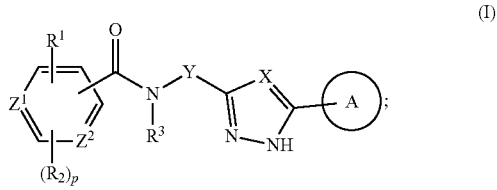

$Z^1$ and $Z^2$ are each independently N or CH;

X is N or CH;

ring A is phenyl or a 5- to 9-membered heteroaryl, each of which are optionally substituted with 1 to 3 groups selected from $R^5$;

Y is $CH_2$, —$CHR^a$, —$CR^aR^b$, or SO;

$R^a$ and $R^b$ are each independently halo, $(C_1-C_6)$alkyl, or halo$(C_1-C_6)$alkyl; or $R^a$ and $R^b$ together with the carbon atom they are bound for a 3- to 6-membered cycloalkyl or a 3- to 6-membered heterocyclyl, each of which are optionally substituted with 1 to 3 groups selected from halo, $(C_1-C_6)$alkyl, halo$(C_1-C_6)$alkyl, $(C_1-C_6)$alkoxy, halo$(C_1-C_6)$alkoxy, $(C_1-C_6)$alkylOH, $(C_1-C_6)$alkylO$(C_1-C_6)$alkyl, and OH;

$R^1$ is halo$(C_1-C_6)$alkyl, halo$(C_1-C_6)$alkoxy, or —$NR^cR^d$, wherein two available hydrogen atoms on said halo$(C_1-C_6)$alkyl and halo$(C_1-C_6)$alkoxy may be taken together to which the carbon atoms they are attached to form a 3- to 6-membered cycloalkyl optionally substituted with 1 to 3 groups selected from halo, $(C_1-C_6)$alkyl, halo$(C_1-C_6)$alkyl, $(C_1-C_6)$alkoxy, and halo$(C_1-C_6)$alkoxy;

$R^c$ and $R^d$ are each independently hydrogen $(C_1-C_6)$alkyl, halo$(C_1-C_6)$alkyl, $(C_1-C_6)$alkylO$(C_1-C_6)$alkyl, halo$(C_1-C_6)$alkylO$(C_1-C_6)$alkyl, $(C_1-C_6)$alkyl-O-halo$(C_1-C_6)$alkyl, halo$(C_1-C_6)$alkyl-O-halo$(C_1-C_6)$alkyl, or $(C_1-C_6)$alkylOH; or $R^c$ and $R^d$ together with the nitrogen atom they are bound form a 4- to 7-membered heterocyclyl optionally substituted with 1 to 3 groups selected from halo, $(C_1-C_6)$alkyl, halo$(C_1-C_6)$alkyl, $(C_1-C_6)$alkoxy, halo$(C_1-C_6)$alkoxy, and oxo;

$R^2$ is CN, halo, OH, $(C_1-C_6)$alkyl, halo$(C_1-C_6)$alkyl, $(C_1-C_6)$alkoxy, or halo$(C_1-C_6)$alkoxy; or $R^1$ and $R^2$, when on adjacent carbon atoms, are taken together with the carbon atoms to which they are attached to form a 5- or 6-membered oxygen containing heterocyclyl optionally substituted with 1 to 3 groups selected from halo, $(C_1-C_6)$alkyl, and halo$(C_1-C_6)$alkyl;

$R^3$ is hydrogen, $(C_1-C_6)$alkyl, or halo$(C_1-C_6)$alkyl;

$R^4$ is CN, halo, OH, $(C_1-C_6)$alkyl, halo$(C_1-C_6)$alkyl, $(C_1-C_6)$alkoxy, halo$(C_1-C_6)$alkoxy, —NH$(C_1-C_6)$alkyl, —N[$(C_1-C_6)$alkyl]2, or a 5- to 6-membered heterocyclyl; and p is 0 or 1

2. Definitions

When used in connection to describe a chemical group that may have multiple points of attachment, a hyphen (-)

designates the point of attachment of that group to the variable to which is defined. For example, —NH($C_1$-$C_6$) alkyl means that the point of attachment for this group is on the nitrogen atom.

The terms "halo" and "halogen" refer to an atom selected from fluorine (fluoro, —F), chlorine (chloro, —Cl), bromine (bromo, —Br), and iodine (iodo, -I).

The term "alkyl" when used alone or as part of a larger moiety, such as "haloalkyl", means saturated straight-chain or branched monovalent hydrocarbon radical. Unless otherwise specified, an alkyl group typically has 1-4 carbon atoms, i.e., ($C_1$-$C_4$)alkyl.

"Alkoxy" means an alkyl radical attached through an oxygen linking atom, represented by —O-alkyl. For example, "($C_1$-$C_4$)alkoxy" includes methoxy, ethoxy, proproxy, and butoxy.

substitutable position and, include, e.g., the position at which the heterocyclyl is attached.

The term "cycloalkyl" refers to a monocyclic hydrocarbon of the specified size (e.g., 3-, 4-, 5-, 6-, or 7-membered ring). Cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. When specified, optional substituents on a cycloalkyl group may be present on any substitutable position and, include, e.g., the position at which the cycloalkyl is attached.

The disclosed compounds exist in various tautomeric forms and are part of the present disclosure. The term "tautomers" or "tautomeric" refers to two or more interconvertible compounds/substituents resulting from at least one formal migration of a hydrogen atom and at least one change in valency. Exemplary tautomerizations include e.g., the following:

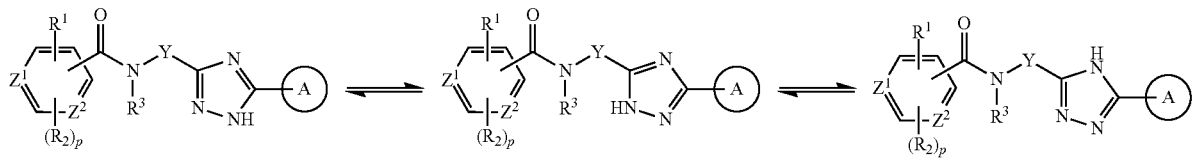

The term "haloalkyl" includes mono, poly, and perhaloalkyl groups where the halogens are independently selected from fluorine, chlorine, bromine, and iodine.

"Haloalkoxy" is a haloalkyl group which is attached to another moiety via an oxygen atom such as, e.g., but are not limited to —OCHCF$_2$ or —OCF$_3$.

"Oxo" refers to the divalent function group =O, i.e., an oxygen atom connected to another atom (typically carbon or sulfur) by a double bond.

The term "heteroaryl" refers to an aromatic ring of the specified size (e.g., 5-, 6-, 7-, 8-, or 9-membered ring) containing 1 to 4 heteroatoms independently selected from N, O, and S. A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, etc. Bi-cyclic heteroaryl include groups in which a mono-cyclic heteroaryl ring is fused to one or more aryl or heteroaryl rings. Nonlimiting examples include indolyl, imidazopyridinyl, benzooxazolyl, benzooxodiazolyl, indazolyl, benzimidazolyl, benzthiazolyl, pyrazolopyridinyl, thienopyridinyl, thienopyrimidinyl, indolizinyl, etc. When specified, optional substituents on a heteroaryl group may be present on any substitutable position.

The term "heterocyclyl" refers to a saturated or partially unsaturated monocyclic ring of the specified size (e.g., 3-, 4-, 5-, 6-, or 7-membered ring) containing 1 to 4 heteroatoms independently selected from N, O, and S. A heterocyclyl ring can be attached to its pendant group at any heteroatom or carbon atom that results in a stable structure. Examples of such saturated or partially unsaturated heterocyclic radicals include, without limitation, oxiranyl, thiiranyl, aziridinyl, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. When specified, optional substituents on a heterocyclyl group may be present on any All such isomeric forms of such compounds are expressly included. Thus, when a compound herein is represented by a structural formula or designated by a chemical name herein, all other tautomeric forms which may exist for the compound are encompassed by the structural formula. This includes compounds of the Formula I where X is N or C.

The compounds described herein may be present in the form of pharmaceutically acceptable salts. For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable w" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "effective amount" or "therapeutically effective amount" refers to an amount of a compound described herein that will elicit a biological or medical response of a subject e.g., a dosage of between 0.01-100 mg/kg body weight/day.

3. Compounds

In a first embodiment, provided herein is a compound of Formula I:

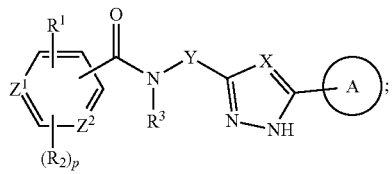

(I)

or a pharmaceutically acceptable salt thereof, wherein the variables are as described above.

In a second embodiment, the compound of Formula I is of the Formula II or III:

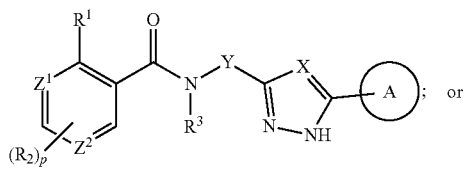

(II)

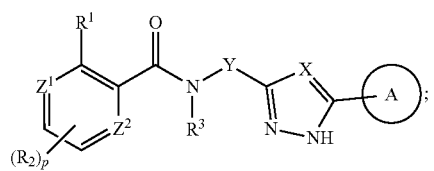

(III)

or a pharmaceutically acceptable salt thereof, wherein the remaining variables are as described above for Formula I.

In a third embodiment, the compound of Formula I is of the Formula IV:

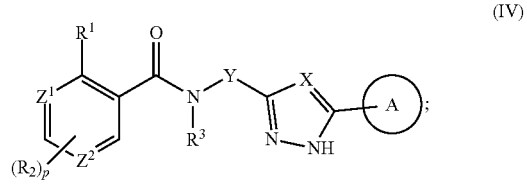

(IV)

or a pharmaceutically acceptable salt thereof, wherein the remaining variables are as described above for Formula I.

In a fourth embodiment, $R^3$ in the compound of Formula I, II, III, or IV, or a pharmaceutically acceptable salt thereof, is hydrogen, wherein the remaining variables are as described for Formula I or the second embodiment.

In a fifth embodiment, Y in the compound of Formula I, II, III, or IV, or a pharmaceutically acceptable salt thereof, is $CH_2$, $SO_2$, or cyclopropyl, wherein the remaining variables are as described for Formula I or the fourth embodiment. Alternatively, as part of a fifth Y in the compound of Formula I, II, III, or IV, or a pharmaceutically acceptable salt thereof, is $CH_2$, wherein the remaining variables are as described for Formula I or the fourth embodiment.

In a sixth embodiment, $Z^1$ is N and $Z^2$ is CH; $Z^1$ is CH and $Z^2$ is N; or $Z^1$ and $Z^2$ are each CH in the compound of Formula I, II, III, or IV, or a pharmaceutically acceptable salt thereof, wherein the remaining variables are as described for Formula I or the fourth or fifth embodiment. Alternatively, as part of a sixth embodiment, $Z^1$ and $Z^2$ are each CH in the compound of Formula I, II, III, or IV, or a pharmaceutically acceptable salt thereof, wherein the remaining variables are as described for Formula I or the fourth or fifth embodiment.

In a seventh embodiment, ring A in the compound of Formula I, II, III, or IV, or a pharmaceutically acceptable salt thereof, is phenyl or a 5- to 6-membered heteroaryl, each of which are optionally substituted with 1 to 3 groups selected from $R^5$, wherein the remaining variables are as described for Formula I or the fourth, fifth, or sixth embodiment. Alternatively, as part of a seventh embodiment, ring A in the compound of Formula I, II, III, or IV, or a pharmaceutically acceptable salt thereof, is phenyl, pyridyl, furanyl, or pyrazolyl, each of which are optionally substituted with 1 to 3 groups selected from $R^5$, wherein the remaining variables are as described for Formula I or the fourth, fifth, or sixth embodiment. In another alternative, as part of a seventh embodiment, ring A in the compound of Formula I, II, III, or IV, or a pharmaceutically acceptable salt thereof, is phenyl or furanyl, each of which are optionally substituted with 1 to 3 groups selected from $R^5$, wherein the remaining variables are as described for Formula I or the fourth, fifth, or sixth embodiment. In another alternative, as part of a seventh embodiment, ring A in the compound of Formula I, II, III, or IV, or a pharmaceutically acceptable salt thereof, is phenyl optionally substituted with 1 to 3 groups selected from R, wherein the remaining variables are as described for Formula I or the fourth, fifth, or sixth embodiment.

In an eighth embodiment, $R^1$ and $R^2$, in the compound of Formula I, II, III, or IV, or a pharmaceutically acceptable salt thereof, are on adjacent carbon atoms and are taken together with the carbon atoms they are attached to form a 5-membered oxygen containing heterocyclyl optionally substituted with 1 or 2 halo, wherein the remaining variables are as described for Formula I or the fourth, fifth, sixth, or seventh embodiment. Alternatively, $R^1$ and $R^2$, in the compound of Formula I, II, III, or IV, or a pharmaceutically acceptable salt thereof, are on adjacent carbon atoms and are taken together with the carbon atoms they are attached to form a dioxolanyl optionally substituted with 1 or 2 halo, wherein the remaining variables are as described for Formula I or the fourth, fifth, sixth, or seventh embodiment.

In a ninth embodiment, $R^1$ in the compound of Formula I, II, III, or IV, or a pharmaceutically acceptable salt thereof, is halo($C_1$-$C_4$)alkyl, halo($C_1$-$C_4$)alkoxy, or —$NR^cR^d$; and $R^c$ is hydrogen and $R^d$ is halo($C_1$-$C_4$)alkyl; or $R^c$ and $R^d$ are taken together to form a 4- to 7-membered heterocyclyl optionally substituted with 1 to 3 groups selected from halo, ($C_1$-$C_4$)alkyl, and oxo, wherein the remaining variables are as described for Formula I or the fourth, fifth, sixth, or seventh embodiment. Alternatively, as part of a ninth embodiment, $R^1$ in the compound of Formula I, II, III, or IV, or a pharmaceutically acceptable salt thereof, is —$OCF_3$, —$OCHF_2$, —$OCH_2CF_3$, —$CF_3$, —$CH_2CF_3$, —$CHF_2$, piperidinyl, pyrrolidinyl, azapanyl, morpholinyl, thiomorpholinyl, piperazinyl, or azetidinyl and wherein each of said heterocyclic ring is optionally substituted with 1 to 3 groups selected from halo, ($C_1$-$C_4$)alkyl, and oxo, wherein the remaining variables are as described for Formula I or the fourth, fifth, sixth, or seventh embodiment.

In a tenth embodiment, $R^2$ in the compound of Formula I, II, III, or IV, or a pharmaceutically acceptable salt thereof, is CN, halo, ($C_1$-$C_4$)alkyl, halo($C_1$-$C_4$)alkyl, or ($C_1$-$C_4$)alkoxy, wherein the remaining variables are as described for Formula I or the fourth, fifth, sixth, seventh, or ninth embodiment. Alternatively, as part of a tenth embodiment, $R^2$ in the compound of Formula I, II, III, or IV, or a pharmaceutically acceptable salt thereof, is CN or halo, wherein the remaining variables are as described for Formula I or the fourth, fifth, sixth, seventh, or ninth embodiment. In another alternative, as part of a tenth embodiment, $R^2$ in the compound of Formula I, II, III, or IV, or a pharmaceutically acceptable salt thereof, is fluoro, wherein the remaining variables are as described for Formula I or the fourth, fifth, sixth, seventh, or ninth embodiment.

In an eleventh embodiment, p in the compound of Formula I, II, III, or IV, or a pharmaceutically acceptable salt thereof, is 0, wherein the remaining variables are as described for Formula I or the fourth, fifth, sixth, seventh, ninth, or tenth embodiment.

In a twelfth embodiment, $R^5$ in the compound of Formula I, II, III, or IV, or a pharmaceutically acceptable salt thereof, is halo, ($C_1$-$C_4$)alkyl, halo($C_1$-$C_4$)alkyl, ($C_1$-$C_4$)alkoxy, —N[($C_1$-$C_4$)alkyl]2, or a 6-membered heterocyclyl, wherein the remaining variables are as described for Formula I or the fourth, fifth, sixth, seventh, eighth ninth, tenth, or eleventh embodiment. Alternatively, $R^5$ in the compound of Formula I, II, III, or IV, or a pharmaceutically acceptable salt thereof, is F, Br, Cl, —$OCH_3$, —$OCH_2CH_3$, OH, —$O(CH_2)_2CH_3$, —$NMe_2$, —$CH(CH_3)_2$, —$C(CH_3)_3$, —$OCH(CH_3)_2$, morpholinyl, —$CH_3$, or —$CF_3$, wherein the remaining variables are as described for Formula I or the fourth, fifth, sixth, seventh, eighth ninth, tenth, or eleventh embodiment.

Specific examples of compounds are provided in the EXEMPLIFICATION section and are included as part of a thirteenth embodiment herein. Pharmaceutically acceptable salts as well as the neutral forms of these compounds are also included.

Also provided herein are pharmaceutical compositions comprising a compound described herein; and a pharmaceutically acceptable carrier.

4. Uses, Formulation and Administration

Compounds and compositions described herein are generally useful for modulating the activity of UBE2K. In some aspects, the compounds and compositions described herein inhibit the activity of UBE2K.

In some aspects, the compounds and compositions described herein are useful in treating cancer. Thus, provided herein are methods of treating cancer, comprising administering to a subject in need thereof, a therapeutically effective amount of a compound described herein, or a pharmaceutically acceptable salt thereof, or a composition comprising a disclosed compound or pharmaceutically acceptable salt thereof. Also provided is the use of a compound described herein, or a pharmaceutically acceptable salt thereof, or a composition comprising a disclosed compound or pharmaceutically acceptable salt thereof, for the manufacture of a medicament for treating cancer. Also provided is a compound described herein, or a pharmaceutically acceptable salt thereof, or a composition comprising a disclosed compound or pharmaceutically acceptable salt thereof, for use in treating cancer.

Cancers treatable by the present methods include, but are not limited to liquid cancer such as, e.g., acute myeloid leukemia, acute lymphoblastic leukemia, and chronic lymphocytic leukemia or solid tumors such as, e.g., pancreatic cancer, ovarian cancer, breast cancer, colon cancer, and gastrointestinal cancer.

In certain aspects, a composition described herein is formulated for administration to a subject in need of such composition. Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions described herein may be aqueous or oleaginous suspension. These suspensions may be formulated according to techniques known in the art using suitable dispersing or wetting agents and suspending agents.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

EXEMPLIFICATION

Representative examples of the disclosed compounds are illustrated in the following non-limiting methods, schemes, and examples.

9
General Synthetic Route

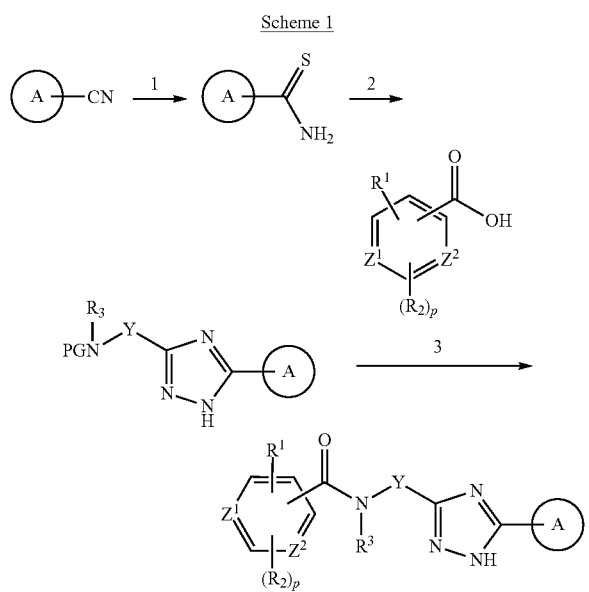

Compounds of Formula I can be prepared according to the general scheme 1 above, where e.g., the appropriate cyano starting material is reacted with an ammonium sulfide (e.g., [NH$_4$]$_2$S) optionally in the present of base and elevated temperature to form the corresponding sulfide amine. See Step 1. Cyclization to the corresponding heteroaryl then takes place in Step 2 with the appropriate protected amine where PG is an amine protecting group such as an acid labile protecting group. The amine is then unmasked (e.g., with acid) and then couple with the appropriate acid (see Step 3) using e.g., diimide based reagents or similar to form the Compounds of Formula I. Variables have the same meanings as described herein.

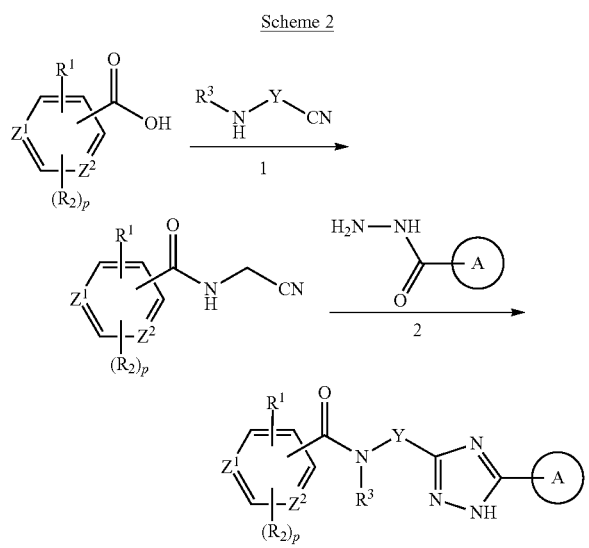

10

Compounds of Formula I can be also prepared according to the general scheme 2 above, where e.g., the appropriate amino and carboxylic acid starting material are reacted (e.g., in the presence of base and optionally an additive) to form the cyano product in Step 1. The cyano may then be cyclic e.g., at elevated temperature and optionally in the present of an inorganic based to form the compounds of Formula 1 in Step 2. Variables have the same meanings as described herein.

EXEMPLIFIED SYNTHESES

Synthesis of N-((5-(thiophen-2-yl)-1H-pyrazol-3-yl)methyl)-2-(trifluoromethyl)benzamide (Compound 2)

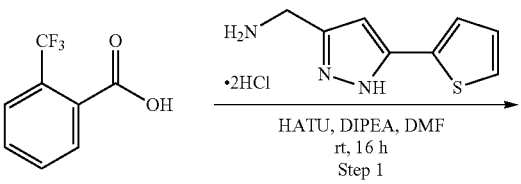

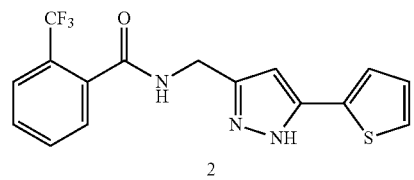

To a solution of 2-(trifluoromethyl) benzoic acid (500 mg, 2.626 mmol) in DMF (2 mL) cooled to 0° C. was added (5-(thiophen-2-yl)-1H-pyrazol-3-yl) methanamine (662 mg, 2.629 mmol, 1 eq), HATU (380 mg, 5.258 mmol) and DIPEA (129 mg, 8.097 mmol). The solution was stirred at room temperature for 16 hrs. After completion of the reaction, the solvent was distilled off, followed by the addition of water (10 ml) and extracted with EtOAc (50 mL×2 times) and dried over Na$_2$SO$_4$. It was then concentrated under reduced pressure to get crude product. The crude product was then purified by flash column chromatography (eluent: 20% EtOAc/n-hexane) to get title compound (650 mg, 70%) product as N-((5-(thiophen-2-yl)-1H-pyrazol-3-yl) methyl)-2-(trifluoromethyl)benzamide as off white solid. $^1$H NMR (400 MHz, DMSO-d$_6$) δ 12.77 (s, 1H), 8.94 (s, 1H), 7.77 (d, J=8.0 Hz, 1H), 7.40-7.70 (m, 2H), 7.40 (m, 2H), 7.32 (s, 1H), 7.05 (m, 1H), 6.40-6.48 (m, 1H), 4.40 (s, 2H). LCMS: M/Z 352.1[M+H]$^+$ The following compounds in Table 1 were prepared using similar procedures to those described above for Compound 1 using the appropriate starting materials.

TABLE 1

| Example/ Compound Nos. | Structure | LC-MS [M + H]+ (m/z) | NMR Data |
| --- | --- | --- | --- |
| 1 | (2-CF3-phenyl)-C(=O)-NH-CH2-pyrazole-thiophene | 352.1 | |
| 3 | (3-CF3-phenyl)-C(=O)-NH-CH2-pyrazole-thiophene | 352.1 | |
| 4 | (2-OCHF2-phenyl)-C(=O)-NH-CH2-pyrazole-thiophene | 350 | $^1$H NMR (400 MHz, DMSO) rotamer δ 12.74 (s, 1H), 8.73 (s, 1H), 7.50-7.59 (m, 2H), 7.00-7.40 (m, 6H), 6.42 (s, 1H), 4.40-4.47 (s, 2H) |
| 5 | (2-OCF3-phenyl)-C(=O)-NH-CH2-pyrazole-thiophene | 368.1 | $^1$H NMR (400 MHz, DMSO-d$_6$) δ 12.76 (s, 1H), rot 8.98 (s, 1H), 7.56-7.62 (m, 2H), 7.39-7.48 (m, 3H), 7.29 (s, 1H), rot 7.05 (s, 1H), rot 6.44 (s, 1H), 4.45 (s, 2H). |
| 6 | (2-CHF2-phenyl)-C(=O)-NH-CH2-pyrazole-thiophene | 334 | $^1$H NMR (400 MHz, DMSO) δ 12.95 (d, J = 136.7 Hz, 1H), 9.12 (d, J = 30.8 Hz, 1H), 7.79-7.58 (m, 3H), 7.54-7.30 (m, 2H), 7.07 (dd, J = 18.0, 14.3 Hz, 1H), 6.46 (d, J = 35.8 Hz, 1H), 4.45 (dd, J = 27.5, 5.7 Hz, 2H). |
| 7 | (3-OCF3-phenyl)-C(=O)-NH-CH2-pyrazole-thiophene | 368.2 | |
| 8 | (2-CH2CF3-phenyl)-C(=O)-NH-CH2-triazole-thiophene | 367.1 | |

TABLE 1-continued

| Example/ Compound Nos. | Structure | LC-MS [M + H]+ (m/z) | NMR Data |
|---|---|---|---|
| 9 | 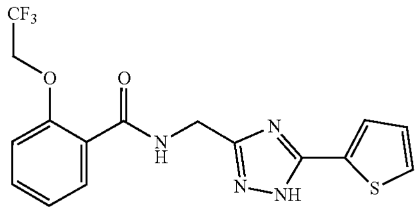 [SMILES: O=C(NCc1n[nH]c(-c2cccs2)n1)c1ccccc1OCC(F)(F)F] | 383.1 | |
| 10 | 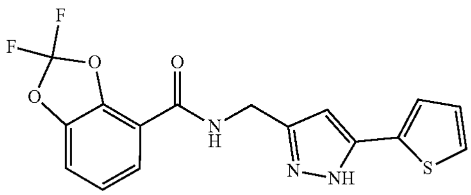 [SMILES: O=C(NCc1cc(-c2cccs2)[nH]n1)c1cccc2c1OC(F)(F)O2] | 364.2 | |
| 11 | 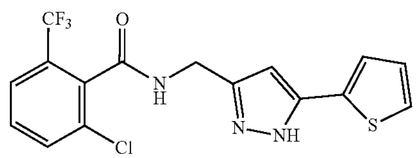 [SMILES: O=C(NCc1cc(-c2cccs2)[nH]n1)c1c(Cl)cccc1C(F)(F)F] | 342 | ¹H NMR (400 MHz, DMSO) δ 8.93 (d, J = 3.3 Hz, 1H), 8.79 (d, J = 8.5 Hz, 1H), 8.21 (d, J = 8.0 Hz, 1H), 8.13 (d, J = 7.9 Hz, 1H), 8.02 (t, J = 8.2 Hz, 1H), 7.75-7.70 (m, 1H), 3.29 (s, 2H). |
| 12 | 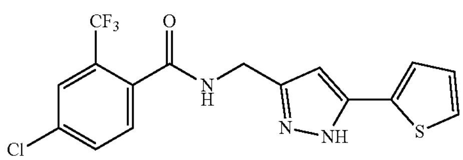 [SMILES: O=C(NCc1cc(-c2cccs2)[nH]n1)c1ccc(Cl)cc1C(F)(F)F] | 386 | ¹H NMR (400 MHz, DMSO-d₆) δ 12.79 (s, 1H), 9.01 (s, 1H), 7.90-7.88 (m, 2H), 7.65-7.66 (d, J = 8.0 Hz, 1H), 7.55-7.59 (m, 1H), 7.30 (s, 1H), 7.32 (s, 1H), 7.04-7.12 (m, 1H), 6.48 (s, 1H), 4.45 (s, 2H). |
| 13 | 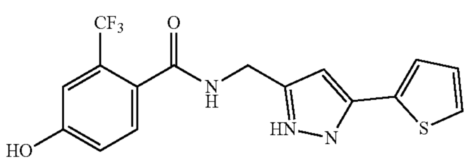 [SMILES: O=C(NCc1cc(-c2cccs2)[nH]n1)c1ccc(O)cc1C(F)(F)F] | 368 | ¹H NMR (400 MHz, DMSO) rotamer δ 12.72 (s, 1H), 10.35 (s, 1H), 8.74 (s, 1H), 7.31-7.54 (m, 3H), 7.04-7.11 (m, 3H), 6.36-6.45 (s, 1H), 4.35-4.42 (s, 2H) |
| 14 | 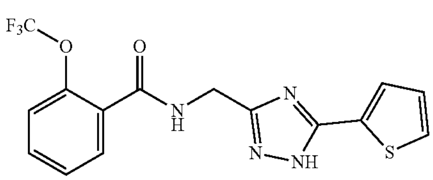 [SMILES: O=C(NCc1n[nH]c(-c2cccs2)n1)c1ccccc1OC(F)(F)F] | 369.1 | |
| 15 | 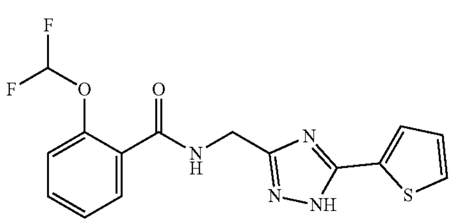 [SMILES: O=C(NCc1n[nH]c(-c2cccs2)n1)c1ccccc1OC(F)F] | 351.1 | |

TABLE 1-continued
| Example/ Compound Nos. | Structure | LC-MS [M + H]+ (m/z) | NMR Data |
|---|---|---|---|
| 68 | 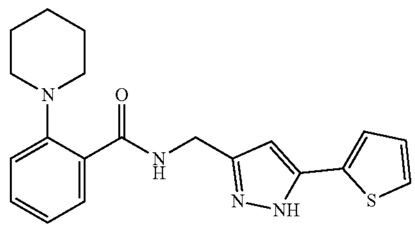 [SMILES: O=C(NCc1cc(-c2cccs2)[nH]n1)c1ccccc1N1CCCCC1] | 367.28 | $^1$H NMR (400 MHz, DMSO-d$_6$) rotamer δ 12.80 (s, 1H), 10.18 (s, 1H), 7.88 (s, 1H), 7.39-7.47 (m, 2H), 7.26-7.32 (m, 2H), 7.16-7.20 (m, 1H), 7.04 (s, 1H), 6.53 (s, 1H), 4.55 (s, 2H), 2.81 (s, 4H), 1.50 (s, 4H), 1.40 (s, 2H) |
| 69 | 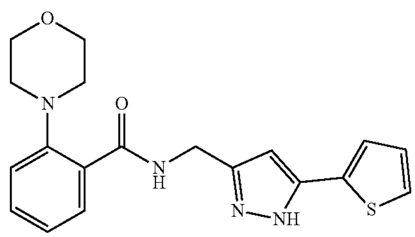 [SMILES: O=C(NCc1cc(-c2cccs2)[nH]n1)c1ccccc1N1CCOCC1] | 369.1 | $^1$H NMR (400 MHz, DMSO-d$_6$) rotamer δ 9.64 (s, 1H), 7.76 (s, 1H), 7.33-7.46 (m, 3H), 7.22 (d, J = 8 Hz, 1H), 7.15-7.18 (m, 1H), 7.05 (s, 1H), 6.51 (s, 1H), 4.52 (s, 2H), 3.54 (s, 4H), 2.86 (s, 4H) |
| 70 | 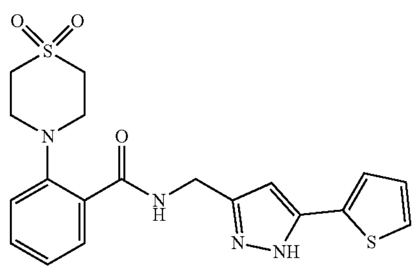 [SMILES: O=C(NCc1cc(-c2cccs2)[nH]n1)c1ccccc1N1CCS(=O)(=O)CC1] | 417.1 | $^1$H NMR (400 MHz, DMSO-d$_6$) rotamer δ 12.79 (s, 1H), 9.13 (s, 1H), 7.64 (s, 1H), 7.35-7.44 (m, 3H), 7.25 (d, J = 8 Hz, 1H), 7.16 (t, J = 14.4 Hz, 1H), 7.05 (s, 1H), 6.45 (s, 1H), 4.52 (s, 2H), 3.36 (s, 4H), 3.17 (s, 4H) |
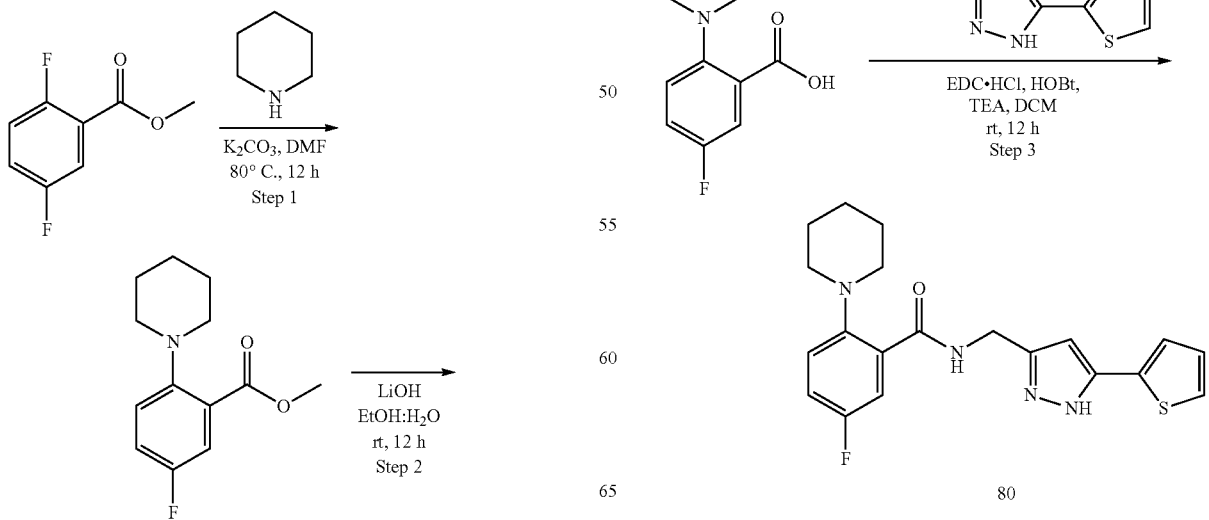
Synthesis of 5-fluoro-2-(piperidin-1-yl)-N-((5-(thiophen-2-yl)-1H-pyrazol-3-yl)methyl) benzamide (compound 80):

Step 1: methyl 5-fluoro-2-(piperidin-1-yl) benzoate

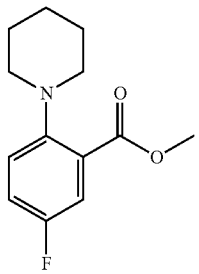 [SMILES: COC(=O)c1cc(F)ccc1N1CCCCC1]

To a stirred solution of methyl 2,5-difluorobenzoate (500 mg, 2.906 mmol) in DMF (10 mL) was added piperidine (0.37 ml, 3.488 mmol) followed by $K_2CO_3$ (1 g, 7.267 mmol) and the reaction mixture was stirred at 80° C. for 12 h. After completion of the reaction, solvent was concentrated under reduced pressure, diluted with water (10 mL) and extracted with EtOAc (2×15 mL). The combined organic layer was dried over $Na_2SO_4$, concentrated under reduced pressure to get crude compound. The crude compound was purified by flash column chromatography (eluent: 40% EtOAc in Hexane) to afford methyl 5-fluoro-2-(piperidin-1-yl) benzoate as brown solid (350 mg, 50.87%). $^1$H NMR (400 MHz, DMSO-$d_6$): δ 7.33-7.36 (m, 1H), 7.26-7.31 (m, 1H), 7.10-7.13 (m, 1H), 3.79 (s, 3H), 2.82-2.87 (m, 4H), 1.58 (s, 4H), 1.48 (s, 2H). LC-MS m/z (M–H): 238.0

Step 2: 5-fluoro-2-(piperidin-1-yl) benzoic acid

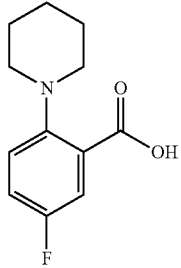 [SMILES: O=C(O)c1cc(F)ccc1N1CCCCC1]

To a stirred solution of methyl 5-fluoro-2-(piperidin-1-yl) benzoate (250 mg, 1.054 mmol) in THF:H2O (10 mL+5 mL) was added LiOH (200 mg, 4.219 mmol). Then the reaction was stirred at rt for 12 h. After completion of reaction, the solvent was distilled off, diluted with EtOAc (10 mL), organic layer was separated and the aqueous layer was acidified with 1N HCl solution (5 mL), extracted with EtOAc (2×10 mL). The combined organic layer was dried over $Na_2SO_4$, conc. on rotavapour to afford 5-fluoro-2-(piperidin-1-yl) benzoic acid (200 mg, 75.47%) as a brown solid.
$^1$H NMR (400 MHz, DMSO-$d_6$) rotamer δ 18.55 (s, 1H), 11.97 (s, 1H), 7.82-7.85 (m, 1H), 7.69-7.72 (m, 1H), 7.51-7.56 (m, 1H), 3.07 (t, J=5.2 Hz, 4H), 1.89 (bs, 2H), 1.73 (bs, 4H), 1.60 (d, J=4.8 Hz, 2H), LC-MS m/z (M–H): 238.0

Step 3: 5-fluoro-2-(piperidin-1-yl)-N-((5-(thiophen-2-yl)-1H-pyrazol-3-yl) methyl) benzamide

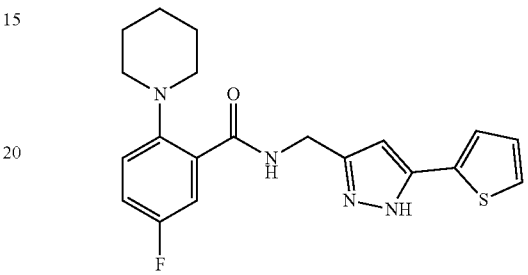

To a stirred solution of 5-fluoro-2-(piperidin-1-yl) benzoic acid (300 mg, 1.345 mmol) in DCM (20 mL) was added EDC.HCl (385 mg, 2.015 mmol) and HOBt (308 mg, 2.281 mmol) at 0° C. The reaction mixture was allowed to stir for 15 min at 0° C. and to it was added (5-(thiophen-2-yl)-1H-pyrazol-3-yl) methanamine (310 mg, 1.614 mmol) and the reaction was stirred at room temperature for 12 h. After completion of the reaction, solvent was concentrated under reduced pressure, diluted with water (10 mL) and extracted with EtOAc (2×15 mL). The combined organic layer was dried over $Na_2SO_4$, concentrated under reduced pressure to get crude compound. The crude compound was purified by flash column chromatography (eluent: 40% EtOAc in Hexane) to afford 5-fluoro-2-(piperidin-1-yl)-N-((5-(thiophen-2-yl)-1H-pyrazol-3-yl) methyl) benzamide as off white solid (11 mg, 21.31%). $^1$H NMR (400 MHz, DMSO-$d_6$) rotamer δ 12.84 (s, 1H), 10.53 (s, 1H), 7.54-7.64 (m, 1H), 7.32-7.40 (m, 4H), 7.04-7.11 (m, 1H), 6.54 (s, 1H), 4.47-4.56 (m, 2H), 2.78 (s, 4H), 1.47 (s, 4H), 1.39 (s, 2H). LC-MS m/z (M–H): 385.0.

The following compounds in Table 2 were prepared using similar procedures to those described above for Compound 80 using the appropriate starting materials.

TABLE 2

| Example/Compound Nos. | Structure | LC-MS [M + H]+ (m/z) | NMR Data |
|---|---|---|---|
| 71 | 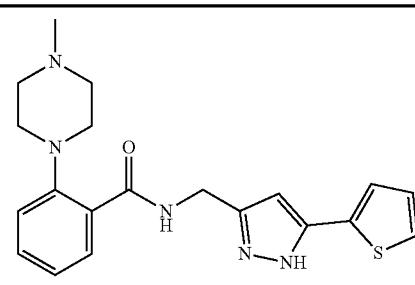 | 382.1 | $^1$H NMR (400 MHz, DMSO-$d_6$): δ 9.83 (brs, 1H), 7.83 (brs, 1H), 7.43-7.55 (m, 3H), 7.04-7.49 (m, 4H), 6.48 (s, 1H), 4.52 (s, 2H), 2.84 (s, 4H), 2.24 (s, 4H), 2.02 (brs, 3H). |

TABLE 2-continued
| Example/ Compound Nos. | Structure | LC-MS [M + H]+ (m/z) | NMR Data |
|---|---|---|---|
| 94 | 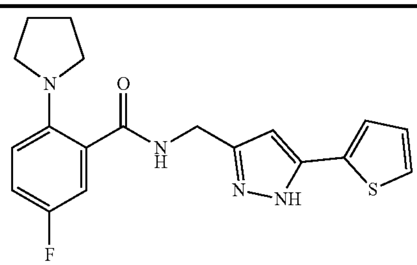 | 370.9 | ¹H NMR (400 MHz, DMSO-d₆): δ 13.11 (s, 1H), 8.94 (d, J = 5.6 Hz, 1H), 7.40 (d, J = 4.8 Hz, 1H), 7.33 (d, J = 2 Hz, 1H), 7.14-7.05 (m, 3H), 6.76-6.73 (m, 1H), 6.48-6.41 (m, 1H), 4.40 (dd, J = 24 Hz, 4.4 Hz, 2H), 3.08 (brs, 4H), 1.78 (brs, 4H) |
| 103 | 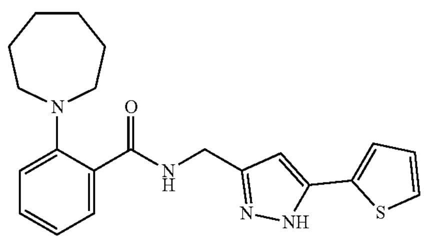 [SMILES: O=C(NCc1cc(-c2cccs2)[nH]n1)c1ccccc1N1CCCCCC1] | 381.1 | ¹H NMR (400 MHz, DMSO-d₆) rotamer δ 12.78 (S, 1H), 9.75 (s, 1H), 7.56-7.62 (m, 1H), 7.31-7.39 (m, 3H), 6.93-7.12 (m, 3H), 6.48 (s, 1H), 4.43-4.49 (m, 2H), 3.11 (s, 4H), 1.61 (bs, 4H), 1.45 (s, 4H), 1.22 (s, 2H) |
Synthesis of N-((5-(2-methoxyphenyl)-1H-pyrazol-3-yl) methyl)-2-(piperidin-1-yl) benzamide (Compound 102)
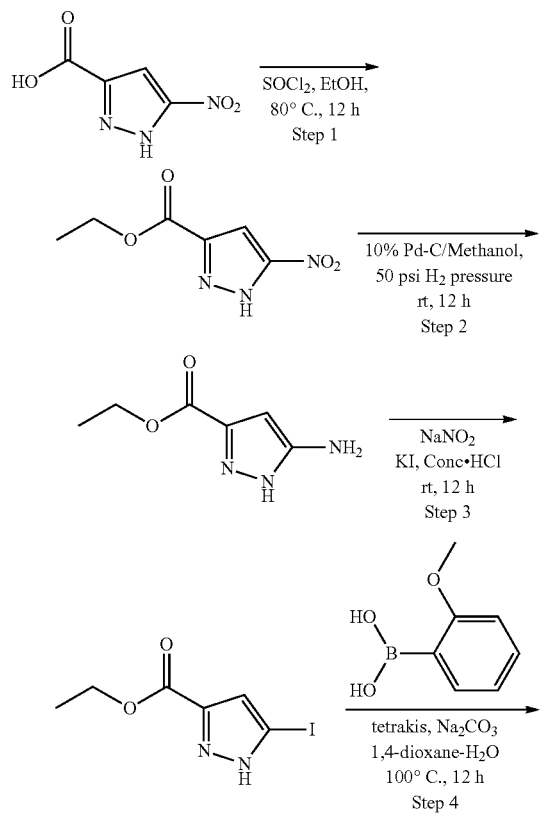
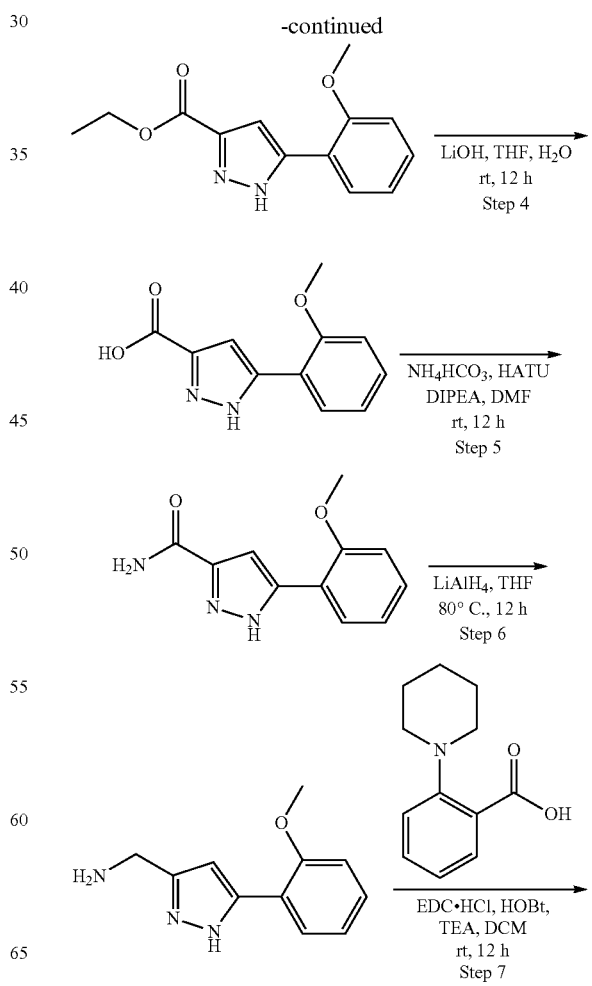

-continued

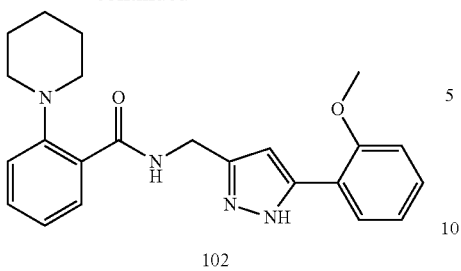

102

Step 1: Synthesis of ethyl 5-nitro-1H-pyrazole-3-carboxylate

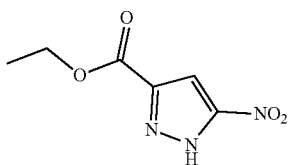

To a stirred solution 5-nitro-1H-pyrazole-3-carboxylic acid (5 g, 31.84 mmol) in ethanol (50 mL) was added $SOCl_2$ (8 ml) at 0° C. The reaction mixture was stirred at 80° C. for 12 h. After completion of reaction, the solvent was distilled off, diluted with EtOAc (50 mL) and washed once with sat. $NaHCO_3$ solution (50 mL), followed by water (50 mL), organic layer was separated, dried over $Na_2SO_4$, conc. on rotavapour to get the crude compound. The crude compound was triturated with diethyl ether (25 mL) to afford ethyl 5-nitro-1H-pyrazole-3-carboxylate as off white solid (4.5 g, 77.58%). $^1H$ NMR (400 MHz, DMSO-$d_6$) rotamer δ 15.19 (s, 1H), 7.48 (s, 1H), 4.32-4.37 (m, 2H), 1.31 (t, J=7.2 Hz, 3H). LC-MS m/z (M−H): 186.1

Step 2: Synthesis of ethyl 5-amino-1H-pyrazole-3-carboxylate

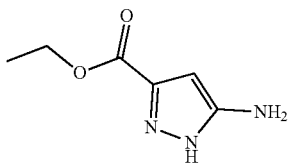

To a stirred solution ethyl 5-nitro-1H-pyrazole-3-carboxylate (10 g, 54.05 mmol) in AcOH:THF (1:1) was added Pd/C (wt/wt, 100 mg) and the reaction mixture was allowed to hydrogenate at 50 psi for 12 h. After completion of reaction, the mixture was filtered through celite bed, washed with methanol (2×50 m), dried over anhydrous $Na_2SO_4$, concentrated on rotavapor to afford ethyl 5-amino-1H-pyrazole-3-carboxylate as off white solid (8 g, 95.57%). $^1H$ NMR (400 MHz, DMSO-$d_6$) rotamer δ 12.09 (s, 1H), 5.63 (s, 1H), 5.15 (s, 1H), 4.16 (s, 2H), 1.23 (s, 3H), LC-MS m/z (M−H): 156.1

Step 3: Synthesis of ethyl 5-iodo-1H-pyrazole-3-carboxylate

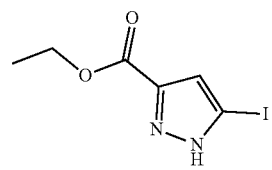

To a stirred solution of ethyl 5-amino-1H-pyrazole-3-carboxylate (1.2 g, 7.74 mmol) in HCl (12 mL) was added $NaNO_2$ (658 mg, 9.67 mmol) in $H_2O$ (6 mL) at 0° C. The resulting mixture was stirred for 30 min at 0° C. and to it was added KI (1.6 g, 9.63 mmol) in $H_2O$ (6 mL) slowly at the same temperature, the mixture was allowed to warm up to room temperature and stirred for 12 h. After completion of reaction, the reaction mixture was diluted with cold water (20 mL) and extracted with EtOAc (2×25 mL). The combined organic layer was washed once with sat. sodium thiosulfate solution (20 mL) followed by $H_2O$ (20 ml). The organic layer was dried over $Na_2SO_4$, conc. on rotavapour to get the crude compound. The crude compound was purified by flash column chromatography (eluent: 10% EtOAc in Hexane) to afford ethyl 5-iodo-1H-pyrazole-3-carboxylate as off white solid (320 mg, 16%). $^1H$ NMR (400 MHz, DMSO-$d_6$) rotamer δ 14.23 (s, 1H), 6.88 (s, 1H), 4.27-4.32 (m, 2H), 1.28 (t, J=7.2 Hz, 3H), LC-MS m/z (M−H): 266.92

Step 4: Synthesis of ethyl 5-(2-methoxyphenyl)-1H-pyrazole-3-carboxylate

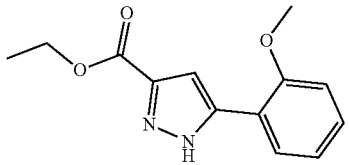 [SMILES: CCOC(=O)c1cc(-c2ccccc2OC)[nH]n1]

To a stirred solution of ethyl 5-iodo-1H-pyrazole-3-carboxylate (100 mg, 0.273 mmol) in 1,4-dioxane-$H_2O$ (8 mL+2 mL) was added (2-methoxyphenyl) boronic acid (45 mg, 0.296 mmol) and $Na_2CO_3$ (72 mg, 0.679 mmol). The reaction mixture was degassed with argon for 10 min and to the mixture was added palladium-tetrakis(triphenylphosphine (31 mg, 0.026 mmol) and the reaction was heated at 100° C. for 12 h. After completion of the reaction, solvent was concentrated under reduced pressure, diluted with water (10 mL) and extracted with EtOAc (2×15 mL). The combined organic layer was dried over $Na_2SO_4$, concentrated under reduced pressure to get crude compound. The crude compound was purified by flash column chromatography (eluent: 60% EtOAc in Hexane) to afford ethyl 5-(2-methoxyphenyl)-1H-pyrazole-3-carboxylate as off white solid (47 mg, 70.14%). $^1H$ NMR (400 MHz, DMSO-$d_6$) rotamer δ 13.56 (s, 1H), 7.72 (d, J=7.6 Hz, 1H), 7.30-7.39 (m, 1H), 7.11-7.20 (m, 3H), 7.01-7.05 (m, 1H), 4.25-4.33 (m, 2H), 3.89 (s, 3H), 1.29 (d, J=7.2 Hz, 3H), LC-MS m/z (M−H): 247

Step 5: Synthesis of 5-(2-methoxyphenyl)-1H-pyrazole-3-carboxylic acid

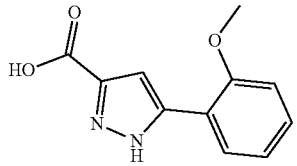 [SMILES: COc1ccccc1-c1cc(C(=O)O)n[nH]1]

To a stirred solution of ethyl 5-(2-methoxyphenyl)-1H-pyrazole-3-carboxylate (400 mg, 1.62 mmol) in THF:H2O (20 mL+10 mL) at 0° C. was added LiOH.H$_2$O (260 mg, 6.504 mmol) and the reaction mixture was stirred at room temperature for 12 h. After completion of reaction, the solvent was distilled off, diluted EtOAc (10 mL), organic layer was separated and the aqueous layer was acidified with 1N HCl solution (5 mL), extracted with EtOAc (2×25 mL). The combined organic layer was dried over Na$_2$SO$_4$, concentrated on rotavapor to afford 5-(2-methoxyphenyl)-1H-pyrazole-3-carboxylic acid as brown solid (250 mg, 70.62%). $^1$H NMR (400 MHz, DMSO-d$_6$) rotamer δ 13.21 (s, 1H), 7.77 (d, J=6.8 Hz, 1H), 7.34 (t, J=8.0 Hz, 1H), 7.11-7.14 (m, 2H), 7.01 (t, J=7.2 Hz, 1H), 3.88 (s, 3H). LC-MS m/z (M−H): 219

Step 6: Synthesis of 5-(2-methoxyphenyl)-1H-pyrazole-3-carboxamide

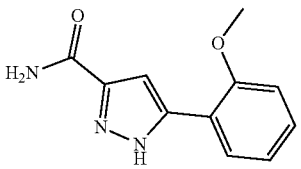 [SMILES: COc1ccccc1-c1cc(C(N)=O)n[nH]1]

To a stirred solution of 5-(2-methoxyphenyl)-1H-pyrazole-3-carboxylic acid (250 mg, 1.146 mmol) in DMF (6 mL) was added HATU (650 mg, 1.720 mmol), DIPEA (740 mg, 3.440 mmol) and NH$_4$HCO$_3$ (360 mg, 4.587 mmol) at room temperature and stirred at for 12 h. After the completion of the reaction, the mixture was extracted with water and ethyl acetate. The ethyl acetate layer was dried over anhydrous sodium sulphate and concentrated under reduced pressure. The crude compound was purified by Grace Column chromatography, eluted with 80% EtOAc in pet ether) to afford 5-(2-methoxyphenyl)-1H-pyrazole-3-carboxamide (80 mg, yield: 32.25%) as an off white solid. $^1$H NMR (400 MHz, DMSO-d$_6$) rotamer δ 13.24 (s, 1H), 7.88-7.94 (m, 1H), 7.68 (d, J=7.6 Hz, 1H), 7.45 (s, 1H), 7.27-7.38 (m, 1H), 6.96-7.19 (m, 4H), 3.89 (s, 3H). LC-MS m/z (M−H): 218

Step 7: Synthesis of (5-(2-methoxyphenyl)-1H-pyrazol-3-yl) methanamine

To a stirred solution of 5-(2-methoxyphenyl)-1H-pyrazole-3-carboxamide (80 mg, 0.368 mmol) in THF (10 mL) was added lithium aluminium hydride (54 mg, 1.474 mmol) at 0° C. and stirred the reaction mixture at 80° C. for 12 h. After completion of reaction, the reaction was quenched with a slurry of Na$_2$SO$_4$, followed by addition of EtOAc (20 mL), filtered through celite pad. The filtrate obtained was concentrated under reduced pressure to afford (5-(2-methoxyphenyl)-1H-pyrazol-3-yl) methanamine as off white solid (45 mg, 60%), which was used for next step without further purification. LC-MS m/z (M−H): 204

Step 8: N-((5-(2-methoxyphenyl)-1H-pyrazol-3-yl)methyl)-2-(piperidin-1-yl) benzamide

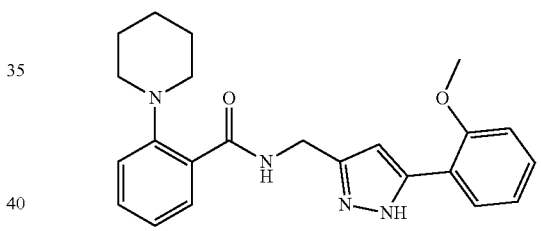

To a stirred solution of 2-(piperidin-1-yl) benzoic acid (45 mg, 0.22 mmol) in dichloromethane was added EDC.HCl (63 mg, 0.33 mmol) and HOBt (50 mg, 0.32 mmol) at 0° C. The reaction mixture was allowed to stir for 15 min at 0° C. and to the resultant mixture was added (5-(2-methoxyphenyl)-1H-pyrazol-3-yl) methanamine (45 mg, 0.26 mmol). The reaction mixture was stirred at room temperature for 12 h. After completion of the reaction, solvent was concentrated under reduced pressure, diluted with water (10 mL) and extracted with EtOAc (2×15 mL). The combined organic layer was dried over Na$_2$SO$_4$, concentrated under reduced pressure to get crude compound. The crude compound was purified by preparative TLC. (eluted with 5% MeOH/DCM) to afford 5-fluoro-2-(piperidin-1-yl)-N-((5-(thiophen-2-yl)-1H-pyrazol-3-yl) methyl) benzamide as off white solid (5.3 mg, 6.16%). $^1$H NMR (400 MHz, DMSO-d$_6$) rotamer δ 12.80 (s, 1H), 10.22 (s, 1H), 7.09 (d, J=7.6 Hz, 1H), 7.64 (bs, 1H), 7.40-7.47 (m, 1H), 7.27-7.29 (m, 2H), 7.18 (t, J=7.2 Hz, 1H), 7.09 (d, J=8.0 Hz, 1H), 6.99 (bs, 1H), 6.66 (s, 1H), 4.51 (s, 2H), 3.85 (s, 3H), 2.80 (s, 4H), 1.49 (s, 4H), 1.38 (s, 2H). LC-MS m/z (M−H): 391.0

The following compounds in Table 3 were prepared using similar procedures to those described above for Compound 102 using the appropriate starting materials.

TABLE 3

| Example/Compound Nos. | Structure | LC-MS [M + H]+ (m/z) | NMR Data |
|---|---|---|---|
| 55 | 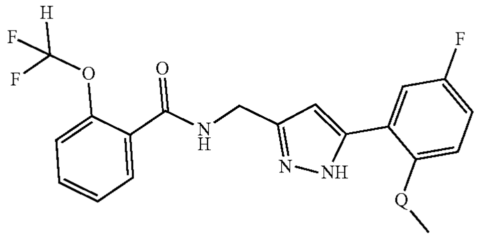 | 393.1 | ¹H NMR (400 MHz, DMSO-d₆) δ 12.82 (s, 1H), 8.72 (s, 1H), 7.49-7.57 (m, 3H), 7.29-7.35 (m, 1H), 7.22 (d, J = 8 Hz, 1H), 7.13-7.17 (m, 2H), 6.72 (s, 1H), 4.44 (s, 2H), 3.85 (s, 3H) |
| 91 | 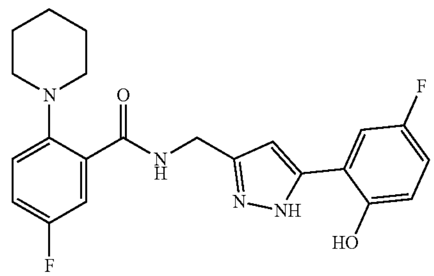 [SMILES: O=C(NCc1cc(-c2cc(F)ccc2O)[nH]n1)c1cc(F)ccc1N1CCCCC1] | 413.0 | ¹H NMR (400 MHz, DMSO-d₆) δ 10.51 (s, 1H), 7.27 (s, 1H), 7.50 (bs, 2H), 7.41 (s, 1H), 6.85-6.95 (m, 3H), 4.59 (s, 2H), 2.92 (s, 4H), 1.55 (s, 4H), 1.43 (s, 2H) |
| 100 | 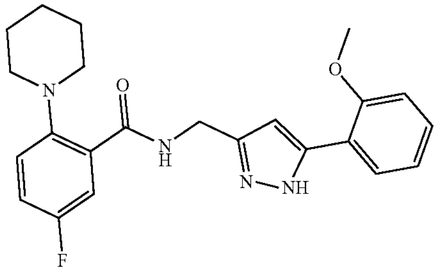 [SMILES: COc1ccccc1-c1cc(CNC(=O)c2cc(F)ccc2N2CCCCC2)n[nH]1] | 409.5 | |
| 110 | 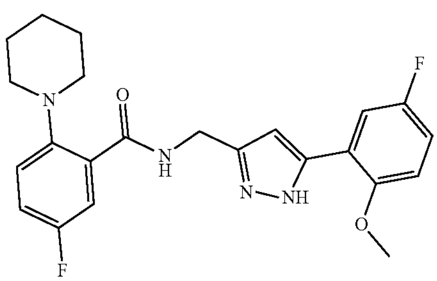 [SMILES: COc1ccc(F)cc1-c1cc(CNC(=O)c2cc(F)ccc2N2CCCCC2)n[nH]1] | 527.2 | ¹H NMR (400 MHz, DMSO-d₆) rotamer δ 12.92 (s, 1H), 10.58 (s, 1H), 7.66 (s, 2H), 7.32-7.39 (m, 2H), 7.08-7.13 (m, 2H), 6.76 (s, 1H), 4.51 (s, 2H), 3.81 (s, 3H), 2.77 (s, 4H), 1.48 (s, 4H), 1.37 (s, 2H). |

Synthesis of 2-(4,4-difluoropiperidin-1-yl)-N-((5-(thiophen-2-yl)-1H-1,2,4-triazol-3-yl) methyl) benzamide (Compound 76)

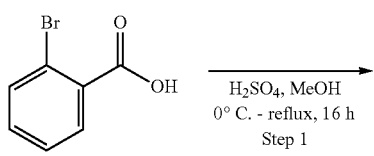

H₂SO₄, MeOH
0° C. - reflux, 16 h
Step 1

-continued

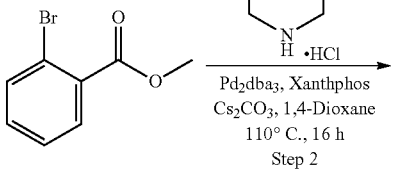

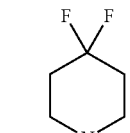

Pd₂dba₃, Xanthphos
Cs₂CO₃, 1,4-Dioxane
110° C., 16 h
Step 2

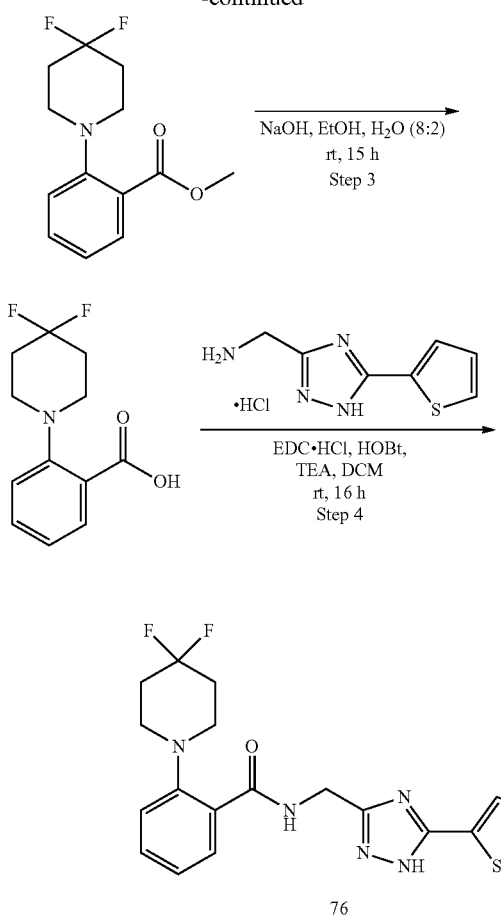

Step 1: Synthesis of methyl 2-bromobenzoate

To the stirred solution of 2-bromobenzoic acid (10 gm, 50 mmol) in methanol (80 ml) at 0° C., added concentrated sulphuric acid (8 ml, 150 mmol) and the reaction mixture stirred at reflux temperature for 16 hrs. After the completion of reaction, reaction mixture was concentrated completely under reduced pressure. The crude product quenched with cold water and extracted with ethyl acetate (2×100 mL). Combined organic layer was washed with water (50 mL), saturated sodium bicarbonate solution (50 mL), and dried on sodium sulphate. The organic layer was concentrated to obtain pure yellow coloured liquid product methyl 2-bromobenzoate (9.0 gm, 83% yield). $^1$H NMR (400 MHz, CDCl$_3$) δ 7.79 (dd, J=7.4, 1.9 Hz, 1H), 7.65 (dt, J=25.6, 12.6 Hz, 1H), 7.42-7.29 (m, 2H), 3.94 (s, 3H).

Step 2: Synthesis of Methyl 2-(4,4-difluoropiperidin-1-yl) benzoate

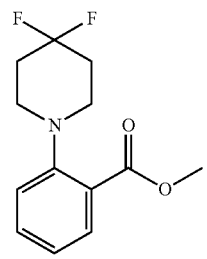 [SMILES: COC(=O)c1ccccc1N1CCC(F)(F)CC1]

To the stirred solution of methyl 2-bromobenzoate (250 mg, 1.162 mmol) in 1,4-dioxane (5 mL), was added, 4,4-difluoropiperidine hydrochloride (202 mg, 1.2818 mmol), Xanthphos (335 mg, 0.581 mmol) and CS$_2$CO$_3$ (944 mg, 2.905 mmol). The reaction mixture was degassed with argon for 5 times followed by the addition of Pd$_2$dba$_3$ (106 mg, 0.1166 mmol). The reaction mixture was stirred for 16 h at 110° C. After the completion of reaction, the mixture was cooled, quenched with water and extracted with ethyl acetate (2×50 mL). The combined organic layer washed with brine and dried over sodium sulphate. The dried organic layer was concentrated under reduced pressure to get crude product as yellow liquid. It was purified by flash column chromatography using ethyl acetate and hexane as eluting agent. Methyl 2-(4,4-difluoropiperidin-1-yl) benzoate pure material was obtained (40 mg, 16%). $^1$H NMR (400 MHz, CDCl$_3$) δ 7.85-7.73 (m, 1H), 7.42 (dd, J=11.1, 4.4 Hz, 1H), 7.10-6.98 (m, 2H), 3.89 (s, 3H), 3.22-3.07 (m, 4H), 2.16 (ddd, J=19.3, 13.8, 5.6 Hz, 4H).

Step 3: Synthesis of 2-(4,4-difluoropiperidin-1-yl) benzoic acid

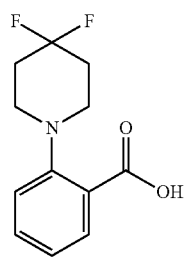 [SMILES: O=C(O)c1ccccc1N1CCC(F)(F)CC1]

To the stirred solution of methyl 2-(4,4-difluoropiperidin-1-yl)benzoate (770 mg, 3.019 mmol) in ethanol (8 mL), was added water (2 mL) and NaOH (480 mg, 12.078 mmol). The Reaction mixture was stirred at room temperature for 16 h. After the completion of reaction, the reaction mixture was diluted with water and the aqueous layer washed with ethyl acetate (2×50 mL). The aqueous layer-containing product was acidified with 2N HCl and extracted with ethyl acetate (2×50 mL). The combined organic layer was washed with brine (50 mL) and dried over sodium sulfate. The organic layer was concentrated under reduced pressure to get the product 2-(4,4-difluoropiperidin-1-yl) benzoic acid (580 mg, 80%) as off-white solid. $^1$H NMR (400 MHz, DMSO-d$_6$) δ 14.99 (s, 1H), 7.87 (d, J=7.5 Hz, 1H), 7.57 (t, J=7.5 Hz, 1H), 7.49 (d, J=8.0 Hz, 1H), 7.26 (t, J=7.3 Hz, 1H), 3.15 (s, 4H), 2.16 (t, J=13.9 Hz, 4H). LC-MS m/z (M+H): 242.0.

Step 4: 2-(4,4-difluoropiperidin-1-yl)-N-((5-(thiophen-2-yl)-1H-1,2,4-triazol-3-yl) methyl) benzamide

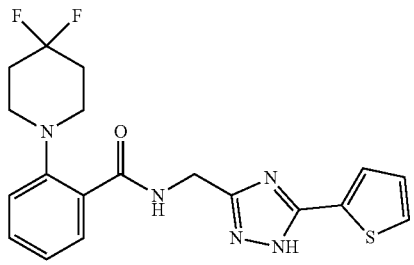 [SMILES: O=C(NCc1n[nH]c(-c2cccs2)n1)c1ccccc1N1CCC(F)(F)CC1]

To the stirred solution of 2-(4,4-difluoropiperidin-1l-yl) benzoic acid (25 mg, 0.104 mmol) in dichloromethane (5 mL), added EDC.HCl (29 mg, 0.156 mmol), HOBt (23 mg, 0.156 mmol) and triethylamine (0.067 ml, 0.468 mmol) followed by 5-(thiophen-2-yl)-1H-1,2,4-triazol-3-yl) methanamine hydrochloride (24 mg, 0.114 mmol). The Reaction mixture was stirred for 16 h at room temperature. After completion of reaction, the mixture was quenched with water and extracted with dichloromethane (2×50 mL). The combined organic layer was washed with brine (50 mL) and dried over sodium sulfate. The organic layer was concentrated under reduced pressure to afford the crude product as red liquid. The crude product was purified by flash chromatography by using ethyl acetate and hexane as eluting agents to afford 2-(4,4-difluoropiperidin-1-yl)-N-((5-(thiophen-2-yl)-1H-,2,4-triazol-3-yl)methyl)benzamide as off-white solid (10 mg, 25%). $^1$H NMR (400 MHz, DMSO-$d_6$) δ 14.35 (s, 0.4H), 13.97 (s, 0.6H), 9.81 (s, 0.4H), 9.73 (s, 0.6H), 7.87-7.66 (m, 2H), 7.53 (dd, J=11.5, 4.2 Hz, 1H), 7.46 (t, J=7.7 Hz, 1H), 7.30 (t, J=7.6 Hz, 1H), 7.19 (dd, J=13.9, 6.4 Hz, 1H), 7.14-7.07 (m, 1H), 4.66 (d, J=5.6 Hz, 1.2H), 4.57 (d, J=5.0 Hz, 0.8H), 3.04 (s, 4H), 2.15 (s, 4H). LC-MS m/z (M+H): 404.1.

The following compounds in Table 4 were prepared using similar procedures to those described above for Compound 76 using the appropriate starting materials.

TABLE 4

| Example/Compound Nos. | Structure | LC-MS [M + H]+ (m/z) | NMR Data |
|---|---|---|---|
| 65 | 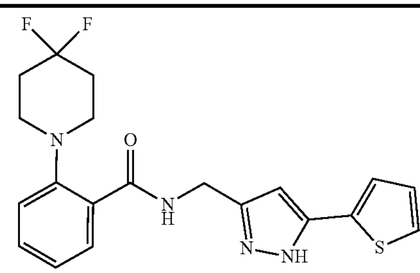 | 402.9 | $^1$H NMR (400 MHz, DMSO-$d_6$) δ 13.18 (s, 0.4H), 12.77 (s, 0.6H), 9.54 (s, 0.4H), 9.39 (s, 0.6H), 7.81-7.66 (m, 1H), 7.56 (s, 0.4H), 7.42 (dd, J = 14.6, 7.9 Hz, 2H), 7.31 (s, 0.6H), 7.24 (d, J = 7.7 Hz, 1H), 7.21-7.14 (m, 1H), 7.12 (s, 0.6H), 7.04 (s, 1H), 6.50 (s, 0.6H), 6.47 (s, 0.4H), 4.54 (d, J = 5.0 Hz, 1.2H), 4.47 (s, 0.8H), 2.99 (s, 4H), 1.96 (s, 4H) |
| 66 | 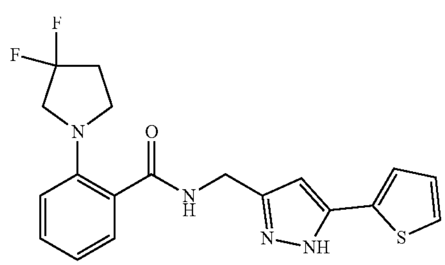 [SMILES: O=C(NCc1cc(-c2cccs2)[nH]n1)c1ccccc1N1CCC(F)(F)C1] | 388.9 | $^1$H NMR (400 MHz, DMSO-$d_6$) δ 13.09 (s, 0.3H), 12.75 (s, 0.7H), 8.87 (s, 1H), 7.62-7.18 (m, 4H), 7.05 (s, 1H), 6.81 (s, 2H), 6.46 (s, 1H), 4.44 (s, 2H), 3.54 (t, J = 13.0 Hz, 2H), 3.39 (s, 2H), 2.39 (s, 2H). |
| 67 | 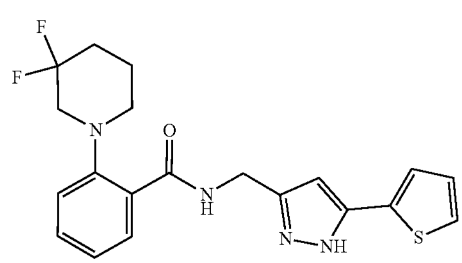 [SMILES: O=C(NCc1cc(-c2cccs2)[nH]n1)c1ccccc1N1CCCC(F)(F)C1] | 403.9 | $^1$H NMR (400 MHz, DMSO-$d_6$) δ 13.94 (s, 1H), 10.05 (s, 1H), 7.89 (d, J = 7.5 Hz, 1H), 7.75-7.44 (m, 3H), 7.36 (d, J = 7.9 Hz, 1H), 7.25 (t, J = 7.4 Hz, 1H), 7.13 (s, 1H), 4.60 (s, 2H), 3.26 (t, J = 11.3 Hz, 2H), 2.94 (s, 2H), 1.96 (s, 2H), 1.80 (s, 2H) |

TABLE 4-continued

| Example/ Compound Nos. | Structure | LC-MS [M + H]+ (m/z) | NMR Data |
|---|---|---|---|
| 72 | 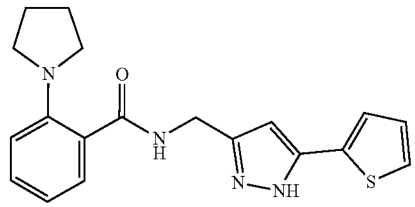 [SMILES: O=C(NCc1cc(-c2cccs2)[nH]n1)c1ccccc1N1CCCC1] | 353.2 | |
| 73 | 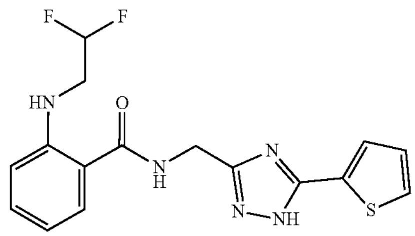 [SMILES: O=C(NCc1n[nH]c(-c2cccs2)n1)c1ccccc1NCC(F)F] | 363.9 | ¹H NMR (400 MHz, DMSO-d₆) δ 14.07 (s, 1H), 9.05 (s, 1H), 8.15 (s, 1H), 7.62 (d, J = 60.6 Hz, 3H), 7.31 (t, J = 7.5 Hz, 1H), 7.12 (s, 1H), 6.85 (d, J = 8.4 Hz, 1H), 6.65 (t, J = 7.2 Hz, 1H), 6.16 (t, J = 55.9 Hz, 1H), 4.53 (s, 2H), 3.63 (t, J = 15.5 Hz, 2H). |
| 74 | 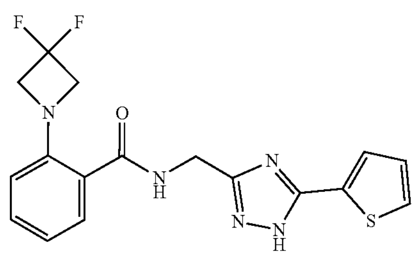 [SMILES: O=C(NCc1n[nH]c(-c2cccs2)n1)c1ccccc1N1CC(F)(F)C1] | 375.9 | ¹H NMR (400 MHz, DMSO-d₆) δ 14.09 (s, 1H), 8.96 (s, 1H), 7.55 (s, 2H), 7.42-7.22 (m, 2H), 7.13 (s, 1H), 6.84 (t, J = 7.2 Hz, 1H), 6.59 (d, J = 8.1 Hz, 1H), 4.51 (s, 2H), 4.21 (t, J = 11.8 Hz, 4H) |
| 75 | 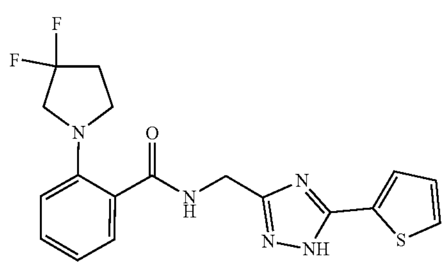 [SMILES: O=C(NCc1n[nH]c(-c2cccs2)n1)c1ccccc1N1CCC(F)(F)C1] | 389.9 | ¹H NMR (400 MHz, DMSO-d₆) δ 14.25 (s, 0.4H), 13.95 (s, 0.6H), 8.98 (d, J = 44.8 Hz, 1H), 7.68-7.54 (m, 2H), 7.34-7.27 (m, 2H), 7.12 (s, 1H), 6.91-6.66 (m, 2H), 4.53 (s, 2H), 3.56 (t, J = 13.1 Hz, 2H), 3.41 (s, 2H), 2.43-2.25 (m, 2H) |
| 77 | 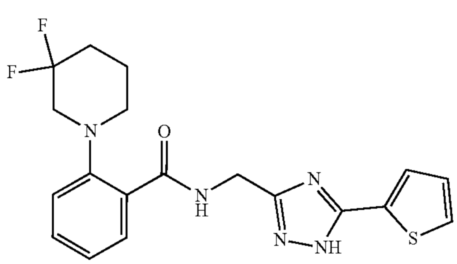 [SMILES: O=C(NCc1n[nH]c(-c2cccs2)n1)c1ccccc1N1CCCC(F)(F)C1] | 403.14 | ¹H NMR (400 MHz, DMSO-d₆) δ 12.93 (s, 1H), 9.66 (d, J = 61.3 Hz, 1H), 7.82 (d, J = 7.6 Hz, 1H), 7.48 (t, J = 7.0 Hz, 1H), 7.38 (s, 1H), 7.32 (d, J = 7.8 Hz, 2H), 7.23 (t, J = 7.4 Hz, 1H), 7.04 (s, 1H), 6.47 (s, 1H), 4.51 (s, 2H), 3.24 (t, J = 11.3 Hz, 2H), 2.90 (s, 2H), 2.06-1.86 (m, 2H), 1.66 (s, 2H) |

TABLE 4-continued

| Example/ Compound Nos. | Structure | LC-MS [M + H]+ (m/z) | NMR Data |
|---|---|---|---|
| 78 | 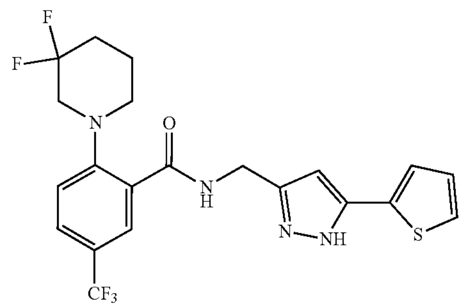 [SMILES: O=C(NCc1cc(-c2cccs2)[nH]n1)c1cc(C(F)(F)F)ccc1N1CCCC(F)(F)C1] | 471.2 | |
| 79 | 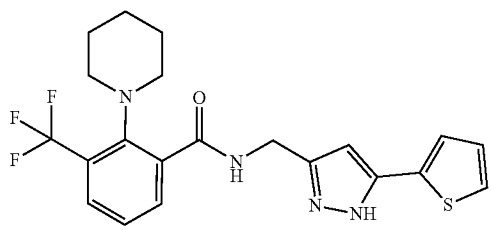 [SMILES: O=C(NCc1cc(-c2cccs2)[nH]n1)c1cccc(C(F)(F)F)c1N1CCCCC1] | 435.2 | |
| 81 | 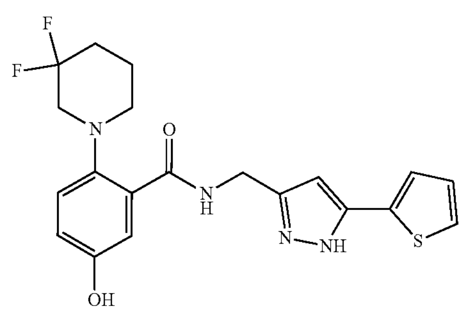 [SMILES: O=C(NCc1cc(-c2cccs2)[nH]n1)c1cc(O)ccc1N1CCCC(F)(F)C1] | 419.2 | |
| 82 | 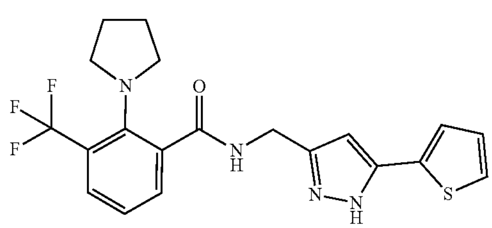 [SMILES: O=C(NCc1cc(-c2cccs2)[nH]n1)c1cccc(C(F)(F)F)c1N1CCCC1] | 421.2 | |
| 83 | 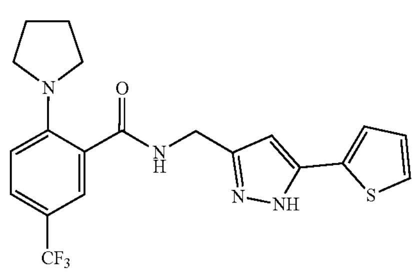 [SMILES: O=C(NCc1cc(-c2cccs2)[nH]n1)c1cc(C(F)(F)F)ccc1N1CCCC1] | 421.2 | |

TABLE 4-continued

| Example/ Compound Nos. | Structure | LC-MS [M + H]+ (m/z) | NMR Data |
|---|---|---|---|
| 84 | 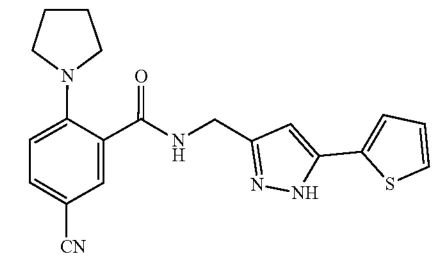 [SMILES: N#Cc1ccc(N2CCCC2)c(C(=O)NCc2cc(-c3cccs3)[nH]n2)c1] | 378.2 | |
| 85 | 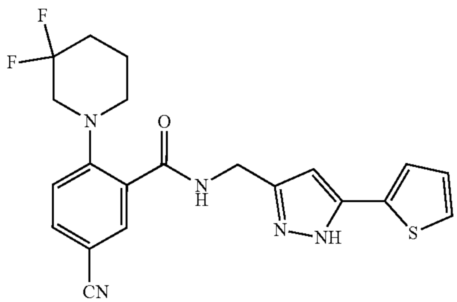 [SMILES: N#Cc1ccc(N2CCCC(F)(F)C2)c(C(=O)NCc2cc(-c3cccs3)[nH]n2)c1] | 428.2 | |
| 92 | 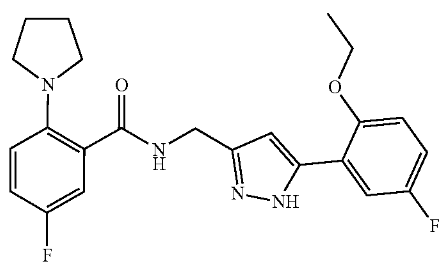 [SMILES: CCOc1ccc(F)cc1-c1cc(CNC(=O)c2cc(F)ccc2N2CCCC2)n[nH]1] | 427.2 | |
| 93 | 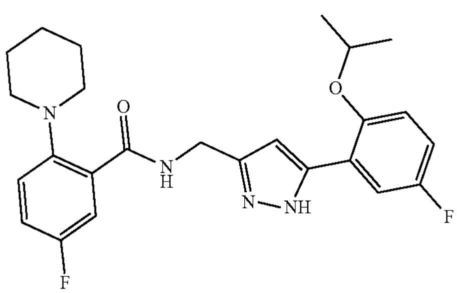 [SMILES: CC(C)Oc1ccc(F)cc1-c1cc(CNC(=O)c2cc(F)ccc2N2CCCCC2)n[nH]1] | 455.3 | |
| 95 | 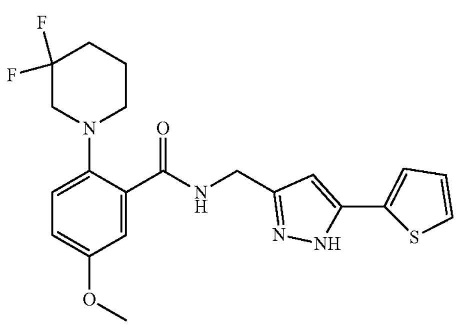 [SMILES: COc1ccc(N2CCCC(F)(F)C2)c(C(=O)NCc2cc(-c3cccs3)[nH]n2)c1] | 432.2 | |

TABLE 4-continued

| Example/ Compound Nos. | Structure | LC-MS [M + H]+ (m/z) | NMR Data |
| --- | --- | --- | --- |
| 96 | 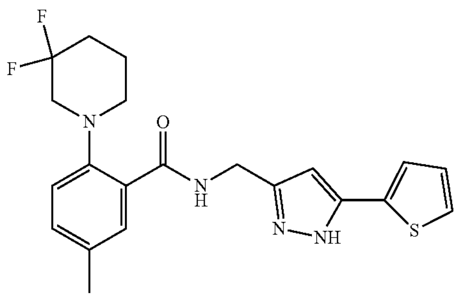 [SMILES: Cc1ccc(N2CCCC(F)(F)C2)c(C(=O)NCc2cc(-c3cccs3)[nH]n2)c1] | 417.2 | |
| 97 | 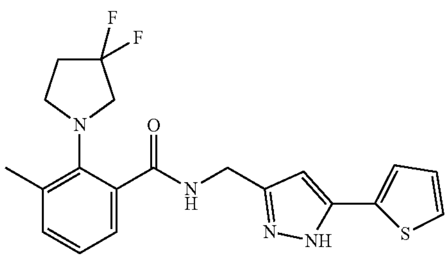 [SMILES: Cc1cccc(C(=O)NCc2cc(-c3cccs3)[nH]n2)c1N1CCC(F)(F)C1] | 403.15 | $^1$H NMR (400 MHz, DMSO) δ 12.93 (s, 1H), 8.95 (s, 1H), 7.40 (s, 1H), 7.36-7.15 (m, 3H), 7.08 (d, J = 22.0 Hz, 2H), 6.45 (d, J = 25.6 Hz, 1H), 4.42 (d, J = 20.9 Hz, 2H), 3.46 (t, J = 12.9 Hz, 2H), 3.26 (s, 2H), 2.28 (d, J = 23.7 Hz, 5H) |
| 98 | 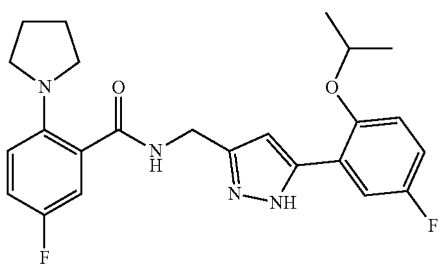 [SMILES: CC(C)Oc1ccc(F)cc1-c1cc(CNC(=O)c2cc(F)ccc2N2CCCC2)n[nH]1] | 441.3 | |
| 99 | 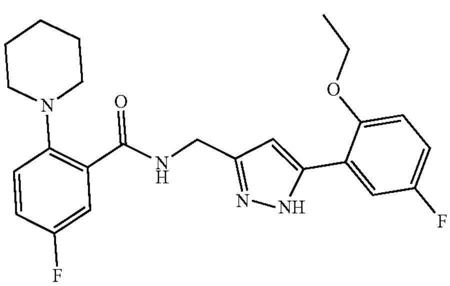 [SMILES: CCOc1ccc(F)cc1-c1cc(CNC(=O)c2cc(F)ccc2N2CCCCC2)n[nH]1] | 441.3 | |
| 101 | 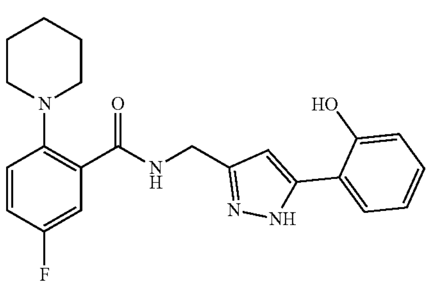 [SMILES: O=C(NCc1cc(-c2ccccc2O)[nH]n1)c1cc(F)ccc1N1CCCCC1] | 395.3 | |

TABLE 4-continued

| Example/ Compound Nos. | Structure | LC-MS [M + H]+ (m/z) | NMR Data |
|---|---|---|---|
| 104 | 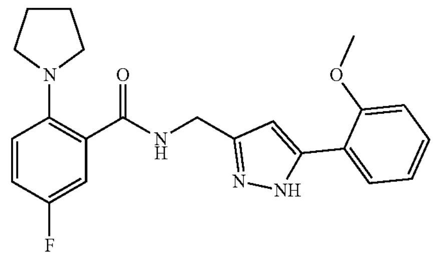 [SMILES: COc1ccccc1-c1cc(CNC(=O)c2cc(F)ccc2N2CCCC2)n[nH]1] | 395.2 | |
| 105 | 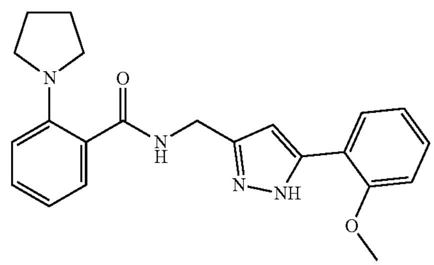 [SMILES: COc1ccccc1-c1cc(CNC(=O)c2ccccc2N2CCCC2)n[nH]1] | 377.2 | |
| 106 | 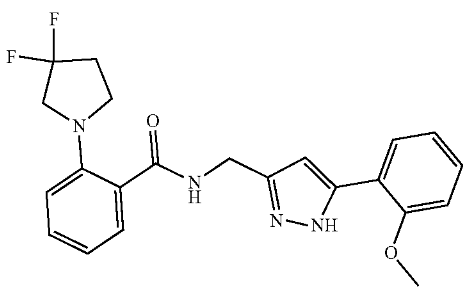 [SMILES: COc1ccccc1-c1cc(CNC(=O)c2ccccc2N2CCC(F)(F)C2)n[nH]1] | 413.2 | |
| 107 | 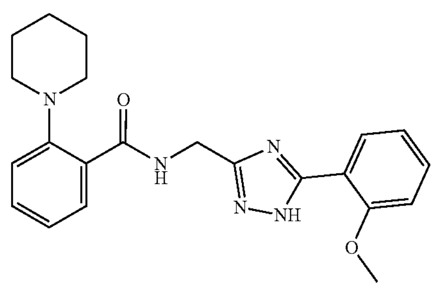 [SMILES: COc1ccccc1-c1nc(CNC(=O)c2ccccc2N2CCCCC2)n[nH]1] | 392.2 | |
| 108 | 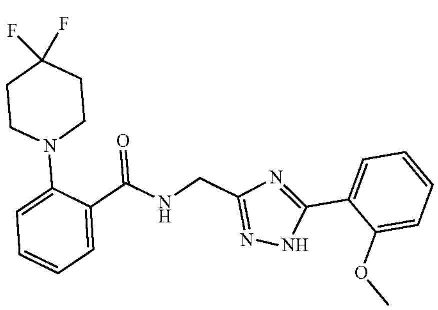 [SMILES: COc1ccccc1-c1nc(CNC(=O)c2ccccc2N2CCC(F)(F)CC2)n[nH]1] | 428.2 | |

TABLE 4-continued
| Example/ Compound Nos. | Structure | LC-MS [M + H]+ (m/z) | NMR Data |
|---|---|---|---|
| 109 | 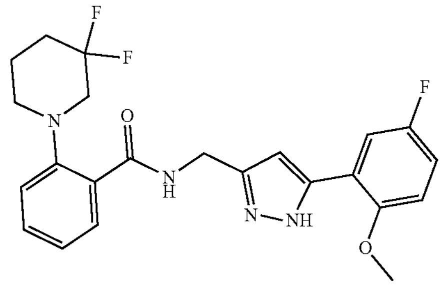 [SMILES: COc1ccc(F)cc1-c1cc(CNC(=O)c2ccccc2N2CCCC(F)(F)C2)n[nH]1] | 445.1 | |
| 111 | 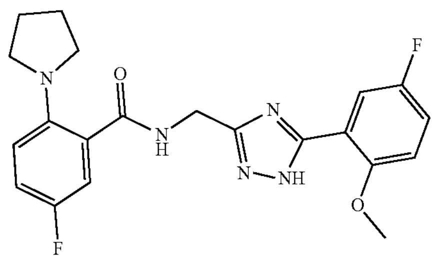 [SMILES: COc1ccc(F)cc1-c1nc(CNC(=O)c2cc(F)ccc2N2CCCC2)n[nH]1] | 414.2 | |
| 112 | 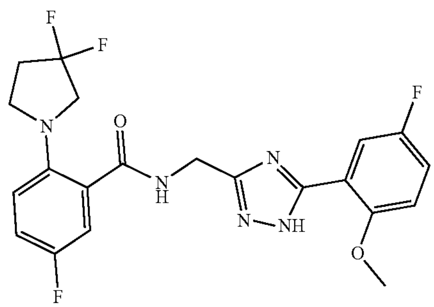 [SMILES: COc1ccc(F)cc1-c1nc(CNC(=O)c2cc(F)ccc2N2CCC(F)(F)C2)n[nH]1] | 450.1 | |
Synthesis of 3-(3,3-difluoropyrrolidin-1-yl)-N-((5-(thiophen-2-yl)-1H-1,2,4-triazol-3-yl) methyl) pyrazine-2-carboxamide (Compound 87)
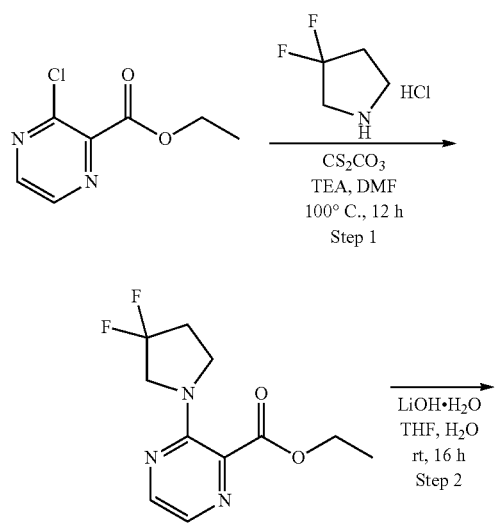
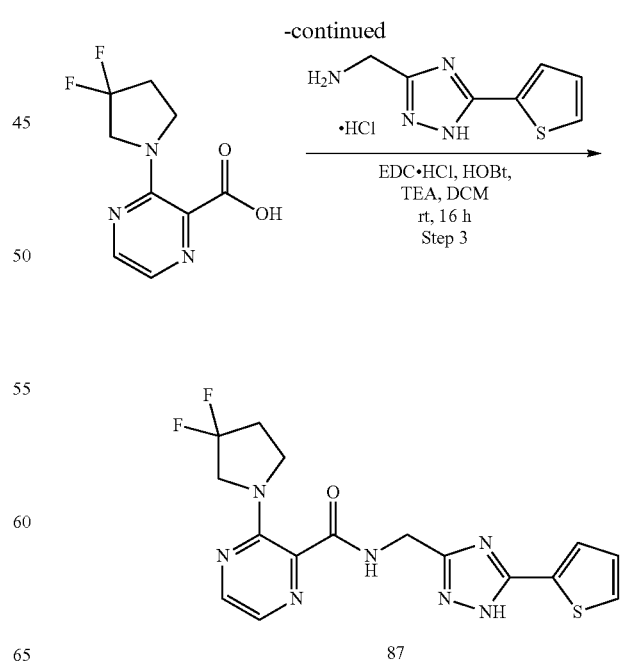
-continued

Step 1: Synthesis of ethyl 3-(3,3-difluoropyrrolidin-1-yl) pyrazine-2-carboxylate

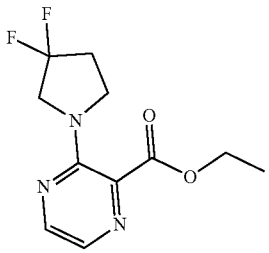 [SMILES: CCOC(=O)c1nccnc1N1CCC(F)(F)C1]

To a stirred to solution of ethyl 3-chloropyrazine-2-carboxylate (300 mg, 1.61 mmol) in DMF (10 ml) at 0° C. was added $CS_2CO_3$ (1.2 g, 3.22 mmol) and $Et_3N$ (162.9 mg, 1.61 mmol) followed by 3,3-difluoropyrolidine.HCl (277.9 mg, 1.93 mmol). The reaction mixture was stirred at 100° C. for 12 h in a sealed tube. After the completion of the reaction, the reaction mixture was diluted with water and extracted with EtOAc (3×20 mL). The combined organic layer was dried over anhydrous $Na_2SO_4$ and concentrated under vacuum. The crude product was triturated with n-hexane and the resultant product dried to afford ethyl 3-(3,3-difluoropyrrolidin-1-yl) pyrazine-2-carboxylate as yellow syrup (260 mg, 62.95%). H NMR (400 MHz, DMSO-d$_6$) δ 8.23 (d, J=2 Hz, 1H), 8.03 (d, J=2 Hz, 1H), 4.50 (q, J=6.4 Hz, 2H), 3.78-3.72 (m, 4H), 2.51-2.40 (m, 2H), 1.46 (t, J=6.8 Hz, 3H).

Step 2: Synthesis of 3-(3,3-difluoropyrrolidin-1-yl) pyrazine-2-carboxylic acid

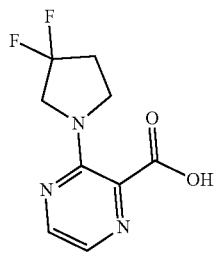 [SMILES: O=C(O)c1nccnc1N1CCC(F)(F)C1]

To a stirred solution of ethyl 3-(3,3-difluoropyrrolidin-1-yl) pyrazine-2-carboxylate (250 mg, 0.97 mmol) in THF: $H_2O$ (5 mL:2 mL) at 0° C. was added LiOH (244.67 mg, 5.83 mmol). The reaction mixture was stirred at room temperature for 12 h. After the completion of reaction the reaction mixture was acidified with 1N HCl and extracted with EtOAc (2×20 mL), the organic layer was dried over $MgSO_4$ and concentrated under vacuum, to afford the 3-(3,3-difluoropyrrolidin-1-yl) pyrazine-2-carboxylic acid as a off-white solid. (200 mg, 90.17%). $^1$H NMR (400 MHz, DMSO-d$_6$): δ 13.50 (s, 1H), 8.28 (d, J=2.4 Hz, 1H), 7.97 (s, 1H), 3.80 (t, J=12.8 Hz, 2H), 3.62 (t, J=7.2 Hz, 2H), 2.56-2.49 (m, 2H).

Step 3: Synthesis of 3-(3,3-difluoropyrrolidin-1-yl)-N-((5-(thiophen-2-yl)-1H-1,2,4-triazol-3-yl) methyl) pyrazine-2-carboxamide

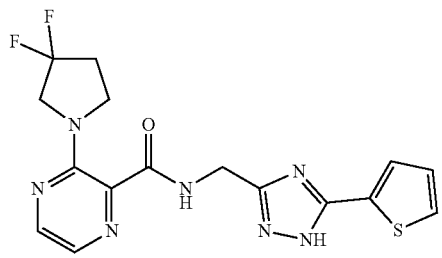 [SMILES: O=C(NCc1n[nH]c(-c2cccs2)n1)c1nccnc1N1CCC(F)(F)C1]

To a stirred solution of 3-((3,3-difluoropyrrolidin-1-yl) methyl) pyrazine-2-carboxylic acid (70 mg, 0.30 mmol) in $CH_2Cl_2$ (10 ml), were added EDC.HCl (87.57 mg, 0.45 mmol), HOBt (61.8 mg, 0.45 mmol) and $Et_3N$ (92.62 mg, 0.91 mmol) at 0° C. The resulting mixture was stirred for 10 min, and then (5-(thiophen-2-yl)-1H-1,2,4-triazol-3-yl) methanamine. HCl (72.62 mg, 0.33 mmol) was added and the reaction mixture was stirred at room temperature for 12 h. After the completion of the reaction, reaction mixture was washed with water and extracted with $CH_2Cl_2$ (2×10 mL). The organic layer was dried over $MgSO_4$ and concentrated under vacuum. The crude product was purified by preparative HPLC to afford the 3-(3,3-difluoropyrrolidin-1-yl)-N-((5-(thiophen-2-yl)-1H-1,2,4-triazol-3-yl) methyl) pyrazine-2-carboxamide as off-white solid (39 mg, 32.63%).1H NMR (400 MHz, DMSO-d$_6$): δ 13.96 (brs, 1H), 9.26 (brs, 1H), 8.26 (s, 1H), 7.94 (s, 1H), 7.59 (d, J=12 Hz, 2H), 7.14 (s, 1H), 4.55 (d, J=5.6 Hz, 2H), 3.80 (t, J=13.2 Hz, 2H), 3.66 (t, J=11.2 Hz, 2H), 2.49-2.39 (m, 2H). LC-MS (m/z): 391.10 (M+H)$^+$ The following compounds in Table 5 were prepared using similar procedures to those described above for Compound 87 using the appropriate starting materials.

TABLE 5

| Example/Compound Nos. | Structure | LC-MS [M + H]+ (m/z) | NMR Data |
|---|---|---|---|
| 86 | 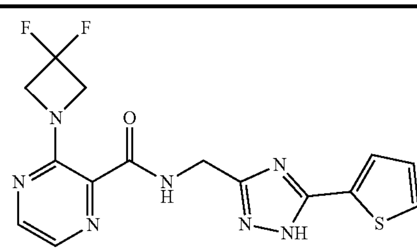 | 377.9 | $^1$H NMR (400 MHz, DMSO-d$_6$) δ 13.85 (s, 1H), 9.25 (s, 1H), 8.37 (s, 1H), 8.08 (s, 1H), 7.56 (s, 2H), 7.13 (s, 1H), 4.56 (s, 2H), 4.45 (t, J = 12.7 Hz, 4H). |

TABLE 5-continued
| Example/ Compound Nos. | Structure | LC-MS [M + H]+ (m/z) | NMR Data |
|---|---|---|---|
| 88 | 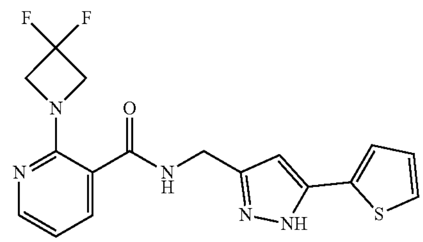 [SMILES: O=C(NCc1cc(-c2cccs2)[nH]n1)c1cccnc1N1CC(F)(F)C1] | 375.9 | ¹H NMR (400 MHz, DMSO-d₆) δ 12.95 (s, 1H), 8.94 (s, 1H), 8.23 (s, 1H), 7.72 (s, 1H), 7.36 (d, J = 26.7 Hz, 1H), 7.05 (s, 1H), 6.86 (d, J = 5.2 Hz, 1H), 6.51 (s, 1H), 4.45 (s, 2H), 4.27 (t, J = 12.6 Hz, 4H) |
| 89 | 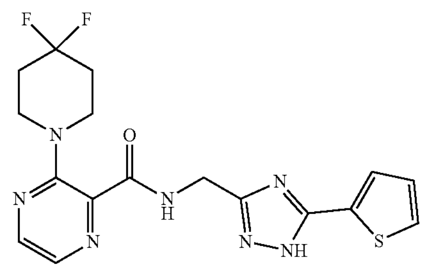 [SMILES: O=C(NCc1n[nH]c(-c2cccs2)n1)c1nccnc1N1CCC(F)(F)CC1] | 405.9 | ¹H NMR (400 MHz, DMSO-d₆) δ 14.10 (s, 1H), 9.25 (d, J = 75.4 Hz, 1H), 8.25 (s, 1H), 8.00 (s, 1H), 7.85-7.39 (m, 2H), 7.12 (s, 1H), 4.55 (s, 2H), 3.51 (s, 4H), 1.85 (d, J = 87.0 Hz, 4H). |
| 90 | 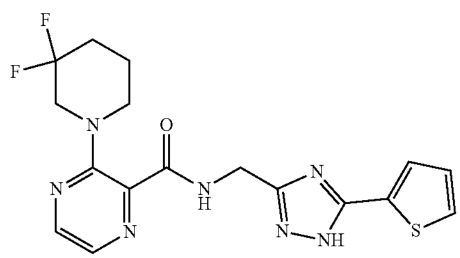 [SMILES: O=C(NCc1n[nH]c(-c2cccs2)n1)c1nccnc1N1CCCC(F)(F)C1] | 405.9 | ¹H NMR (400 MHz, DMSO-d₆) δ 14.02 (s, 1H), 9.29 (s, 1H), 8.24 (s, 1H), 7.99 (s, 1H), 7.58 (s, 2H), 7.14 (s, 1H), 4.53 (s, 2H), 3.72 (t, J = 12.1 Hz, 2H), 3.40 (d, J = 42.2 Hz, 2H), 2.00 (d, J = 20.1 Hz, 2H), 1.68 (s, 2H). |
Synthesis of N-((5-(4-methylthiophen-3-yl)-1H-pyrazol-3-yl) methyl)-2-(trifluoro methoxy) benzamide (Compound 16)
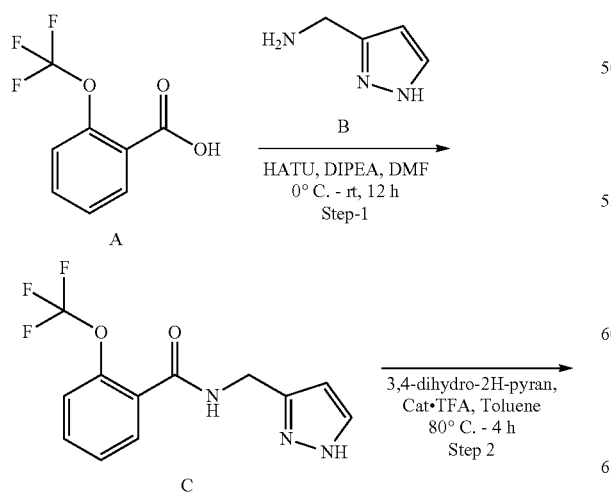
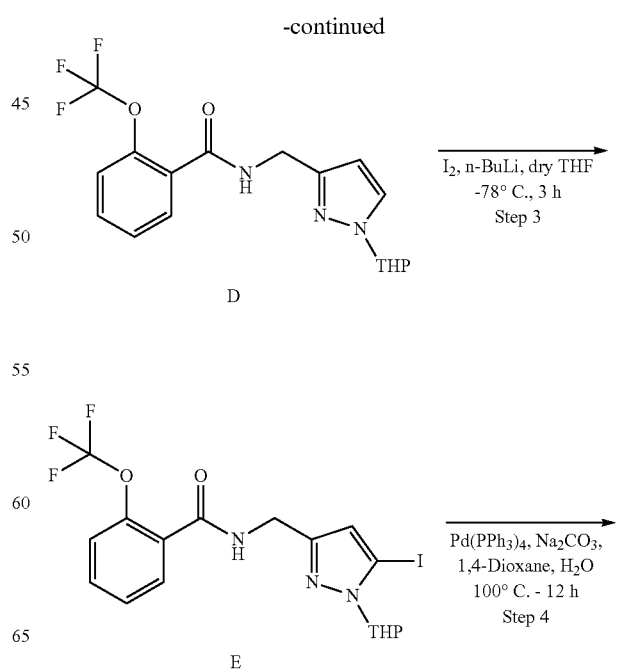

-continued

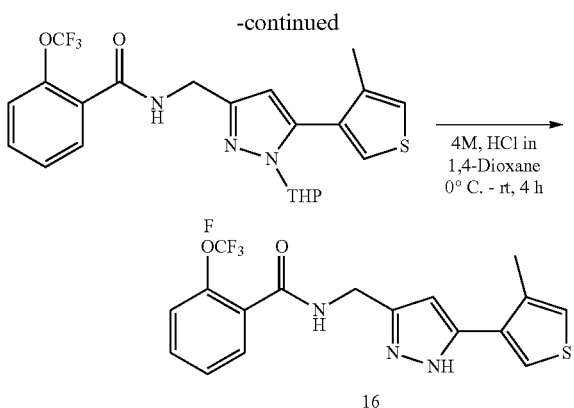

16

Step 1: N-((1H-pyrazol-3-yl) methyl)-2-(trifluoro methoxy) benzamide

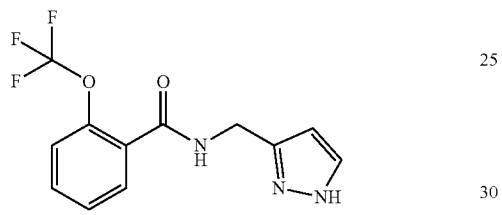

To a stirred solution of 2-(trifluoromethoxy) benzoic acid (25 g, 0.121 mmol) in DMF (250 mL) at 0° C. was added HATU (46.1 g, 0.121), followed by (2H-pyrazol-3-yl) methanamine (11.7 g, 0.1213) and DIPEA (39.1 g, 0.303 mmol). The reaction mixture was then stirred at room temperature for 12 h. After the completion of reaction, the reaction mixture was diluted with water (2.5 L) and extracted with EtOAc (2×500 mL). The combined organic layer was washed once with H$_2$O (250 mL), saturated NaHCO$_3$ solution (250 mL), and finally with brine (250 mL). The organic layer was dried over Na$_2$SO$_4$, concentrated to get the crude compound. The crude compound was purified by flash column chromatography (eluent: 70% EtOAc/Pet ether) to afford N-((1H-pyrazol-3-yl) methyl)-2-(trifluoro methoxy) benzamide (18.3 g, 53.0% Yield) as off white solid $^1$H NMR (400 MHz, DMSO) δ 12.64 (d, J=47.1 Hz, 1H), 8.87 (d, J=42.1 Hz, 1H), 7.76-7.50 (m, 3H), 7.49-7.27 (m, 2H), 6.15 (d, J=12.1 Hz, 1H), 4.42 (t, J=11.1 Hz, 2H). LC-MS m/z (M+H): 286.1.

Step 2: N-((1-(tetrahydro-2H-pyran-2-yl)-1H-pyrazol-3-yl) methyl)-2-(trifluoro methoxy) benzamide

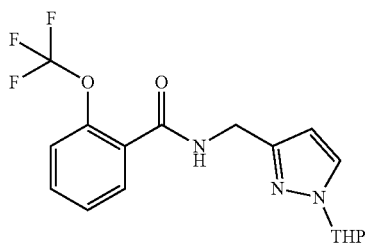

To a stirred solution of N-((1H-pyrazol-3-yl) methyl)-2-(trifluoro methoxy) benzamide (18.3 g, 64.15 mmol) in toluene (400 mL) at room temperature was added 3, 4-dihydro-2H-pyran (5.39 g, 64.1 mmol). Then the reaction was heated at 80° C. for 4 h. After the completion of reaction, the solvent toluene was distilled off and the residue was diluted with EtOAc (250 mL), washed once with saturated NaHCO$_3$ solution (100 mL) and H$_2$O (100 mL). The organic layer was separated, dried over Na$_2$SO$_4$ and concentrated to get the crude compound. The crude product thus obtained was triturated with petroleum ether (200 mL) and stirred for 12 h. The solids were filtered and dried under vacuum to afford N-((1-(tetrahydro-2H-pyran-2-yl)-1H-pyrazol-3-yl) methyl)-2-(trifluoro methoxy) benzamide (12.57 g, 51.5%) as off white solid. $^1$H NMR (400 MHz, DMSO) δ 8.87 (s, 1H), 7.80 (d, J=2.2 Hz, 1H), 7.57 (t, J=7.0 Hz, 2H), 7.46-7.38 (m, 2H), 6.20 (d, J=2.2 Hz, 1H), 5.32 (d, J=10.3 Hz, 1H), 4.38 (d, J=5.9 Hz, 2H), 3.90 (d, J=11.0 Hz, 1H), 3.67-3.52 (m, 1H), 2.07 (dd, J=24.7, 11.0 Hz, 1H), 1.98-1.80 (m, 2H), 1.65 (s, 1H), 1.51 (d, J=3.5 Hz, 2H). LC-MS m/z (M+H): 370.1.

Step 3: N-((5-iodo-1-(tetrahydro-2H-pyran-2-yl)-1H-pyrazol-3-yl) methyl)-2-(trifluoro methoxy) benzamide

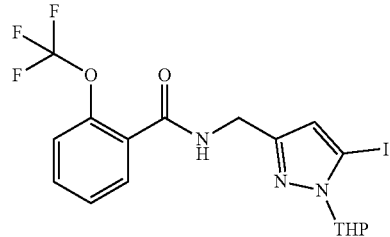

To a stirred solution of N-((1-(tetrahydro-2H-pyran-2-yl)-1H-pyrazol-3-yl) methyl)-2-(trifluoro methoxy) benzamide (18.2 g, 49.30 mmol) in dry THF (200 mL) at −78° C. was added 1.6M n-Butyl lithium in hexane (6.31 g, 98.61 mmol) over a period of 10 min. Then the reaction mixture was stirred at same temperature for 1 h. To the resultant mixture was added iodine (13.76 g, 54.2 mmol) in dry THF (200 mL) over 15 min. After the completion of addition of iodine, the reaction was slowly allowed to warm up to −20° C. and stirred for 45 min. After the completion of the reaction, it was quenched carefully with saturated NaHSO$_3$ solution (200 mL) and extracted with EtOAc (2×150 mL). The combined organic layer was dried over Na$_2$SO$_4$ and concentrated to get the crude compound. The crude compound was purified by flash column chromatography (eluent: 20% EtOAc in petroleum ether) to N-((5-iodo-1-(tetrahydro-2H-pyran-2-yl)-1H-pyrazol-3-yl) methyl)-2-(trifluoro methoxy) benzamide (12.57 g, 51.5%) as off white solid. $^1$H NMR (400 MHz, DMSO) δ 8.91 (t, J=5.6 Hz, 1H), 7.63-7.53 (m, 2H), 7.44 (dd, J=14.6, 7.6 Hz, 2H), 6.43 (s, 1H), 5.33 (d, J=9.8 Hz, 1H), 4.36 (d, J=5.6 Hz, 2H), 3.90 (d, J=10.9 Hz, 1H), 3.59 (dd, J=17.3, 7.5 Hz, 1H), 2.27 (dd, J=22.8, 9.5 Hz, 1H), 1.97 (d, J=12.3 Hz, 1H), 1.83 (d, J=12.1 Hz, 1H), 1.67 (s, 1H), 1.50 (s, 2H), LC-MS m/z (M+H): 396.0.

Step 4: N-((5-(4-methylthiophen-3-yl)-1-(tetrahydro-2H-pyran-2-yl)-1H-pyrazol-3-yl) methyl)-2-(trifluoro methoxy) benzamide

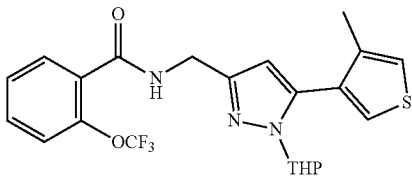

To a stirred solution of N-((5-iodo-1-(tetrahydro-2H-pyran-2-yl)-1H-pyrazol-3-yl) methyl)-2-(trifluoro methoxy) benzamide (60 mg, 0.131 mmol) and 4-methyl thiphene-3-boronic acid (20.66 mg, 0.157 mmol) in 1,4-dioxane:water (5 mL:1 mL) was added Na$_2$CO$_3$ (34.71 mg, 0.327 mmol). Then the reaction mixture was degassed with argon for 10 min followed by the addition of palladium-tetrakis(triphenylphosphine) (15.13 mg, 0.0130 mmol). The resultant mixture was heated at 100° C. for 12 h. After the completion of reaction, the mixture was diluted with H$_2$O (5 mL) and extracted with EtOAc (2×10 mL). The combined organic layer was dried over Na$_2$SO$_4$ and concentrated to get the crude compound. It was further purified by preparative TLC to afford N-((5-(4-methylthiophen-3-yl)-1-(tetrahydro-2H-pyran-2-yl)-1H-pyrazol-3-yl) methyl)-2-(trifluoro methoxy) benzamide (34 mg, 57.74%) as off-white solid. $^1$H NMR (400 MHz, DMSO) δ 8.93 (s, 1H), 7.57 (dd, J=15.8, 5.4 Hz, 3H), 7.44 (dd, J=15.6, 7.6 Hz, 2H), 7.34 (s, 1H), 6.26 (s, 1H), 5.02 (d, J=9.5 Hz, 1H), 4.43 (s, 2H), 3.91 (d, J=11.1 Hz, 1H), 3.43 (s, 1H), 2.33 (d, J=14.2 Hz, 1H), 2.09 (d, J=16.3 Hz, 3H), 1.90 (s, 1H), 1.47 (s, 3H), 1.22 (s, 2H). LC-MS m/z (M+H): 466.2.

The following intermediate compounds in Table 6 were prepared using similar procedures to those described above for Compound 16 using the appropriate starting materials.

TABLE 6

| Structure | LC-MS [M + H]+ (m/z) | NMR Data |
|---|---|---|
| 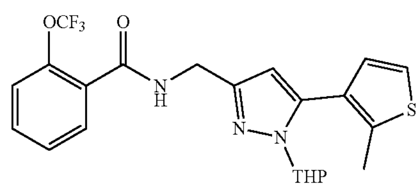 | 466.1 | |
| | 486.1 | $^1$H NMR (400 MHz, DMSO) δ 8.92 (s, 1H), 7.56-7.60 (m, 3H), 7.41-7.46 (m, 2H), 7.28 (s, 1H), 6.40 (s, 1H), 5.26 (d, J = 8.0 Hz, 1H), 4.33-4.45 (m, 2H), 3.92 (d, J = 12.8 Hz, 1H), 3.60-3.62 (m, 2H), 2.31-2.36 (m, 1H), 1.95(d, J = 12.8 Hz, 1H), 1.85(d, J = 16 Hz, 1H), 1.62 (brs, 1H), 1.52 (brs, 2H). |
| | 486.1 | $^1$H NMR (400 MHz, DMSO) δ 8.96 (s, 1H), 7.65 (d, J = 5.6 Hz, 1H), 7.57 (t, J = 7.4 Hz, 2H), 7.44 (dd, J = 15.9, 8.0 Hz, 3H), 7.14 (d, J = 5.3 Hz, 1H), 6.41 (s, 1H), 5.08 (d, J = 10.8 Hz, 1H), 4.44 (s, 1H), 3.91 (d, J = 11.1 Hz, 1H), 3.45 (s, 1H), 2.31 (s, 1H), 1.91 (s, 1H), 1.81 (d, J = 12.8 Hz, 1H), 1.49 (s, 3H). |
| 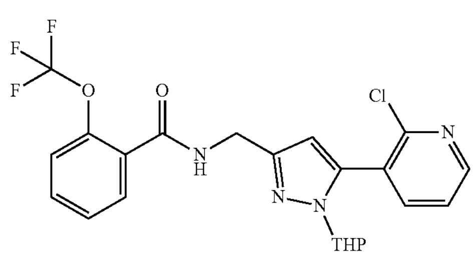 | 396.8 | $^1$H NMR (400 MHz, DMSO-d$_6$) δ 9.00 (s, 1H), 8.52 (d, J = 3.2 Hz, 1H), 7.88 (d, J = 6.0 Hz, 1H), 7.55-7.57 (m, 3H), 7.40-7.46 (m, 2H), 6.39 (s, 1H), 4.96 (d, J = 8.4 Hz, 1H), 4.44 (d, J = 5.6 Hz, 2H), 3.98-4.04 (m, 1H), 3.77 (d, J = 11.2 Hz, 1H), 3.32 (s, 1H), 2.27-2.30 (m, 1H), 1.82-1.97 (m, 3H), 1.43-1.55 (m, 3H), 1.16 (t, J = 6.8 Hz, 1H) |

TABLE 6-continued

| Structure | LC-MS [M + H]+ (m/z) | NMR Data |
|---|---|---|
| 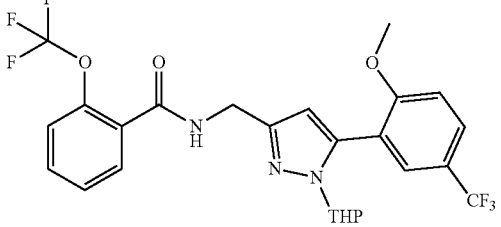 | 543.8 | $^1$H NMR (400 MHz, DMSO-d$_6$) δ 8.95 (t, J = 5.2 Hz, 1H), 7.82 (d, J = 8.4 Hz, 1H), 7.55-7.62 (m, 4H), 7.40-7.46 (m, 2H), 7.34 (d, J = 8.8 Hz, 1H), 6.32 (s, 1H), 4.92 (d, J = 9.6 Hz, 1H), 4.37-4.44 (m, 2H), 3.85-3.88 (m, 4H), 3.55(brs, 1H), 2.31 (brs, 1H), 1.89-1.92 (brs, 1H), 1.76(d, J = 13.6 Hz, 1H), 1.45-1.47(m, 4H). |
| 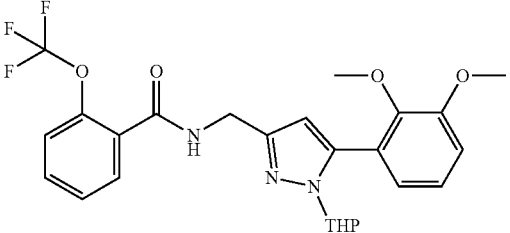 | 485.9 | $^1$H NMR (400 MHz, DMSO-d$_6$) δ 13.03 (s, 1H), 8.87 (s, 1H), 8.19 (s, 1H), 7.85 (d, J = 8.0 Hz, 1H), 7.55-7.64 (m, 4H), 7.40-7.47 (m, 4H), 7.25 (t, J = 7.2 Hz, 1H), 6.57 (s, 1H) |
| 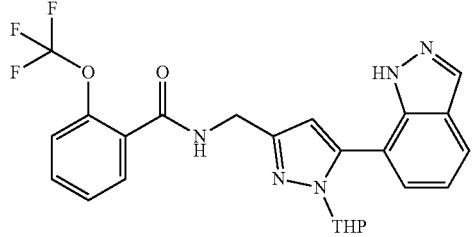 | 505.9 | $^1$H NMR (400 MHz, DMSO-d$_6$) rotamer δ 8.94 (s, 1H), 7.55-7.59 (m, 2H), 7.40-7.46 (m, 2H), 7.15 (d, J = 4.4 Hz, 2H), 6.84 (t, J = 4.8 Hz, 1H), 6.22 (s, 1H), 4.96 (d, J = 8.8 Hz, 1H), 4.43 (d, J = 5.2 Hz, 2H), 4.00-4.02 (m, 1H), 3.84 (s, 4H), 3.52 (s, 3H), 3.32 (s, 1H), 1.75-1.97 (m, 3H), 1.43-1.51 (m, 3H), 1.16 (t, J = 6.8 Hz, 2H) |
| 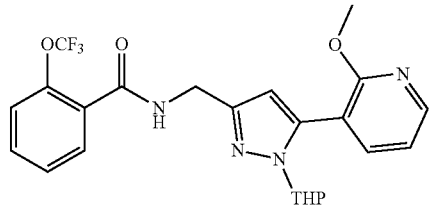 | 476.9 | $^1$H NMR (400 MHz, DMSO-d$_6$) δ 8.99-8.92 (m, 1H), 8.27 (dd, J = 5.0, 2.1 Hz, 1H), 7.70 (dd, J = 7.3, 2.0 Hz, 1H), 7.57 (t, J = 8.4 Hz, 2H), 7.49-7.39 (m, 2H), 7.13 (dd, J = 7.4, 5.0 Hz, 1H), 6.30 (d, J = 2.4 Hz, 1H), 4.97 (dd, J = 10.0, 2.5 Hz, 1H), 4.43 (d, J = 5.9 Hz, 2H), 3.86 (d, J = 2.2 Hz, 4H), 3.42-3.32 (m, 2H), 2.30 (d, J = 12.0 Hz, 1H), 1.91 (s, 1H), 1.80 (d, J = 13.2 Hz, 1H), 1.53 (dd, J = 21.6, 11.5 Hz, 2H), 1.45 (s, 4H), 1.12-1.04 (m, 1H). |
| 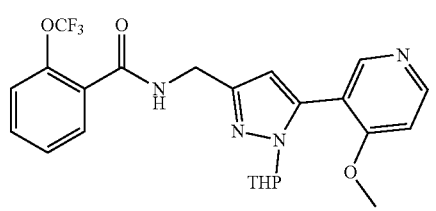 | 477.2 | |
| 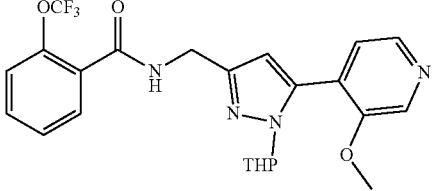 | 477.08 | |

TABLE 6-continued

| Structure | LC-MS [M + H]+ (m/z) | NMR Data |
|---|---|---|
| 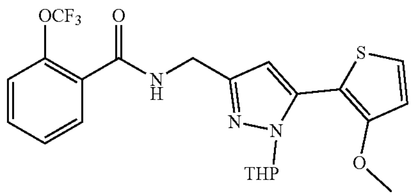 | 481.9 | ¹H NMR (400 MHz, DMSO-d₆) δ 8.92 (s, 1H), 7.65 (d, J = 5.6 Hz, 1H), 7.55-7.56 (m, 3H), 7.40-7.46 (m, 3H), 7.14 (d, J = 5.6 Hz, 1H), 6.33(s, 1H), 5.22 (d, J = 8.8 Hz, 1H), 4.37-4.41 (m, 3H), 3.88-3.91 (m, 1H), 3.381(s, 3H), 3.49 (brs, 1H), 3.14(s, 1H), 1.17-1.93(m, 3H), 1.69 (brs, 1H), 1.49 (brs, 3H). |
| 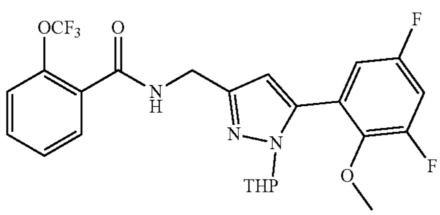 | 511.8 | ¹H NMR (400 MHz, DMSO-d₆) δ 8.95 (brs, 1H), 7.59-7.40 (m, 5H), 7.05 (d, J = 8.4 Hz, 1H), 6.35 (s, 1H), 5.06 (d, J = 9.6 Hz, 1H), 4.44 (d, J = 5.6 Hz, 2H), 3.84 (d, J = 11.6 Hz, 1H), 3.63 (s, 3H), 3.38 (brs, 3H), 2.37 (brs, 1H), 1.97-1.79 (m, 3H), 1.58-1.32 (m, 4H). |
| 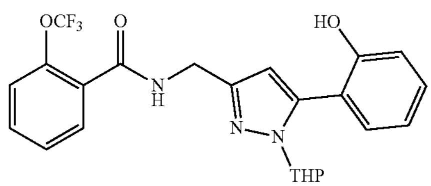 | 461.9 | ¹H NMR (400 MHz, DMSO-d₆) δ 9.82 (s, 1H), 8.94 (d, J = 6.0 Hz, 1H), 7.57 (t, J = 8.1 Hz, 2H), 7.43 (q, J = 7.9 Hz, 2H), 7.25 (t, J = 7.8 Hz, 1H), 7.18 (d, J = 7.5 Hz, 1H), 6.95 (d, J = 8.2 Hz, 1H), 6.88 (t, J = 7.5 Hz, 1H), 6.19 (s, 1H), 5.07 -4.99 (m, 1H), 4.46 -4.35 (m, 2H), 3.85 (d, J = 11.7 Hz, 1H), 1.93 (s, 1H), 1.81 (d, J = 13.2 Hz, 1H), 1.50 (d, J = 8.6 Hz, 2H), 1.46 (d, J = 10.0 Hz, 1H), 1.25-1.12 (m, 3H). |
| 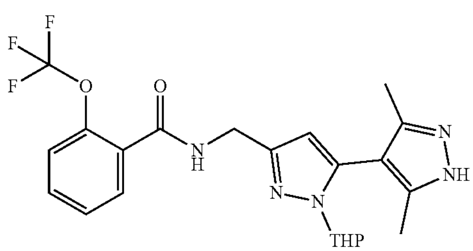 | 463.9 | |
| 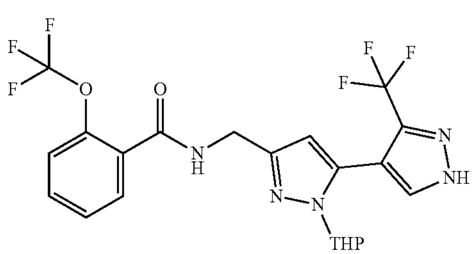 | 503.9 | |
| 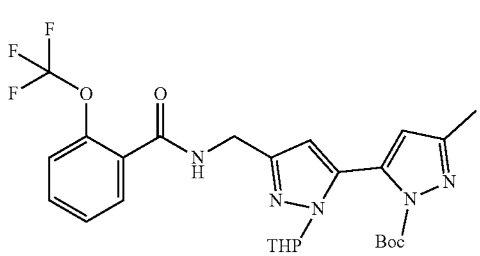 | 449.9 | |

TABLE 6-continued

| Structure | LC-MS [M + H]+ (m/z) | NMR Data |
|---|---|---|
| 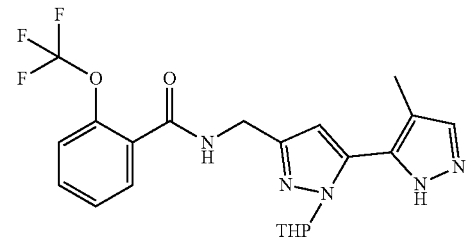 | 449.9 | |
| 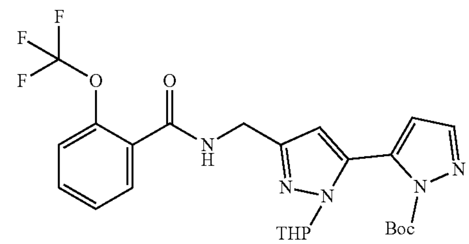 | 435.9 | |
| 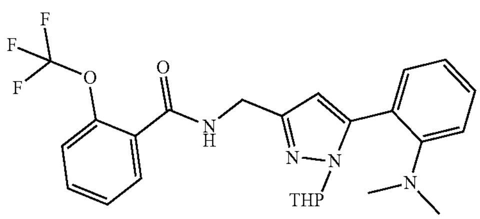 | 488.90 | |
| 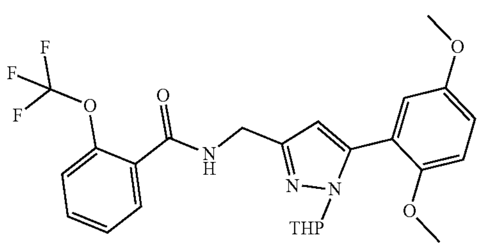 | 505.9 | |
| 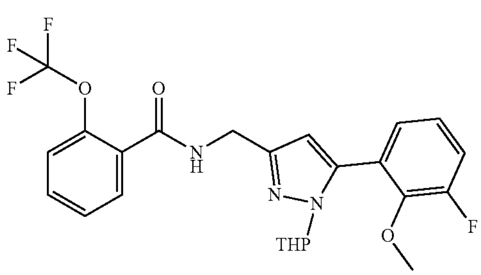 | 393.9 | ¹H NMR (400 MHz, DMSO) δ 8.96 (s, 1H), 7.58 (t, J = 8.0 Hz, 2H), 7.52-7.33 (m, 3H), 7.24-7.09 (m, 2H), 6.29 (s, 1H), 5.00 (d, J = 10.0 Hz, 1H), 4.44 (d, J = 5.4 Hz, 2H), 3.84 (d, J = 11.0 Hz, 1H), 3.68 (d, J = 1.4 Hz, 3H), 2.32(s, 1H), 1.91 (s, 1H), 1.79 (d, J = 13.0 Hz, 1H), 1.45 (s, 3H), 1.22 (s, 2H). |
| 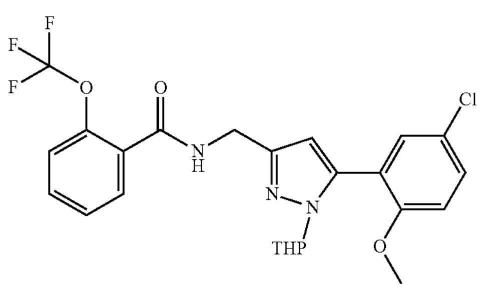 | 509.9 | ¹H NMR (400 MHz, DMSO) δ 8.93 (s, 1H), 7.57 (d, J = 9.7 Hz, 4H), 7.49-7.39 (m, 2H), 7.30 (s, 1H), 7.18 (d, J = 9.0 Hz, 1H), 6.26 (s, 1H), 4.93 (d, J = 8.4 Hz, 1H), 4.43 (s, 2H), 3.85 (s, 1H), 3.77 (s, 3H), 3.34 (s, 1H), 1.91 (s, 1H), 1.80 (s, 1H), 1.46 (s, 3H), 1.22 (s, 2H). |

TABLE 6-continued

| Structure | LC-MS [M + H]+ (m/z) | NMR Data |
|---|---|---|
| 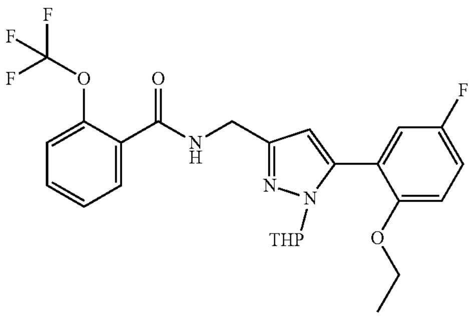 | 507.9 | ¹H NMR (400 MHz, DMSO) δ 8.95 (s, 1H), 7.57 (t, J = 7.9 Hz, 2H), 7.50-7.37 (m, 2H), 7.27 (s, 1H), 7.18-7.05 (m, 2H), 6.26 (s, 1H), 5.01 (d, J = 9.4 Hz, 1H), 4.42 (d, J = 5.1 Hz, 2H), 4.03 (dd, J = 14.6, 7.2 Hz, 3H), 3.85 (d, J = 11.0 Hz, 1H), 2.32 (s, 1H), 1.95 (d, J = 20.9 Hz, 2H), 1.81 (d, J = 11.9 Hz, 1H), 1.45 (s, 4H), 1.18 (dd, J = 24.0, 6.9 Hz, 5H). |
| 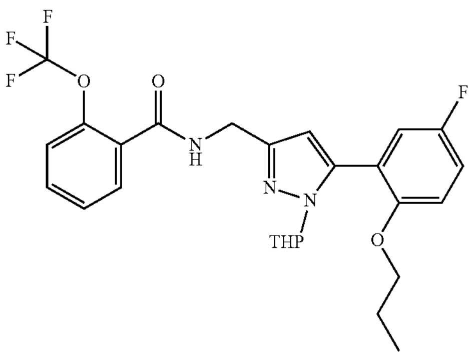 | 521.9 | ¹H NMR (400 MHz, CDCl₃) δ 8.01 (d, J = 6.2 Hz, 1H), 7.50 (t, J = 7.0 Hz, 1H), 7.40 (t, J = 7.4 Hz, 1H), 7.28 (d, J = 17.3 Hz, 3H), 7.17-7.03 (m, 2H), 6.91 (dd, J = 8.8, 4.4 Hz, 1H), 6.30 (s, 1H), 5.04 (d, J = 8.9 Hz, 1H), 4.74 (s, 2H), 4.05 (d, J = 10.1 Hz, 1H), 3.97-3.77 (m, 2H), 3.47 (t, J = 10.7 Hz, 1H), 2.50 (d, J = 10.8 Hz, 1H), 2.03 (s, 1H), 1.87 (d, J = 14.1 Hz, 1H), 1.69 (dd, J = 14.0, 6.8 Hz, 3H), 1.26 (s, 2H), 0.89 (t, J = 7.4 Hz, 3H). |
| 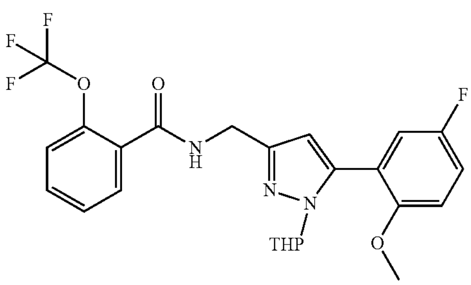 | 493.9 | ¹H NMR (400 MHz, DMSO-d₆): δ 8.92 (s, 1H), 7.59-7.55(m, 2H), 7.46-7.40 (m, 2H), 7.32-7.28(m, 1H), 7.17-7.09 (m, 2H), 4.96(d, J = 10 Hz, 1H), 4.42(d, J = 5.6 Hz, 2H), 3.85(d, J = 10.8 Hz, 1H), 3.74 (s, 3H), 3.34 ( t, J = 8 Hz, 1H), 2.31-2.29 (m, 1H), 1.91 (brs, 1H), 1.79 (d, J = 13.2 Hz, 1H), 1.56-1.45 (m, 3H). |
| 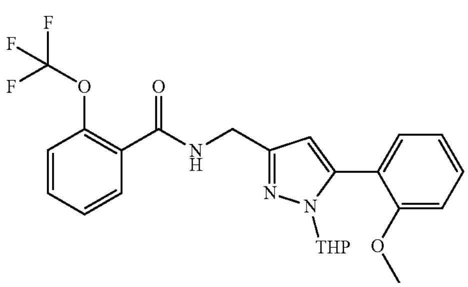 | 475.9 | ¹H NMR (400 MHz, DMSO): δ 8.94 (t, J = 5.5 Hz, 1H), 7.70-7.52 (m, 1H), 7.43 (dd, J = 15.5, 7.9 Hz, 3H), 7.25 (d, J = 7.4 Hz, 1H), 7.15 (d, J = 8.4 Hz, 1H), 7.04 (t J = 7.5 Hz, 1H), 6.18 (s, 1H),4.91 (d, J = 10.1 Hz, 1H), 4.41 (t, J = 9.5 Hz, 2H), 3.75 (s, 3H), 2.30 (d, J = 12.2 Hz, 1H), 1.91 (s, 1H), 1.77 (d, J = 12.4 Hz, 1H), 1.48 (dd, J = 22.0, 10.6 Hz, 3H). |
| 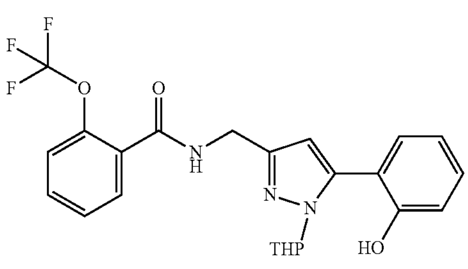 | 462.2 | ¹H NMR (400 MHz, DMSO): δ 9.82 (s, 1H), 8.93 (t, J = 5.6 Hz, 1H), 7.67-7.51 (m, 2H), 7.43 (dd, J = 15.0, 7.9 Hz, 2H), 7.25 (dd, J = 11.0, 4.5 Hz, 1H), 7.18 (d, J = 6.2 Hz, 1H), 6.96 (d, J = 8.0 Hz, 1H), 6.88 (t, J = 7.1 Hz, 1H), 6.19 (s, 1H), 5.04 (d, J = 8.1 Hz, 1H), 4.42 (dt, J = 18.5, 9.2 Hz, 2H), 3.85 (d, J = 10.6 Hz, 1H), 3.35-3.27 (m, 1H), 2.32 (s, 1H), 1.93 (s, 1H), 1.81 (d, J = 12.7 Hz, 1H), 1.48 (dd, J = 19.5, 8.7 Hz, 3H). |

TABLE 6-continued

| Structure | LC-MS [M + H]+ (m/z) | NMR Data |
|---|---|---|
| 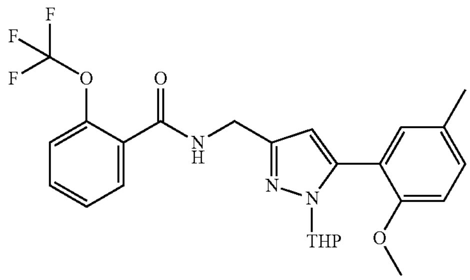 | 489.9 | ¹H NMR (400 MHz, DMSO) δ 8.93 (s, 1H), 7.57 (t, J = 7.9 Hz, 2H), 7.44 (dd, J = 14.4, 7.7 Hz, 2H), 7.24 (d, J = 8.9 Hz, 1H), 7.09-6.97 (m, 2H), 6.17 (s, 1H), 4.91 (d, J = 9.6 Hz, 1H), 4.42 (d, J = 5.9 Hz, 2H), 4.09 (d, J = 5.2 Hz, 1H), 3.86 (d, J = 11.5 Hz, 1H), 3.72 (s, 3H), 3.15 (d, J = 5.2 Hz, 2H), 2.26 (s, 3H), 1.91 (s, 1H), 1.77 (d, J = 13.4 Hz, 1H), 1.58-1.37 (m, 3H). |
| 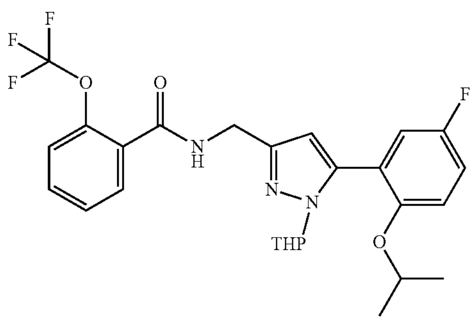 | 521.9 | ¹H NMR (400 MHz, DMSO): δ 8.94 (s, 1H), 7.55-7.59 (m, 2H), 7.40-7.46 (m, 2H), 7.24-7.28 (m, 1H), 7.15-7.18 (m, 1H), 7.07-7.09 (m, 1H), 6.24 (s, 1H), 5.09 (d, J = 10.0Hz, 1H), 4.54 (t, J = 5.6 Hz, 1H), 4.41 (d, J = 5.2 Hz, 1H), 3.82 (d, J = 10.4 Hz, 1H), 2.32-2.38 (m, 1H), 1.9 (s,1H), 1.80 (d, J = 16.0 Hz, 1H).1.45-1.52 (m, 3H), 1.18(d, J = 5.6 Hz, 3H), 1.15(d, J = 2.8 Hz, 3H). |
| 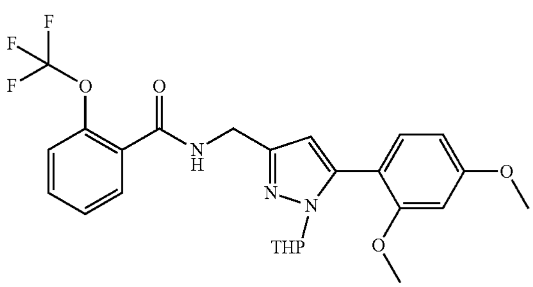 | 505.9 | |

Step 5: N-((5-(4-methylthiophen-3-yl)-1H-pyrazol-3-yl) methyl)-2-(trifluoro methoxy) benzamide

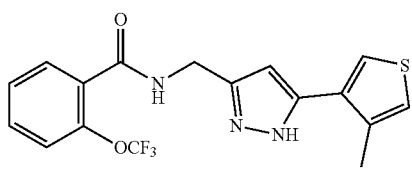 [SMILES: Cc1cscc1-c1cc(CNC(=O)c2ccccc2OC(F)(F)F)n[nH]1]

To a stirred solution of N-((5-(4-methylthiophen-3-yl)-1-(tetrahydro-2H-pyran-2-yl)-1H-pyrazol-3-yl) methyl)-2-(trifluoro methoxy) benzamide (34 mg, 0.073 mmol) in dichloromethane (3 mL) at 0° C. was added 1,4-dioxane-HCl (4.0M, 3 mL). The resultant reaction mixture was stirred at room temperature for 4 h. After the completion of the reaction the mixture was concentrated, further co-distilled with dichloromethane (2×10 mL) to obtain the crude material. Further processing was done by the addition of H₂O (10 mL) followed by basification with sat. NaHCO₃ solution and extraction with EtOAc (2×5 mL). The combined organic layer was dried over Na₂SO₄, and concentrated to afford the crude compound. It was then purified by preparative TLC (eluent: 30% EtOAc+Hexane) to afford N-((5-(4-methylthiophen-3-yl)-1H-pyrazol-3-yl) methyl)-2-(trifluoro methoxy) benzamide (19 mg, 68.24%) as an off-white solid. ¹H NMR (400 MHz, DMSO) δ 12.77 (d, J=41.1 Hz, 1H), 8.92 (d, J=39.6 Hz, 1H), 7.66 (s, 1H), 7.58 (d, J=7.0 Hz, 2H), 7.43 (s, 2H), 7.24 (d, J=43.8 Hz, 1H), 6.38 (d, J=20.0 Hz, 1H), 4.55-4.36 (m, 2H), 2.37 (s, 1H), 2.30 (d, J=14.2 Hz, 2H), 1.22 (s, 1H). LC-MS m/z (M-H): 382.1.

The following compounds in Table 7 were prepared using similar procedures to those described above for Compound 16 using the appropriate starting materials.

TABLE 7

| Example/ Compound Nos. | Structure | LC-MS [M + H]+ (m/z) | NMR Data |
|---|---|---|---|
| 17 | 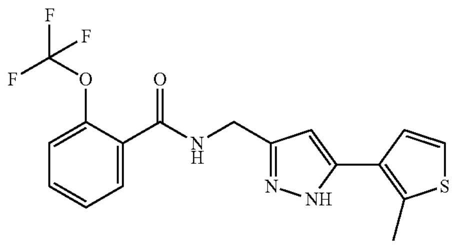 [SMILES: Cc1sccc1-c1cc(CNC(=O)c2ccccc2OC(F)(F)F)n[nH]1] | 382.1 | ¹H NMR (400 MHz, DMSO) δ 12.77 (d, J = 24.0 Hz, 1H), 8.92 (d, J = 37.7 Hz, 1H), 7.58 (s, 2H), 7.45 (d, J = 7.5 Hz, 2H), 7.24 (s, 2H), 6.35 (s, 1H), 4.46 (d, J = 16.9 Hz, 2H), 2.51 (s, 3H). |
| 18 | 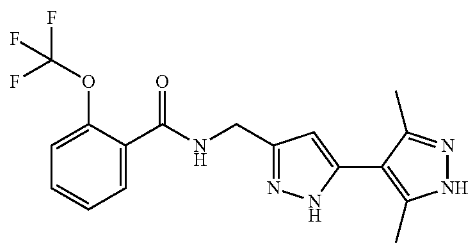 [SMILES: Cc1n[nH]c(C)c1-c1cc(CNC(=O)c2ccccc2OC(F)(F)F)n[nH]1] | 379.9 | ¹H NMR (400 MHz, DMSO-$d_6$) δ 12.36 (s, 1H), 8.86 (s, 1H), 7.57 (s, 2H), 7.43 (s, 2H), 6.13 (s, 1H), 4.43 (s, 2H), 2.22 (s, 6H) |
| 19 | 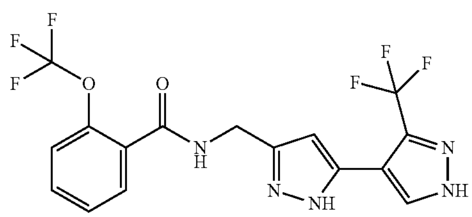 [SMILES: O=C(NCc1cc(-c2c[nH]nc2C(F)(F)F)[nH]n1)c1ccccc1OC(F)(F)F] | 419.9 | ¹H NMR (400 MHz, DMSO) δ 13.62 (s, 1H), 12.83 (d, J = 22.0 Hz, 1H), 8.94 8.21 (d, J = 19.5 Hz, 1H), 7.73-7.51 (m, 2H), 7.45 (dd, J = 17.4, 7.7 Hz, 2H), 6.31 (s, 1H), 4.44 (d, J = 16.9 Hz, 2H). |
| 20 | 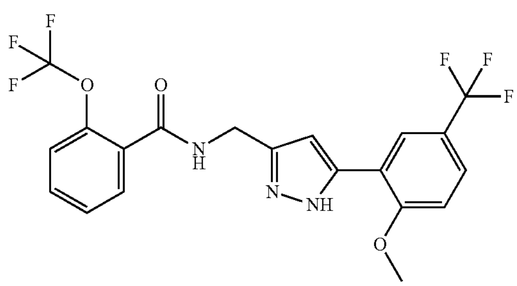 [SMILES: COc1ccc(C(F)(F)F)cc1-c1cc(CNC(=O)c2ccccc2OC(F)(F)F)n[nH]1] | 459.8 | ¹H NMR (400 MHz, DMSO-$d_6$) δ 12.95 (s, 1H), 8.89 (s, 1H), 7.58-7.69 (m, 3H), 7.42-7.47 (m, 2H), 7.28-7.33 (s, 1H), 4.43-4.51 (m, 2H), 3.92 (s, 3H) |
| 21 | 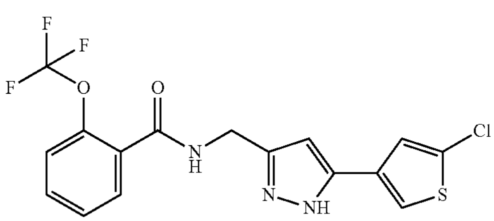 [SMILES: O=C(NCc1cc(-c2csc(Cl)c2)[nH]n1)c1ccccc1OC(F)(F)F] | 402.0 | ¹H NMR (400 MHz, DMSO) δ 12.89 (d, J = 97.1 Hz, 1H), 8.92 (d, J = 38.5 Hz, 1H), 7.63-7.67 (m, 3H), 7.51-7.31 (m, 3H), 6.46 (s, 1H), 4.42 (d, J = 25.4 Hz, 2H). |
| 22 | 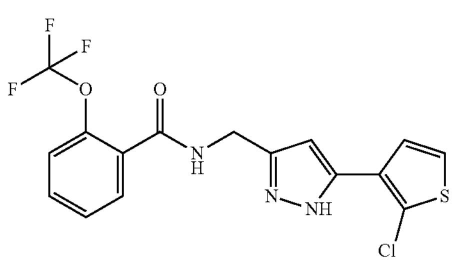 [SMILES: O=C(NCc1cc(-c2ccsc2Cl)[nH]n1)c1ccccc1OC(F)(F)F] | 402.0 | ¹H NMR (400 MHz, DMSO) δ 13.01 (d, J = 43.2 Hz, 1H), 8.95 (d, J = 35.9 Hz, 1H), 7.60 (t, J = 12.3 Hz, 2H), 7.52-7.31 (m, 3H), 6.72 (d, J = 8.9 Hz, 1H), 4.47 (dd, J = 23.9, 5.6 Hz, 2H). |

TABLE 7-continued

| Example/ Compound Nos. | Structure | LC-MS [M + H]+ (m/z) | NMR Data |
|---|---|---|---|
| 23 | 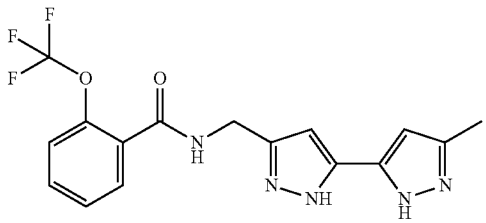 [SMILES: Cc1cc(-c2cc(CNC(=O)c3ccccc3OC(F)(F)F)n[nH]2)[nH]n1] | 365.9 | ¹H NMR (400 MHz, DMSO) δ 12.74 (d, J = 95.7 Hz, 2H), 8.87 (s, 1H), 7.58 (t, J = 7.3 Hz, 2H), 7.44 (dd, J = 16.4, 7.9 Hz, 2H), 6.43 (d, J = 42.0 Hz, 1H), 6.26 (s, 1H), 4.41 (s, 2H), 2.23 (s, 3H) |
| 24 | 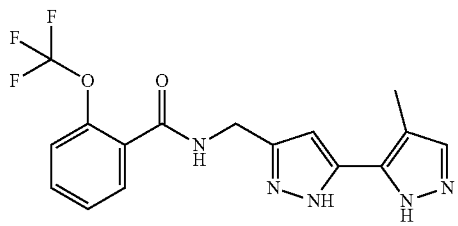 [SMILES: Cc1cn[nH]c1-c1cc(CNC(=O)c2ccccc2OC(F)(F)F)n[nH]1] | 365.9 | ¹H NMR (400 MHz, DMSO) δ 12.79 (s, 2H), 8.93 (d, J = 41.1 Hz, 1H), 7.87-7.07 (m, 5H), 6.37 (s, 1H), 4.44 (s, 2H), 2.14 (s, 3H) |
| 25 | 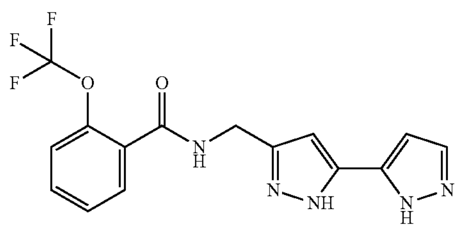 [SMILES: O=C(NCc1cc(-c2ccn[nH]2)[nH]n1)c1ccccc1OC(F)(F)F] | 351.9 | ¹H NMR (400 MHz, DMSO) δ 12.94 (s, 1H), 12.63 (s, 1H), 8.93 (d, J = 46.6 Hz, 1H), 7.78 (s, 1H), 7.58 (s, 2H), 7.52-7.28 (m, 2H), 6.71-6.31 (m, 2H), 4.60-4.32 (m, 2H). |
| 26 | 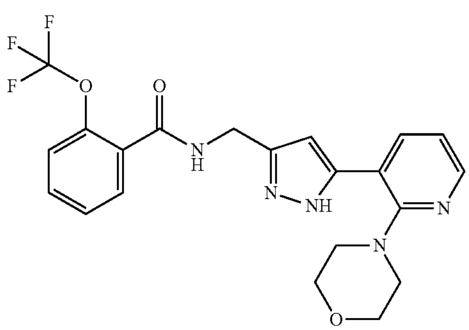 [SMILES: O=C(NCc1cc(-c2cccnc2N2CCOCC2)[nH]n1)c1ccccc1OC(F)(F)F] | 447.9 | ¹H NMR (400 MHz, DMSO-d₆) δ 13.03 (s, 1H), 9.04 (s, 1H), 8.19 (d, J = 2.4 Hz, 1H), 7.80 (bs, 1H), 7.56-7.60 (m, 2H), 7.41-7.47 (m, 2H), 7.02 (s, 1H), 6.67 (s, 1H), 4.44 (d, J = 4.8 Hz, 2H), 3.63 (bs, 4H), 2.97 (bs, 4H) |
| 27 | 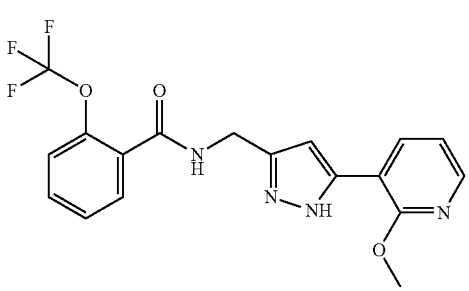 [SMILES: COc1ncccc1-c1cc(CNC(=O)c2ccccc2OC(F)(F)F)n[nH]1] | 392.9 | ¹H NMR (400 MHz, DMSO-d₆) δ 12.92 (s, 1H), 8.90 (s, 1H), 8.13 (d, J = 14.4 Hz, 1H), 8.05 (d, J = 7.0 Hz, 1H), 7.58 (s, 1H), 7.44 (s, 2H), 7.10 (s, 2H), 6.70 (s, H), 4.50 (d, J = 5.9 Hz, 1H), 4.44 (d, J = 5.7 Hz, 1H), 3.94 (d, J = 11.8 Hz, 3H). |

TABLE 7-continued

| Example/ Compound Nos. | Structure | LC-MS [M + H]+ (m/z) | NMR Data |
| --- | --- | --- | --- |
| 29 | 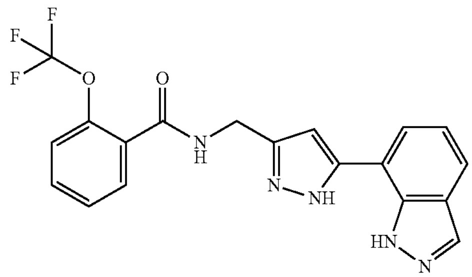 [SMILES: O=C(NCc1cc(-c2cccc3cn[nH]c23)[nH]n1)c1ccccc1OC(F)(F)F] | 401.9 | ¹H NMR (400 MHz, DMSO-d₆) rotamer δ 9.01 (s, 1H), 8.14 (s, 1H), 7.57-7.72 (m, 4H), 7.43-7.49 (m, 2H), 7.15-7.19 (m, 1H), 6.81 (s, 1H), 4.54 (br, 2H) |
| 30 | 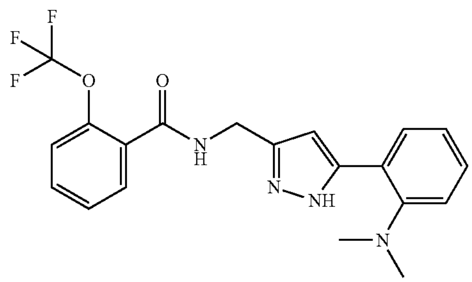 [SMILES: CN(C)c1ccccc1-c1cc(CNC(=O)c2ccccc2OC(F)(F)F)n[nH]1] | 404.9 | ¹H NMR (400 MHz, DMSO) δ 12.76 (s, 1H), 8.88 (s, 1H), 7.55-7.59 (m, 2H), 7.41-7.47 (m, 2H), 7.25(s, 1H), 7.12(s, 1H), 7.02(s, 1H), 6.55 (s, 1H), 4.44 (2, 2H), 3.32 (s, 6H). |
| 31 | 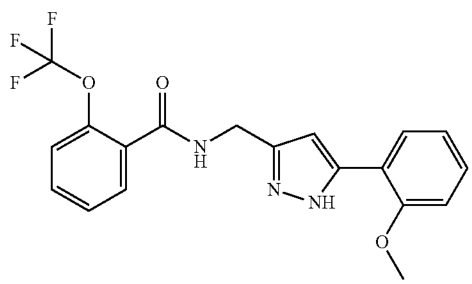 [SMILES: COc1ccccc1-c1cc(CNC(=O)c2ccccc2OC(F)(F)F)n[nH]1] | 391.9 | ¹H NMR (400 MHz, DMSO): δ 12.71 (s, 1H), 8.88 (s, 1H), 7.73-7.54 (m, 3H), 7.44 (dd, J = 16.7, 8.5 Hz, 2H), 7.31 (t, J = 7.8 Hz, 1H), 7.11 (d, J = 8.2 Hz, 1H), 7.00 (t, J = 7.4 Hz, 1H), 6.62 (s, 1H), 4.45 (d, J = 5.5 Hz, 2H), 3.86 (s, 3H). |
| 32 | 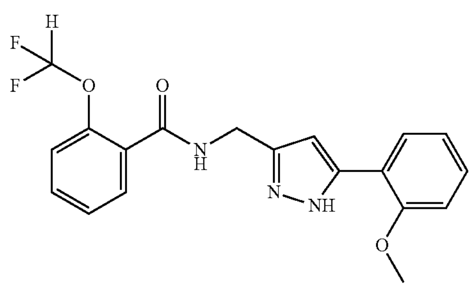 [SMILES: COc1ccccc1-c1cc(CNC(=O)c2ccccc2OC(F)F)n[nH]1] | 374.1 | |
| 33 | 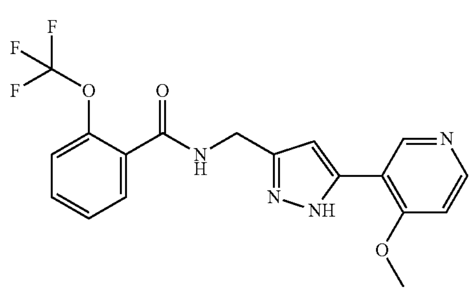 [SMILES: COc1ccncc1-c1cc(CNC(=O)c2ccccc2OC(F)(F)F)n[nH]1] | 393.1 | ¹H NMR (400 MHz, DMSO-d₆) δ 12.91 (s, 1H), 8.92 (s, 1H), 8.38 (s, 1H), 7.56-7.61 (m, 2H), 7.41-7.47 (m, 2H), 7.15 (s, 1H), 6.65 (s, 1H), 4.46 (s, 2H), 3.92 (s, 1H) |

TABLE 7-continued

| Example/ Compound Nos. | Structure | LC-MS [M + H]+ (m/z) | NMR Data |
|---|---|---|---|
| 35 | 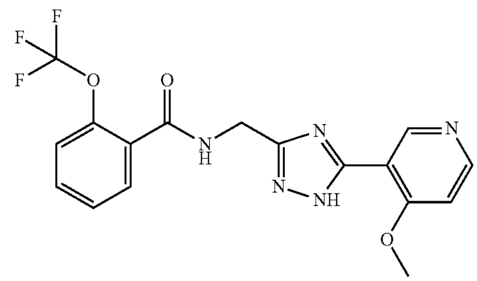 [SMILES: COc1ccncc1-c1nc(CNC(=O)c2ccccc2OC(F)(F)F)n[nH]1] | 394.1 | |
| 36 | 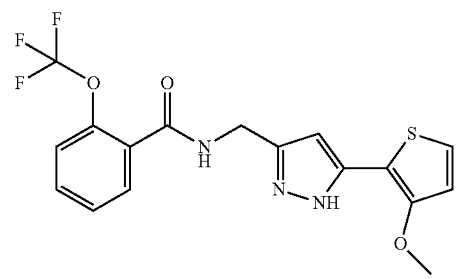 [SMILES: COc1ccsc1-c1cc(CNC(=O)c2ccccc2OC(F)(F)F)n[nH]1] | 398.22 | ¹H NMR (400 MHz, DMSO) δ 12.62 (s, 1H), 8.96 (s, 1H), 7.58 (d, J = 7.4 Hz, 2H), 7.45 (dd, J = 15.9, 7.9 Hz, 2H), 7.30 (s, 1H), 7.04 (s, 1H), 6.51 (s, 1H), 4.45 (s, 2H), 3.85 (s, 3H). |
| 37 | 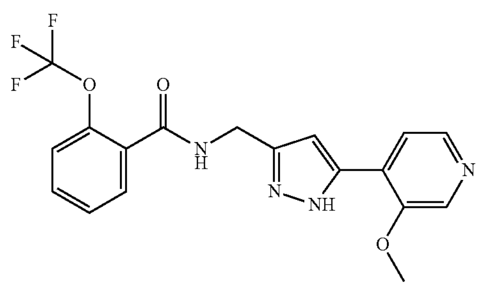 [SMILES: COc1cnccc1-c1cc(CNC(=O)c2ccccc2OC(F)(F)F)n[nH]1] | 392.9 | ¹H NMR (400 MHz, DMSO-d₆) δ 13.09 (s, 1H), 8.90 (s, 1H), 8.43 (s, 1H), 8.23 (s, 1H), 7.58-7.60 (m, 2H), 7.42-7.47 (m, 2H), 6.78 (s, 1H), 4.45 (s, 2H), 3.95 (s, 3H) |
| 38 | 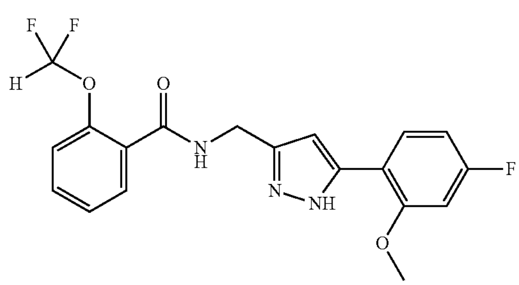 [SMILES: COc1cc(F)ccc1-c1cc(CNC(=O)c2ccccc2OC(F)F)n[nH]1] | 392.1 | |
| 39 | 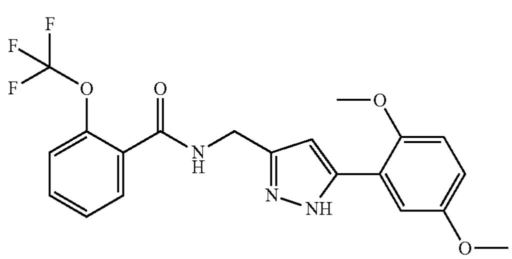 [SMILES: COc1ccc(OC)c(-c2cc(CNC(=O)c3ccccc3OC(F)(F)F)n[nH]2)c1] | 421.9 | ¹H NMR (400 MHz, DMSO) δ 12.75 (s, 1H), 8.89 (s, 1H), 7.58 (s, 2H), 7.44 (s, 2H), 7.22 (s, 1H), 7.03 (s, 1H), 6.89 (s, 1H), 6.65 (s, 1H), 4.44 (s, 2H), 3.77 (d, J = 23.9 Hz, 6H). |

TABLE 7-continued

| Example/ Compound Nos. | Structure | LC-MS [M + H]+ (m/z) | NMR Data |
|---|---|---|---|
| 41 | 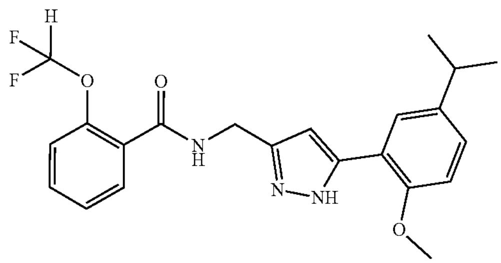 [SMILES: COc1ccc(C(C)C)cc1-c1cc(CNC(=O)c2ccccc2OC(F)F)n[nH]1] | 416.1 | |
| 42 | 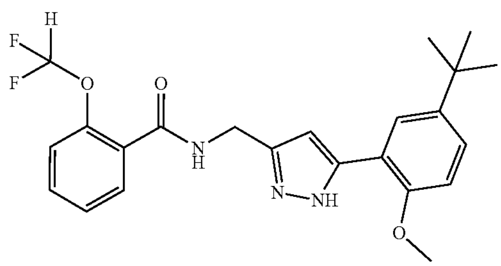 [SMILES: COc1ccc(C(C)(C)C)cc1-c1cc(CNC(=O)c2ccccc2OC(F)F)n[nH]1] | 430.1 | |
| 44 | 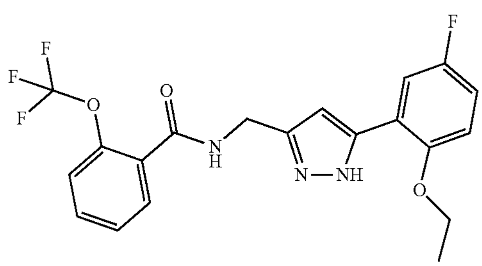 [SMILES: CCOc1ccc(F)cc1-c1cc(CNC(=O)c2ccccc2OC(F)(F)F)n[nH]1] | 423.9 | $^1$H NMR (400 MHz, DMSO) δ 12.86 (d, J = 35.1 Hz, 1H), 8.89 (s, 1H), 7.58 (s, 3H), 7.50 -7.38 (m, 2H), 7.11 (s, 2H), 6.74 (s, 1H), 4.44 (s, 2H), 4.09 (s, 2H), 1.36 (t, J = 6.7 Hz, 3H). |
| 45 | 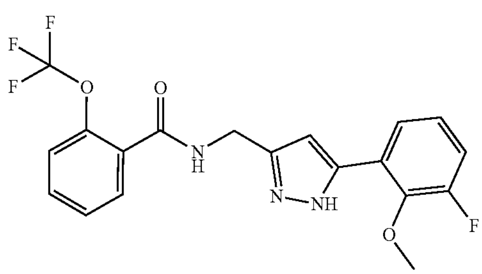 [SMILES: COc1c(F)cccc1-c1cc(CNC(=O)c2ccccc2OC(F)(F)F)n[nH]1] | 409.9 | $^1$H NMR (400 MHz, DMSO) δ 12.94 (s, 1H), 8.95 (d, J = 37.2 Hz, 1H), 7.63 (d, J = 40.2 Hz, 2H), 7.45 (d, J = 10.2 Hz, 2H), 7.18 (s, 2H), 6.66 (s, 1H), 4.48 (d, J = 19.5 Hz, 2H), 3.81 (d, J = 13.6 Hz, 3H). |
| 46 | 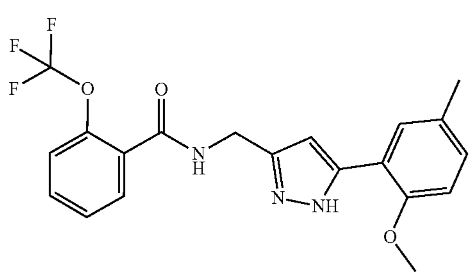 [SMILES: COc1ccc(C)cc1-c1cc(CNC(=O)c2ccccc2OC(F)(F)F)n[nH]1] | 405.9 | $^1$H NMR (400 MHz, DMSO) δ 12.51 (s, 1H), 8.90 (s, 1H), 7.58 (t, J = 8.8 Hz, 2H), 7.53-7.34 (m, 3H), 7.10 (d,J = 8.1 Hz, 1H), 6.99 (d, J = 8.4 Hz, 1H), 6.60 (s, 1H), 4.44 (s, 2H), 3.81 (s, 3H), 2.29 (d, J = 22.8 Hz, 3H). |

TABLE 7-continued

| Example/ Compound Nos. | Structure | LC-MS [M + H]+ (m/z) | NMR Data |
|---|---|---|---|
| 47 | 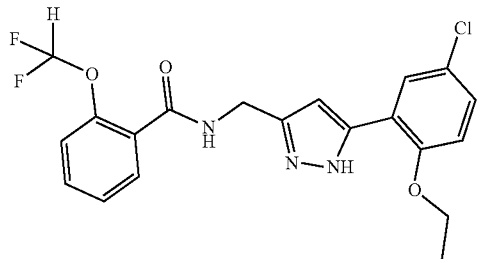 [SMILES: CCOc1ccc(Cl)cc1-c1cc(CNC(=O)c2ccccc2OC(F)F)n[nH]1] | 422.1 | |
| 48 | 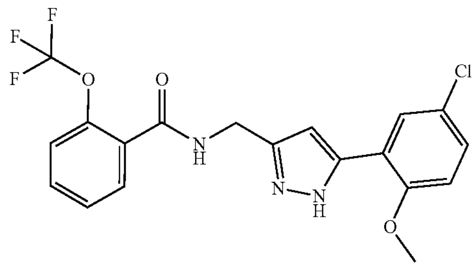 [SMILES: COc1ccc(Cl)cc1-c1cc(CNC(=O)c2ccccc2OC(F)(F)F)n[nH]1] | 425.8 | ¹H NMR (400 MHz, DMSO) δ 12.86 (s, 1H), 8.91 (s, 1H), 7.73 (s, 1H), 7.64-7.54 (m, 2H), 7.47 ? 7.38 (m, 2H), 7.33 (s, 1H), 7.14 (s, 1H), 6.69 (s, 1H), 4.45 (s, 2H), 3.86 (s, 3H). |
| 49 | 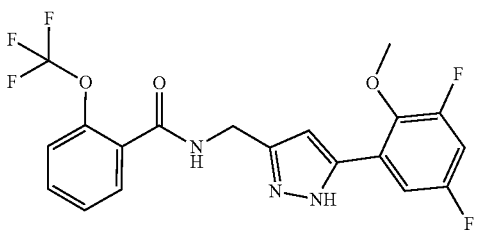 [SMILES: COc1c(F)cc(F)cc1-c1cc(CNC(=O)c2ccccc2OC(F)(F)F)n[nH]1] | 427.8 | ¹H NMR (400 MHz, DMSO-d₆) δ 13.04 (s, 1H), 8.90 (s, 1H), 7.58-7.60 (m, 2H), 7.42-7.46 (m, 3H), 7.26 (s, 1H), 6.72 (s, 1H), 4.45 (s, 2H), 3.77 (s, 3H) |
| 51 | 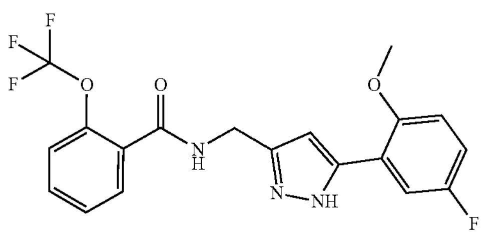 [SMILES: COc1ccc(F)cc1-c1cc(CNC(=O)c2ccccc2OC(F)(F)F)n[nH]1] | 410.1 | ¹H NMR (400 MHz, DMSO-d₆): δ 12.82 (s, 1H), 8.87 (s, 1H), 7.59-7.41 (m, 5H), 7.12 (brs, 2H), 6.69 (s, 1H), 4.44 (brs, 2H), 3.84 (s, 3H). |
| 113 | 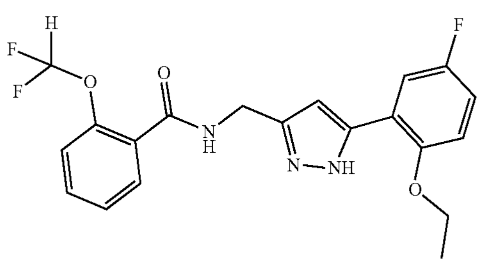 [SMILES: CCOc1ccc(F)cc1-c1cc(CNC(=O)c2ccccc2OC(F)F)n[nH]1] | 406.1 | |
| 114 | 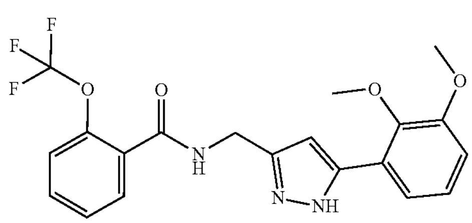 [SMILES: COc1cccc(-c2cc(CNC(=O)c3ccccc3OC(F)(F)F)n[nH]2)c1OC] | 421.8 | ¹H NMR (400 MHz, DMSO-d₆) rotamer δ 12.89 (s, 1H), 8.92 (bs, 1H), 7.56-7.58 (m, 2H), 7.41-7.47 (m, 2H), 7.29 (bs, 1H), 7.09 (s, 1H), 7.01 (s, 1H), 4.45 (s, 2H), 3.82 (s, 3H), 3.68 (s, 3H) |

TABLE 7-continued

| Example/ Compound Nos. | Structure | LC-MS [M + H]+ (m/z) | NMR Data |
|---|---|---|---|
| 115 | 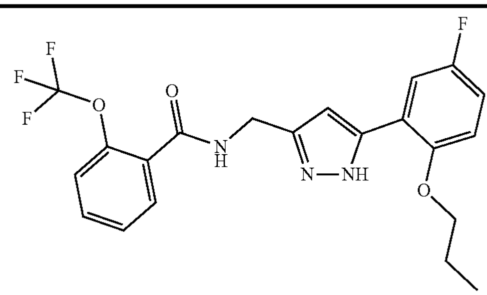 | 437.9 | $^1$H NMR (400 MHz, DMSO) δ 12.85 (d, J = 25.9 Hz, 1H), 8.93 (d, J = 39.7 Hz, 1H), 7.59 (s, 3H), 7.43 (s, 2H), 7.09 (d, J = 25.8 Hz, 2H), 6.73 (s, 1H), 4.45 (d, J = 19.5 Hz, 2H), 4.01 (s, 2H), 1.76 (s, 2H), 0.95 (s, 3H). |
| 116 | 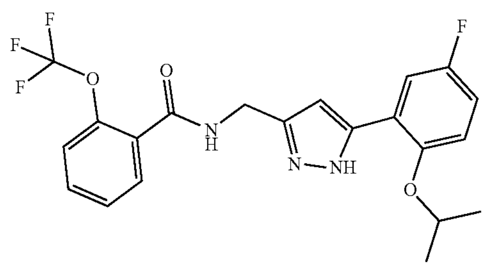 [SMILES: CC(C)Oc1ccc(F)cc1-c1cc(CNC(=O)c2ccccc2OC(F)(F)F)n[nH]1] | 337.9 | $^1$H NMR (400 MHz, DMSO): δ 12.86 (s, 1H), 8.98 (s, 1H), 7.43-7.65 (m, 5 H), 7.06-7.13 (m, 2H), 6.74-6.78 (m, 1H), 4.64 (s, 1H), 4.43 (d, J = 2.8 Hz, 2H), 1.27 (s, 6H). |
| 117 | 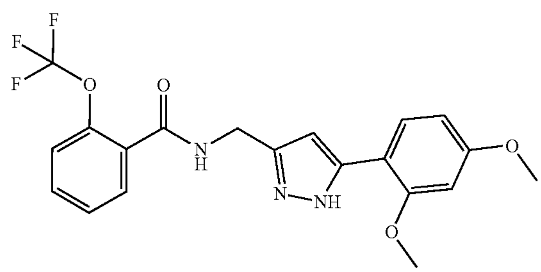 [SMILES: COc1ccc(-c2cc(CNC(=O)c3ccccc3OC(F)(F)F)n[nH]2)c(OC)c1] | 421.9 | $^1$H NMR (400 MHz, DMSO): δ 12.56 (s, 1H), 8.84 (s, 1H), 7.51-7.57 (m, 3 H), 7.43-7.45 (m, 2H), 6.49-6.64 (m, 3H), 4.41 (s, 2H), 3.84 (s, 3H), 3.78 (s, 3H). |

Synthesis of N-((5-(2,5-dihydroxyphenyl)-1H-pyrazol-3-yl) methyl)-2-(trifluoro methoxy) benzamide (Compound 40)

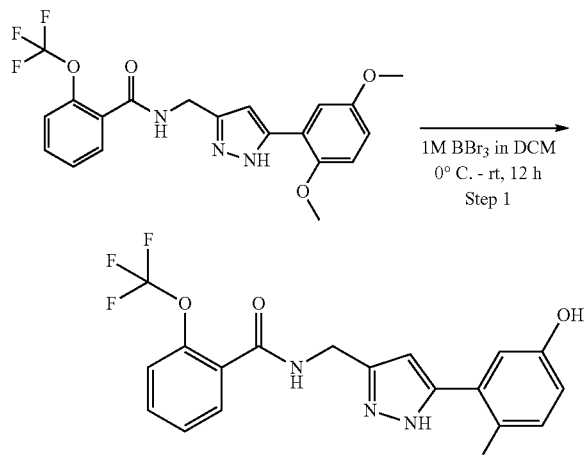

To a stirred solution of N-((5-(2,5-dimethoxyphenyl)-1H-pyrazol-3-yl) methyl)-2-(trifluoro methoxy) benzamide (90 mg, 0.365 mmol) in dichloromethane (5 mL) at 0° C. was added a solution of BBr$_3$ in dichloromethane (1.0M, 4 mL). The resultant mixture was stirred at room temperature for 12 h. After the completion of reaction, it was quenched with aqueous NaHCO$_3$ solution (5 mL) and extracted with 10% MeOH in DCM (2×10 mL). The combined organic layer was dried over Na$_2$SO$_4$ and concentrated to obtain the crude compound. It was purified by preparative TLC (3% MeOH in DCM) to afford N-((5-(2,5-dihydroxyphenyl)-1H-pyrazol-3-yl) methyl)-2-(trifluoro methoxy) benzamide as off white solid (24 mg, 34.28%). $^1$H NMR (400 MHz, DMSO) δ 12.80 (d, 1H), 9.85 (d, 1H), 8.93 (d, 2H), 7.62 (d, 2H), 7.45 (s, 2H), 6.99 (s, 1H), 6.71 (s, 1H), 6.59 (s, 2H), 4.47 (d, 2H) LC-MS (ESI): m/z 393.9 (M+H)$^+$ The following compounds in Table 8 were prepared using similar procedures to those described above for Compound 40 using the appropriate starting materials.

TABLE 8

| Example/ Compound Nos. | Structure | LC-MS [M+ H]+ (m/z) | NMR Data |
|---|---|---|---|
| 28 | 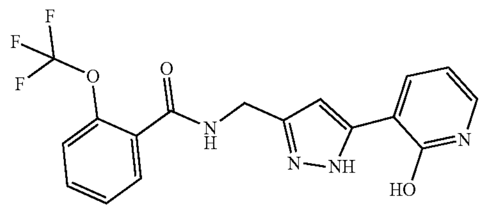 [SMILES: O=C(NCc1cc(-c2cccnc2O)[nH]n1)c1ccccc1OC(F)(F)F] | 378.9 | ¹H NMR (400 MHz, DMSO-d₆) δ 12.03 (s, 1H), 8.90 (s, 1H), 7.95 (d, J = 7.0 Hz, 1H), 7.58 (t, J = 8.6 Hz, 3H), 7.49-7.42 (m, 1H), 7.41 (s, 1H), 6.83 (s, 1H), 6.32 (d, J = 7.3 Hz, 1H), 4.43 (d, J = 5.8 Hz, 2H). |
| 43 | 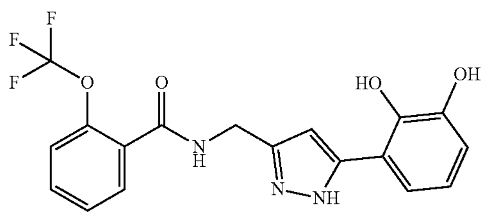 [SMILES: O=C(NCc1cc(-c2cccc(O)c2O)[nH]n1)c1ccccc1OC(F)(F)F] | 394.1 | ¹H NMR (400 MHz, DMSO-d₆) δ 8.99 (s, 1H), 7.53-7.64 (m, 3H), 7.42-7.48 (m, 3H), 7.01 (d, J = 10 Hz, 1H), 6.61-6.67 (m, 4H), 4.49 (s, 2H). |
| 50 | 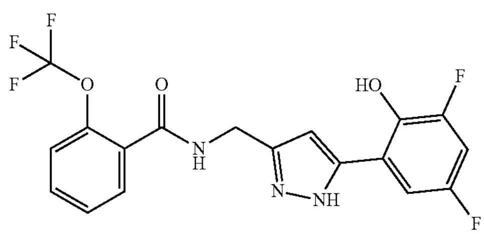 [SMILES: O=C(NCc1cc(-c2cc(F)cc(F)c2O)[nH]n1)c1ccccc1OC(F)(F)F] | 413.8 | ¹H NMR (400 MHz, DMSO-d₆) δ 13.32 (s, 1H), 11.03 (s, 1H), 9.05 (s, 1H), 7.57.766 (m, 1H), 7.58 (s, 2H), 7.42-7.49 (m, 3H), 7.17 (m, 1H), 6.84 (s, 1H), 4.50 (s, 2H). |
| 52 | 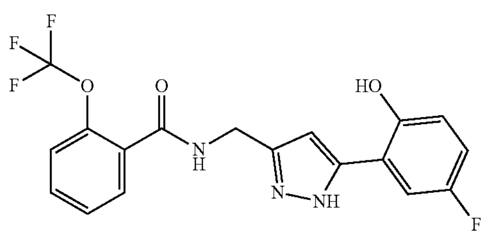 [SMILES: O=C(NCc1cc(-c2cc(F)ccc2O)[nH]n1)c1ccccc1OC(F)(F)F] | 396.3 | |
| 53 | 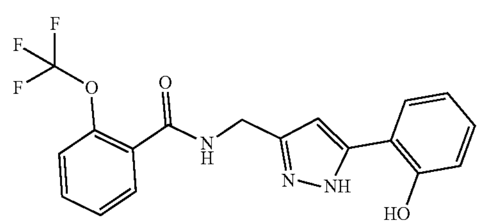 [SMILES: O=C(NCc1cc(-c2ccccc2O)[nH]n1)c1ccccc1OC(F)(F)F] | 378.2 | ¹H NMR (400 MHz, DMSO): δ 11.91 (s, 1H), 8.99 (s, 1H), 7.61 (dt, J = 16.0, 7.9 Hz, 3H), 7.45 (dd, J = 16.4, 8.1 Hz, 2H), 7.13 (t, J = 7.3 Hz, 1H), 6.89 (d, J = 8.0 Hz, 1H), 6.84 (t, J = 7.2 Hz, 1H), 6.68 (s, 1H), 4.49 (d, J = 5.5 Hz, 2H). |
| 54 | 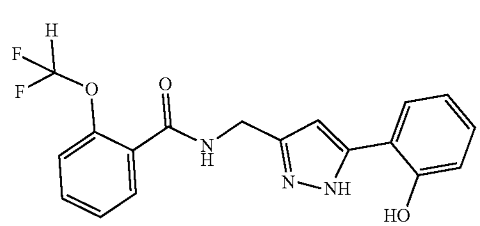 [SMILES: O=C(NCc1cc(-c2ccccc2O)[nH]n1)c1ccccc1OC(F)F] | 360.1 | |

TABLE 8-continued

| Example/Compound Nos. | Structure | LC-MS [M+ H]+ (m/z) | NMR Data |
|---|---|---|---|
| 56 | 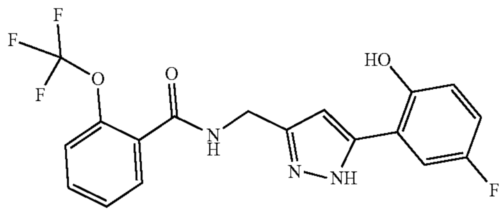 [SMILES: O=C(NCc1cc(-c2cc(F)ccc2O)[nH]n1)c1ccccc1OC(F)(F)F] | 395.9 | ¹H NMR (400 MHz, DMSO-d$_6$): δ 13.19 (s, 1H), 10.72(s, 1H), 9.03 (s, 1H), 7.59-7.7.67(m, 2H), 6.90-6.99 (m, 2H), 6.72-6.79 (m, 1H), 4.51(s, 2H). |
| 57 | 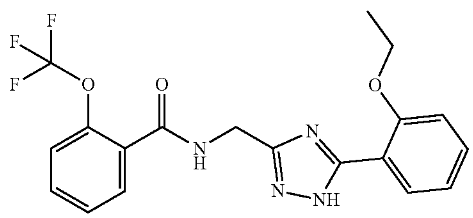 [SMILES: CCOc1ccccc1-c1nc(CNC(=O)c2ccccc2OC(F)(F)F)n[nH]1] | 407.1 | |
| 58 | 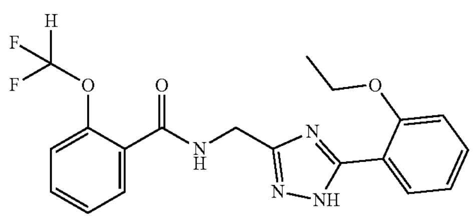 [SMILES: CCOc1ccccc1-c1nc(CNC(=O)c2ccccc2OC(F)F)n[nH]1] | 389.1 | |
| 59 | 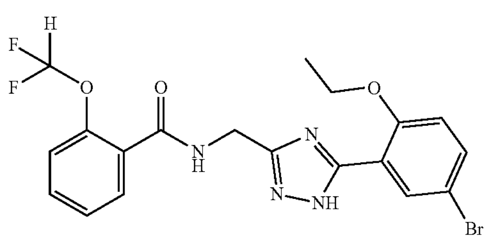 [SMILES: CCOc1ccc(Br)cc1-c1nc(CNC(=O)c2ccccc2OC(F)F)n[nH]1] | 467.0 | |
| 64 | 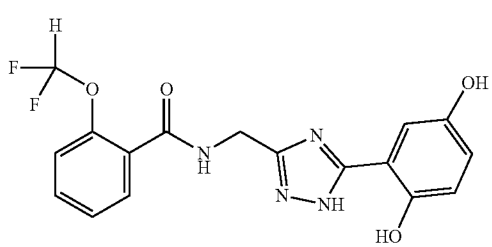 [SMILES: O=C(NCc1n[nH]c(-c2cc(O)ccc2O)n1)c1ccccc1OC(F)F] | 377.30 | |
| 129 | 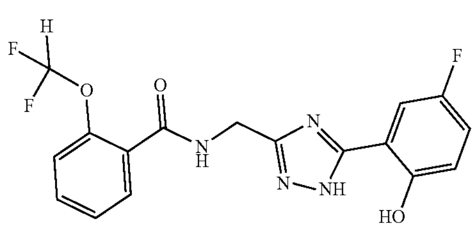 [SMILES: O=C(NCc1n[nH]c(-c2cc(F)ccc2O)n1)c1ccccc1OC(F)F] | 379.1 | |

TABLE 8-continued

| Example/ Compound Nos. | Structure | LC-MS [M+ H]+ (m/z) | NMR Data |
|---|---|---|---|
| 130 | 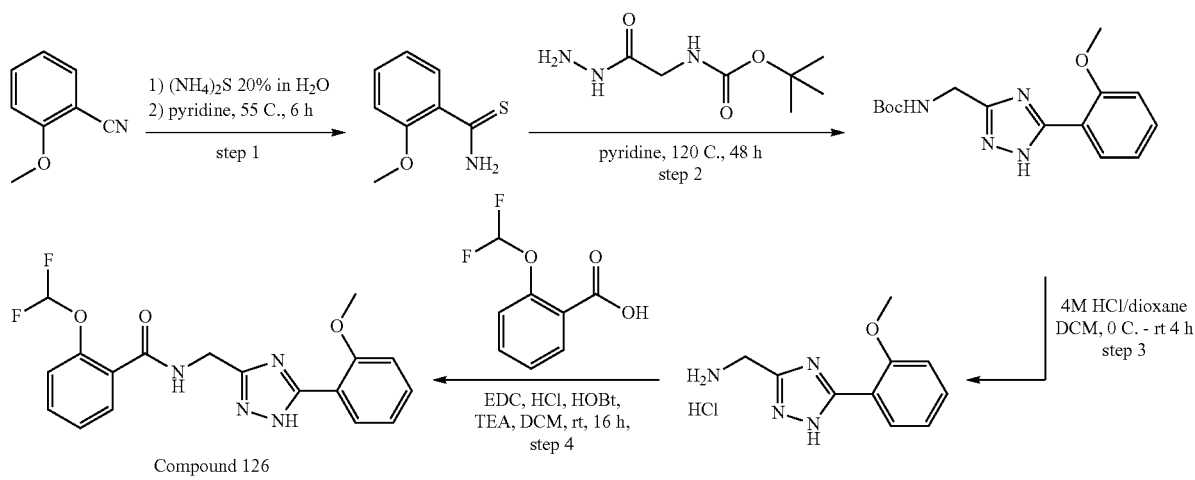 | 396.8 | $^1$H NMR (400 MHz, DMSO): rotamers δ 14.14 (s, 1H), 10.99 (s, 1H), 9.00 (s, 1H), 7.58-7.71 (m, 2H), 7.43-7.49 (m, 2H), 7.14-7.21 (m, 1H), 6.97-7.03 (m, 1H), 4.53 (d, J = 4.8 Hz, 1H) |

Synthesis of 2-(difluoro methoxy)-N-((5-(2-methoxyphenyl)-1H-1, 2, 4-triazol-3-yl) methyl) benzamide (Compound 126)

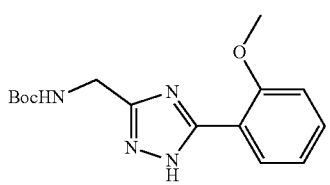

Step-1: Synthesis of 2-methoxybenzothioamide

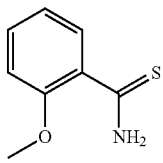

To a stirred solution of 2-methoxy benzo nitrile (130 g, 977 mmol) in pyridine (1200 mL) at 0° C. was added ammonium sulfide solution (650 mL, 5 vol), followed by triethyl amine (150 mL, 1075 mmol). Then the reaction mixture was stirred at 55° C. for 12 h. The reaction was monitored by TLC (30% Ethyl acetate/Hexane). After completion of the reaction, diluted with cold water (4.0 L), solid was filtered, dried over vacuum to afford 2-methoxy-benzothioamide (145 g, yield: 89%) as a yellow solid. $^1$H NMR (400 MHz, DMSO-d$_6$) δ 9.94 br (s, 1H), 9.30 (brs, 1H), 7.68 (d, J=7.6 Hz, 1H), 7.36 (t, J=8.0 Hz, 1H), 7.04 (d, J=8.4 Hz, 1H), 6.94 (t, J=7.2 Hz, 1H), 3.79 (s, 3H).

Step-2: Synthesis of tert-butyl ((5-(2-methoxyphenyl)-1H-1, 2, 4-triazol-3-yl) methyl) carbamate To a stirred solution of 2-methoxybenzothioamide (61 g, 365 mmol) and tert-butyl (2-hydrazinyl-2-oxoethyl), carbamate (207 g, 1095 mmol) in pyridine (300 mL) was heated at 120° C. for 48 h. After completion of reaction by TLC, diluted with water (500 mL) and extracted with EtOAc (2×600 mL), organic layer was separated, washed with saturated NH$_4$Cl solution (500 mL), brine solution (500 mL), dried over Na$_2$SO$_4$, filtered and evaporated to get the crude compound. The crude product was washed with diethyl ether to afford tert-butyl ((5-(2-methoxyphenyl)-1H-1, 2, 4-triazol-3-yl) methyl) carbamate (27 g, yield: 24%) as an off-white solid. $^1$H NMR (400 MHz, DMSO-d$_6$) δ 13.45 (s, 1H), 8.03 (d, J=7.2 Hz, 1H), 7.44 (t, J=7.6 Hz, 1H), 7.22-7.16 (m, 2H), 7.06 (t, J=7.2 Hz, 1H), 4.18 (d, J=5.6 Hz, 2H), 3.94 (s, 3H), 1.38 (s, 9H). LC-MS m/z (M+H): 305.0.

Step-3: Synthesis of (5-(2-methoxyphenyl)-1H-1,2, 4-triazol-3-yl) methanamine hydrochloride

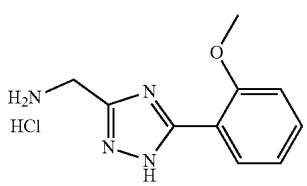

To a stirred solution of tert-butyl ((5-(2-methoxyphenyl)-1H-1,2,4-triazol-3-yl)methyl)carbamate (27 g, 89 mmol) in DCM (150 mL) at 0° C. was added 4M HCl in 1, 4-dioxane-HCl (54 mL, 2 vol) for 10 min. Reaction was stirred at room temperature for 4 h. TLC showed completion of the starting material and formation of a polar spot (5% MeOH/DCM). After completion of the reaction, diluted with pet ether (200 mL), free solid formed was filtered, solid washed with diethyl ether (200 mL), dried under vacuum to afford (5-(2-methoxyphenyl)-1H-1,2,4-triazol-3-yl)methanamine hydrochloride (25 g, yield: 99%) as an off white solid. $^1$H NMR (400 MHz, DMSO-$d_6$) δ 8.66 (brs, 3H), 8.05 (d, J=8.0 Hz, 1H), 7.51-7.47 (m, 1H), 7.22 (d, J=8.4 Hz, 1H), 7.10 (t, J=7.6 Hz, 1H), 6.01 (brs, 3H), 4.13 (d, J=5.6 Hz, 2H), 3.95 (s, 3H). LC-MS m/z (M+H): 205.1.

Step-4: Synthesis of 2-(difluoro methoxy)-N-((5-(2-methoxyphenyl)-1H-1, 2, 4-triazol-3-yl) methyl) benzamide

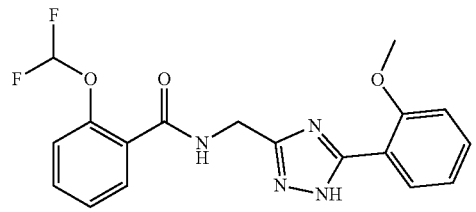 [SMILES: COc1ccccc1-c1nc(CNC(=O)c2ccccc2OC(F)F)n[nH]1]

To a stirred solution of 2-(difluoromethoxy)benzoic acid (20 g, 104 mmol) in DCM (500 mL) at 0° C. was added EDC.HCl (30 g, 156 mmol), HOBt (21 g, 156 mmol), (5-(2-methoxyphenyl)-1H-1,2,4-triazol-3-yl)methanamine hydrochloride (25 g, 104 mmol) and followed by triethyl amine (44 mL, 312 mmol). Reaction was stirred at room temperature for 12 h. After completion of the reaction, solid was filtered through celite bed, the filtrate obtained was washed once with saturated NaHCO$_3$ solution (500 mL), saturated NH$_4$Cl solution (1 Lit) and brine solution. The organic layer was separated, dried over Na$_2$SO$_4$ concentrated under reduced pressure to get the crude. The crude obtained was triturated with acetonitrile (500 mL), stirred for 1 h, filtered and washed with diethyl ether (100 mL), and dried under vacuum to afford 2-(difluoromethoxy)-N-((5-(2-methoxyphenyl)-1H-1,2,4-triazol-3-yl)methyl)benz-amide (19 g, yield: 56%) as an off white solid. $^1$H NMR (400 MHz, DMSO-$d_6$): δ 13.55 (s, 1H), 8.76 (bs, 1H), 8.07 (d, J=7.6 Hz, 1H), 7.61 (d, J=7.6 Hz, 1H), 7.52 (t, J=7.6 Hz, 1H), 7.45 (t, J=8.0 Hz, 1H), 7.36-6.99 (m, 5H), 4.53 (d, J=5.6 Hz, 2H), 3.94 (s, 3H). LC-MS m/z (M+H): 374.9.

Alternative preparation of 2-(difluoromethoxy)-N-((5-(2-methoxyphenyl)-1H-1,2,4-triazol-3-yl)methyl)benzamide, compound 126:

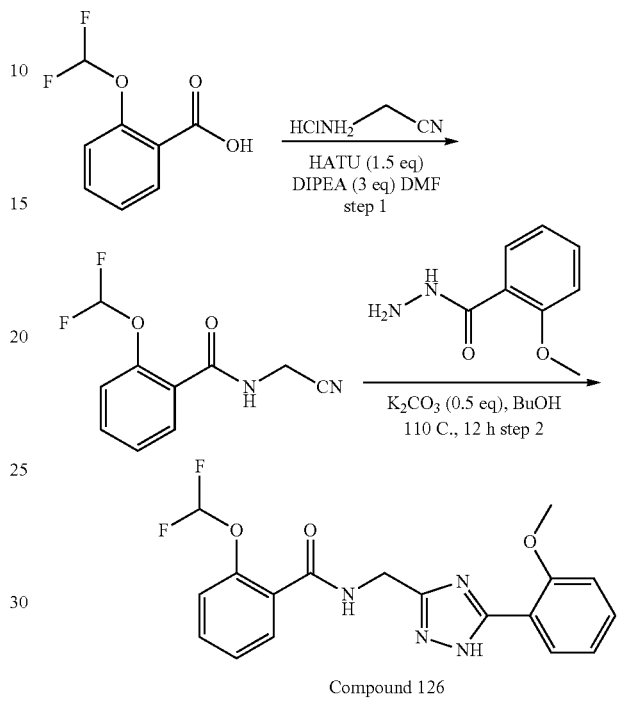

Compound 126

Step 1: Synthesis of N-(cyan methyl)-2-(difluoro methoxy) benzamide

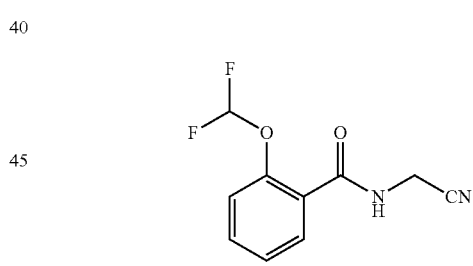

To a stirred solution of 2-(difluoromethoxy) benzoic acid (5 g, 26 mmol) in DMF (20 mL) at 0° C. was added of HATU (15.1 g, 39.8 mmol), DIPEA (10.3 g, 79 mmol) and 2-aminoacetonitrile HCl (2.4 g, 26 mmol). The resulting reaction mixture stirred at room temperature for 16 h. After completion of the reaction by TLC, reaction mixture diluted with ice cold water (50 mL) and extracted with EtOAc (2×50 mL), organic layer was separated, washed with ice cold water (3×100 mL) and followed by brine solution (2×100 mL), finally dried over Na$_2$SO$_4$, concentrated under reduced pressure to get the crude compound. The crude obtained was dissolved in diethyl ether (50 mL) and followed by triturated with pentane (2×50 mL), solid precipitated was filtered, dried under vacuum to afford N-(cyan methyl)-2-(difluoro methoxy) benzamide (3.5 g, Yield-58%) as off white solid. $^1$H NMR (400 MHz, DMSO-$d_6$): 8.98 (t, J=5.2 Hz, 10.4 Hz, 1H), 7.56 (t, J=8 Hz, 16.4 Hz, 2H), 7.33 (t, J=8 Hz, 15.6 Hz, 1H), 7.26 (d, J=8 Hz, 1H) 6.99 (d, J=73.6 Hz, 1H), 4.29 (d, J=5.6 Hz, 2H). LC-MS m/z (M−H): 227.1

Stage-2: Synthesis of 2-(difluoromethoxy)-N-((5-(2-methoxyphenyl)-1H-1, 2, 4-triazol-3-yl) methyl) benzamide

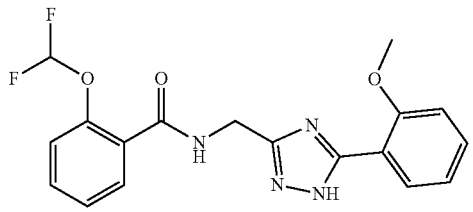 [SMILES: COc1ccccc1-c1nc(CNC(=O)c2ccccc2OC(F)F)n[nH]1]

To a stirred solution of N-(cyan methyl)-2-(difluoro methoxy) benzamide (3.5 g, 13.78 mmol) and 2-methoxy-benzohydrazide (3.44 g, 20.6 mmol) in n-BuOH (20 mL) was added potassium carbonate (0.95 g, 6.89 mmol). The resulting reaction mixture was heated at 110° C. for 16 h. After completion of reaction by TLC, reaction mixture was evaporated under vacuum and diluted with water (50 mL) and extracted with EtOAc (2×50 mL), organic layer was separated, washed with brine solution (20 mL), water (50 mL) and finally dried over $Na_2SO_4$, concentrated to get the brown colored crude compound. The crude obtained was diluted with acetonitrile (5 mL), stirred for 15 minutes, the white solid precipitated was filtered, washed with diethyl ether (2×20 mL) to afford 2-(difluoro methoxy)-N-((5-(2-methoxyphenyl)-1H-1, 2, 4-triazol-3-yl) methyl) benzamide (BRG-0399) (1.9 g, Yield-37%) as off white solid. $^1$H NMR (400 MHz, DMSO-$d_6$): δ 13.5 (s, 1H), 8.76 (s, 1H), 8.06 (d, J=7.6 Hz, 1H), 7.60 (d, J=7.2 Hz, 1H), 7.52 (t, J=7.6 Hz, 15.2 Hz, 1H), 7.45 (t, J=7.6 Hz, 15.2 Hz, 1H), 7.36-6.99 (m, 5H), 4.52 (d, J=5.2 Hz, 2H), 3.94 (s, 3H). LC-MS m/z (M−H): 375.1.

The following compounds in Table 9 were prepared using similar procedures to those described above for Compound 126 using the appropriate starting materials.

TABLE 9

| Example/Compound Nos. | Structure | LC-MS [M + H]+ (m/z) | NMR Data |
|---|---|---|---|
| 119 | 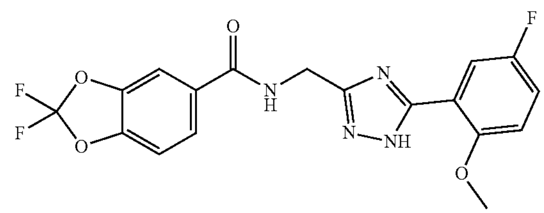 [SMILES: COc1ccc(F)cc1-c1nc(CNC(=O)c2ccc3c(c2)OC(F)(F)O3)n[nH]1] | 407.1 | $^1$H NMR (400 MHz, DMSO): δ 13.66 (s, 1H), 9.10 (s, 1H), 7.88 (s, 1H), 7.82 (d, J = 8.5 Hz, 1H), 7.75 (d, J 6.6 Hz, 1H), 7.52 (d, J = 8.3 Hz, 1H), 7.31 (d, J = 8.0 Hz, 1H), 7.26-7.18 (m, 1H), 4.56 (d, J = 5.3 Hz, 2H), 3.93 (s, 3H). |
| 120 | 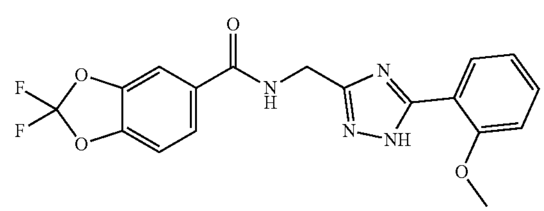 [SMILES: COc1ccccc1-c1nc(CNC(=O)c2ccc3c(c2)OC(F)(F)O3)n[nH]1] | 389.1 | $^1$H NMR (400 MHz, DMSO) δ 13.52 (s, 1H), 9.09 (t, J = 5.3 Hz, 1H), 8.03 (d, J = 7.8 Hz, 1H), 7.89 (d, 7.83-7.79 (m, 1H), 7.53-7.46 (m, 1H), 7.44 (d, J = 7.1 Hz, 1H), 7.18 (d, J = 8.4 Hz, 1H), 7.06 (t, J = 7.4 Hz, 1H), 4.56 (d, J = 5.6 Hz, 2H), 3.94 (s, 3H). |
| 125 | 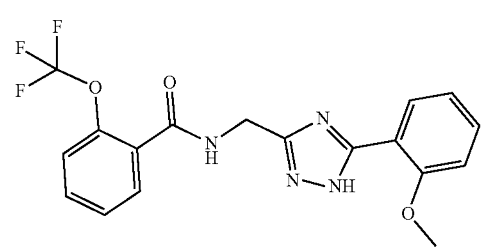 [SMILES: COc1ccccc1-c1nc(CNC(=O)c2ccccc2OC(F)(F)F)n[nH]1] | 392.9 | $^1$H NMR (400 MHz, DMSO): δ 13.53 (s, 1H), 8.91 (s, 1H), 8.05 (d, J = 7.2 Hz, 1H), 7.56-7.63 (m, 2H), 7.41-7.46 (m, 3H), 7.17 (d, J = 8.4 Hz, 1H), 7.07 (t, J = 7.2 Hz, 1H), 4.50 (d, J = 5.6 Hz, 1H), 3.94 (s, 3H). |

TABLE 9-continued

| Example/Compound Nos. | Structure | LC-MS [M + H]+ (m/z) | NMR Data |
|---|---|---|---|
| 128 | 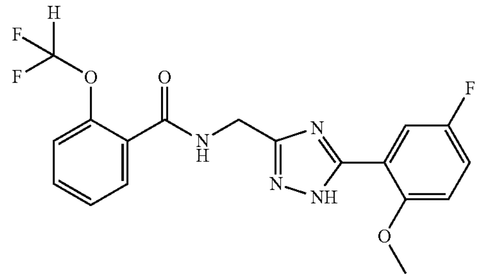 [SMILES: COc1ccc(F)cc1-c1nc(CNC(=O)c2ccccc2OC(F)F)n[nH]1] | 392.9 | $^1$H NMR (400 MHz, DMSO-$d_6$) δ 13.69 (s, 1H), 8.77 (s, 1H), 7.78 (d, J = 9.2 Hz, 1H), 7.60 (d, J = 7.2 Hz, 1H), 7.50 (t, J = 7.6 Hz, 1H), 7.36-7.31 (m, 2H), 7.25-7.18 (m, 2H), 7.25-6.99 (m, 3H), 4.52 (d, J = 5.2 Hz, 2H), 3.94 (s, 3H) |
| 131 | 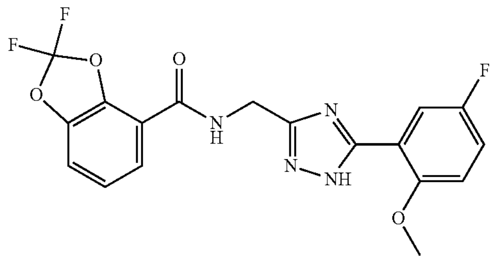 [SMILES: COc1ccc(F)cc1-c1nc(CNC(=O)c2cccc3c2OC(F)(F)O3)n[nH]1] | 406.9 | $^1$H NMR (400 MHz, DMSO) δ 8.92 (s, 1H), 7.75 (d, J = 8.1 Hz, 1H), 7.56 (dd, J = 8.0, 3.1 Hz, 2H), 7.30 (t, J = 8.0 Hz, 2H), 7.21 (dd, J = 9.1, 4.3 Hz, 1H), 4.57 (d, J = 5.5 Hz, 2H), 3.93 (s, 3H). |
| 132 | 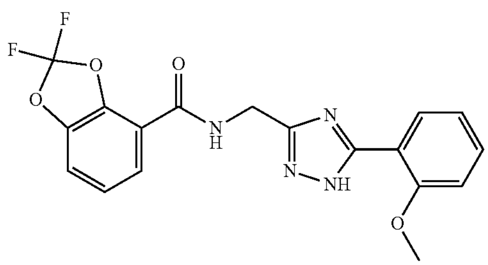 [SMILES: COc1ccccc1-c1nc(CNC(=O)c2cccc3c2OC(F)(F)O3)n[nH]1] | 389.1 | $^1$H NMR (400 MHz, DMSO) δ 13.56 (s, 1H), 8.91 (s, 1H), 8.03 (s, 1H), 7.55 (d, J = 8.0 Hz, 1H), 7.45 (t, J = 7.6 Hz, 1H), 7.30 (t, J = 8.0 Hz, 1H), 7.17 (d, J = 8.4 Hz, 1H), 7.06 (t, J = 7.2 Hz, 1H), 4.56 (s, 2H), 3.93 (s, 3H). |
| 133 | 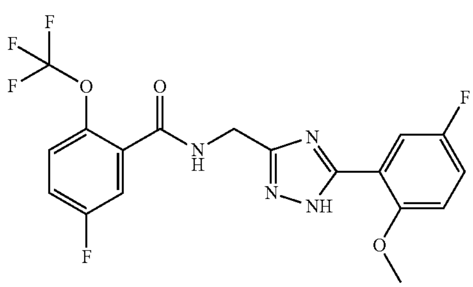 [SMILES: COc1ccc(F)cc1-c1nc(CNC(=O)c2cc(F)ccc2OC(F)(F)F)n[nH]1] | 429.1 | $^1$H NMR (400 MHz, DMSO) δ 13.69 (s, 1H), 9.03 (s, 1H), 7.84-7.74 (m, 1H), 7.55-7.41 (m, 3H), 7.38-7.15 (m, 2H), 4.52 (d, J = 5.6 Hz, 2H), 3.94 (s, 3H). |
| 134 | 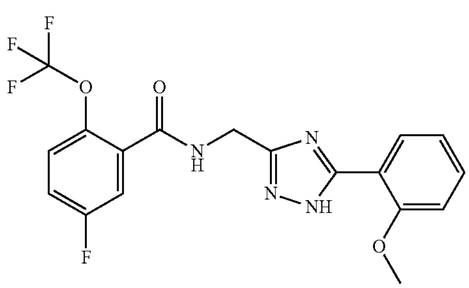 [SMILES: COc1ccccc1-c1nc(CNC(=O)c2cc(F)ccc2OC(F)(F)F)n[nH]1] | 411.1 | $^1$H NMR (400 MHz, DMSO) δ 13.55 (s, 1H), 9.03 (t, J = 5.6 Hz, 1H), 8.06 (dd, J = 7.7, 1.6 Hz, 1H), 7.53-7.39 (m, 4H), 7.19 (d, J = 8.3 Hz, 1H), 7.07 (d, J = 7.4 Hz, 1H), 4.51 (d, J = 5.7 Hz, 2H), 3.95 (s, 3H). |

Synthesis of N-((5-(3-methoxypyridin-2-yl)-1H-1,2,4-triazol-3-yl) methyl)-2-(trifluoro methoxy)benzamide (Compound 34)

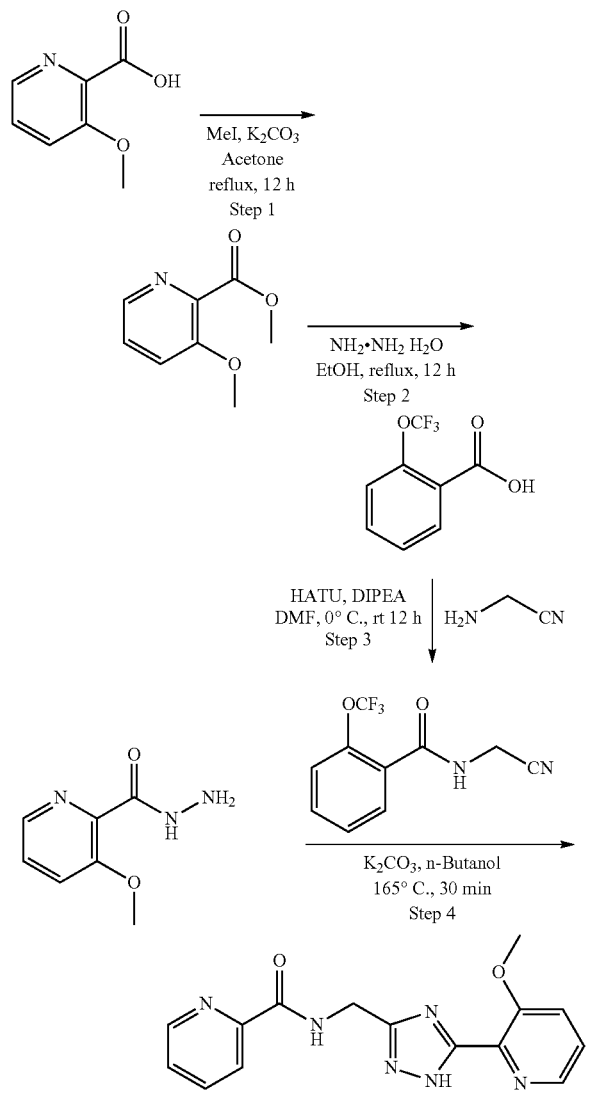

Step 1: methyl 3-methoxypicolinate

To a stirred solution of 3-methoxypicolinic acid (1 g, 7.19 mmol) in acetone (10 ml) at 0° C. was added $K_2CO_3$ (2.48 g, 17.97 mmol), followed by methyl iodide (2.23 g, 15.75 mmol). The mixture was stirred at room temperature for 12 h. After the completion of the reaction, the reaction mixture was concentrated and diluted with $H_2O$ (25 mL) and extracted with EtOAc (2×15 mL). The combined organic layer was dried over $Na_2SO_4$ and concentrated on rotavapour to get the crude compound. The crude product was purified by flash column chromatography to afford methyl 3-methoxypicolinate as yellow syrup (570 mg, 47.50%). $^1$H NMR (400 MHz, DMSO): δ 8.16 (dd, J=4.5, 1.1 Hz, 1H), 7.64 (d, J=8.6 Hz, 1H), 7.54 (dd, J=8.6, 4.5 Hz, 1H), 3.84 (s, 3H), 3.82 (s, 3H). LC-MS (ESI): m/z 168.1 (M+H)$^+$ Step 2: 3-methoxypicolinohydrazide

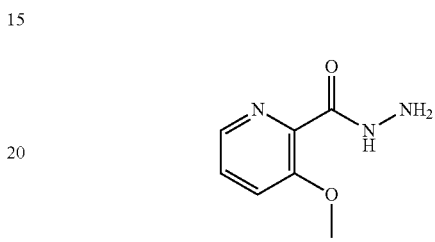

To a stirred solution of methyl 3-methoxypicolinate (560 mg, 3.33 mmol) in ethanol (10 mL) at room temperature was added hydrazine hydrate (213 mg, 6.66 mmol) and stirred at 70° C. for 12 h. After the completion of the reaction, the mixture was concentrated and the crude compound thus obtained was triturated with petroleum ether to afford 3-methoxypicolinohydrazide as brown syrup (530 mg, 94.6%). $^1$H NMR (400 MHz, DMSO): δ 9.40 (s, 1H), 8.10 (d, J=4.5 Hz, 1H), 7.53 (d, J=8.4 Hz, 1H), 7.43 (dd, J=8.5, 4.6 Hz, 1H), 4.43 (s, 2H), 3.79 (s, 3H). LC-MS (ESI): m/z 168.2 (M+H)$^+$ Step 3: N-(cyan methyl)-2-(trifluoro methoxy)benzamide

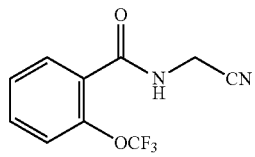 [SMILES: N#CCNC(=O)c1ccccc1OC(F)(F)F]

To a stirred to solution of 2-(trifluoro methoxy) benzoic acid (2 g, 9.7 mmol) in DMF (10 mL) was added HATU (5.5 g, 14.56 mmol), and DIPEA (3.76 g, 29.12 mmol) at 0° C. The resulting mixture was stirred for 10 min and 2-aminoacetonitrile 2 (897 mg, 9.70 mmol) was added and stirred at room temperature for 12 h. After the completion of the reaction, the reaction mixture was diluted with ice-cold water (100 mL) and extracted with EtOAc (2×20 mL). The combined organic layer was dried over $Na_2SO_4$ and concentrated under vacuum. The crude product obtained was purified by combi-flash column chromatography (eluent: 40% ethyl acetate in hexane) to afford N-(cyan methyl)-2-(trifluoro methoxy) benzamide as white solid (1.8 g, 82.19%) $^1$H NMR (400 MHz, DMSO): δ 9.18 (s, 1H), 7.65-7.60 (m, 2H), 7.48 (dd, J=14, 3.5 Hz, 2H), 4.30 (d, J=5.6 Hz 2H). LC-MS (ESI): m/z 245.1 (M+H)$^+$ Step 4: N-((5-(3-methoxypyridin-2-yl)-1H-1, 2, 4-triazol-3-yl) methyl)-2-(trifluoro methyl) Benzamide

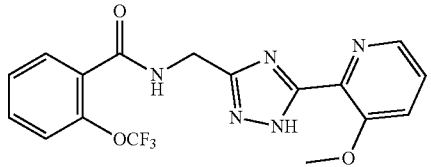 [SMILES: COc1cccnc1-c1nc(CNC(=O)c2ccccc2OC(F)(F)F)n[nH]1]

To a stirred solution N-(cyan methyl)-2-(trifluoro methoxy) benzamide in n-Butanol (2 mL) 3-methoxypicolinohydrazide (44.34 mg, 0.26 mmol) and $K_2CO_3$ (15.20 mg, 0.11 mmol) were added and allowed to stir at 165° C. under microwave for 30 min. After the completion of the reaction, the reaction mixture was diluted with cold water extracted with EtOAc (2×10 mL). The combined organic layer dried over $Na_2SO_4$ concentrated under vacuum to get the crude compound. The crude compound was purified by preparative TLC to afford the N-((5-(3-methoxypyridin-2-yl)-1H-1, 2, 4-triazol-3-yl) methyl)-2-(trifluoro methyl) Benzamide as off white solid (30 mg, 34.5%). $^1$H NMR (400 MHz, DMSO): δ 14.01 (s, 1H), 8.95 (s, 1H), 8.27 (s, 1H), 7.69-7.56 (m, 3H), 7.52-7.39 (m, 3H), 4.54 (s, 2H), 3.92 (s, 3H). LC-MS (ESI): m/z 394.1 (M+H)$^+$ Synthesis of 2-(difluoromethoxy)-N-(1-(5-(2-methoxyphenyl)-1H-1,2,4-triazol-3-yl) cyclopropyl) benzamide (Compound 118)

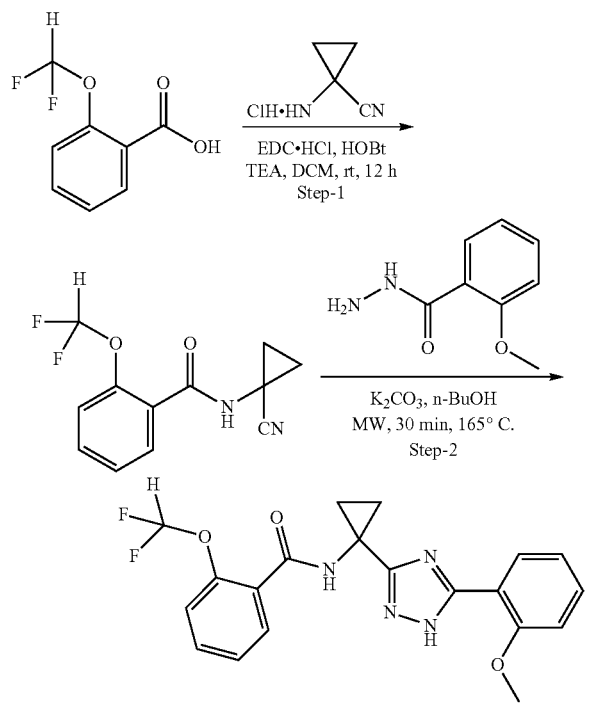

Step 1: N-(1-Cyanocyclopropyl)-2-(difluoro methoxy) benzamide

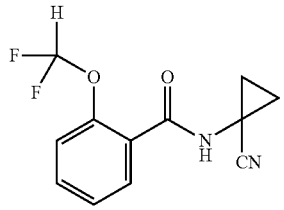 [SMILES: N#CC1(NC(=O)c2ccccc2OC(F)F)CC1]

To a stirred solution of 2-(difluoro methoxy) benzoic acid (1 g, 5.32 mmol) and 1-aminocyclopropane-1-carbonitrile hydrochloride (747 mg, 6.40 mmol) in DMF (20 mL) at 0° C. were added TEA (3.0 mL, 21.28 mmol), EDC.HCl (1.52 mg, 7.98 mmol) and HOBt (1.07 mg, 7.98 mmol). Then the resulting reaction mixture was stirred at room temperature for 12 h. After the completion of reaction, the mixture was diluted with ice cold water and extracted with EtOAc. The combined organic layers was washed with ice cold water (3×100 mL), brine (2×100 mL) and dried over $Na_2SO_4$. Concentration followed by the purification of the crude product using flash column chromatography to afford N-(1-cyanocyclopropyl)-2-(difluoro methoxy) benzamide (560 mg, yield: 42%) as an off-white solid. $^1$H NMR (400 MHz, DMSO): δ 9.20 (s, 1H), 7.51-7.56 (m, 2H), 6.94-7.34 (m, 3H), 1.53-1.57 (m, 2H), 1.18-1.22 (m, 2H). LC-MS (ESI): m/z 400.1 (M+H)$^+$ Step 2: 2-(Difluoromethoxy)-N-(1-(5-(2-methoxyphenyl)-1H-1,2,4-triazol-3-yl) cyclopropyl) benzamide

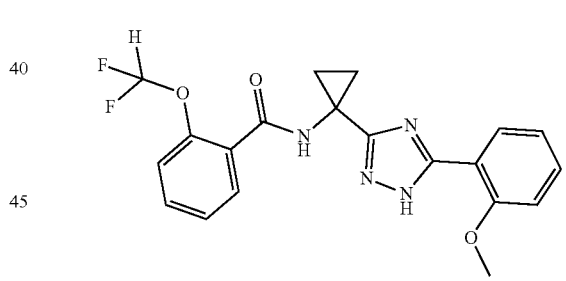

To a stirred solution of N-(1-cyanocyclopropyl)-2-(difluoro methoxy) benzamide (200 mg, 0.79 mmol), 2-methoxybenzohydrazide (200 mg, 1.2 mmol) in n-BuOH was added $K_2CO_3$ (100 mg, 0.72 mmol) at room temperature. The resulting reaction mixture was heated at 120° C. for 16 h. Upon completion of the reaction, the mixture was concentrated under vacuum and diluted with water and extracted with EtOAc. The organics were washed with brine, water and finally dried over $Na_2SO_4$. Concentration on rotavapor followed by purification on flash column chromatography afforded 2-(difluoromethoxy)-N-(1-(5-(2-methoxyphenyl)-1H-1,2,4-triazol-3-yl) cyclopropyl) benzamide (50 mg, yield: 16%) as an off white solid. $^1$H NMR (400 MHz, DMSO): δ 13.37 (s, 1H), 9.04 (s, 1H), 7.99 (d, J=7.6 Hz, 1H), 7.58 (d, J=7.6 Hz, 1H), 7.52 (t, J=8.0 Hz, 1H), 7.44 (t, J=7.2 Hz, 1H), 6.94-7.37 (m, 6H), 3.93 (s, 3H), 1.41 (s, 2H), 1.20-.132 (m, 4H). LC-MS (ESI): m/z 400.1 (M+H)$^+$ Synthesis of 2-(difluoromethoxy)-5-fluoro-N-((5-(2-methoxyphenyl)-1H-1,2,4-triazol-3-yl) methyl) benzamide (Compound 138)

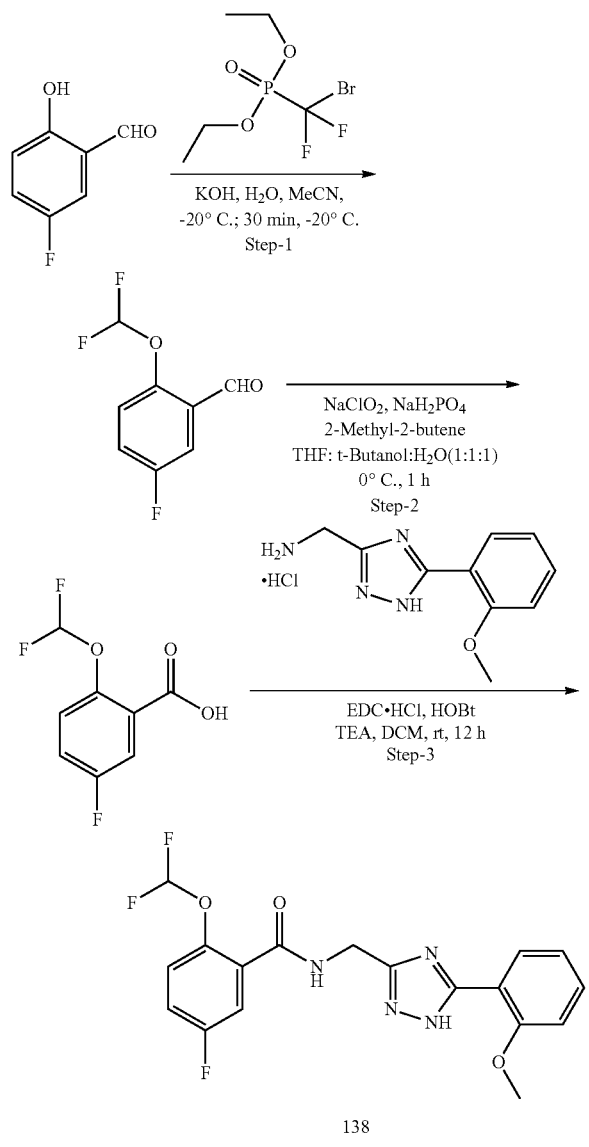

138

Step 1: 2-(difluoro methoxy)-5-fluorobenzaldehyde

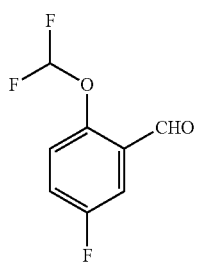 [SMILES: O=Cc1cc(F)ccc1OC(F)F]

To a stirred solution of KOH (8.0 9 g, 142.8 mmol) in acetonitrile (20 mL) and water (20 mL) at −20° C., was added 4-fluoro-2-hydroxy benzaldehyde (1 g, 7.14 mmol) followed by dropwise addition of diethyl (bromodifluoromethyl) phosphonate (3.80 g, 14.28 mmol) over a period of 30 min. After the completion of reaction, the mixture was diluted with EtOAc (20 mL), organic layer was separated and dried over $Na_2SO_4$. Concentration of the organics followed by purification of the crude compound by flash column chromatography (eluent: 10% EtOAc in Hexane) afforded 2-(difluoro methoxy)-5-fluorobenzaldehyde as yellow syrup (700 mg, 51.8%)$^1$H NMR (400 MHz, DMSO): δ 10.20 (d, J=2.8 Hz, 1H), 7.65 (ddd, J=9.0, 8.0, 3.3 Hz, 1H), 7.59 (dd, J=8.3, 3.2 Hz, 1H), 7.46 (dd, J=9.0, 4.2 Hz, 1H), 7.32 (t, J=73.6 Hz, 1H).

Step 2: 2-(difluoro methoxy)-5-fluorobenzoic acid

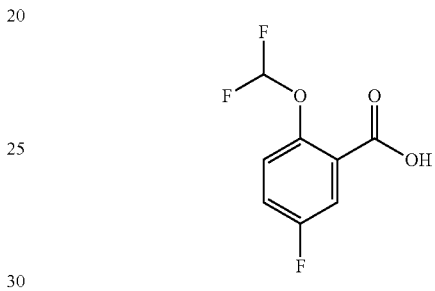

To a vigorously stirred solution of 2-(difluoro methoxy)-5-fluorobenzaldehyde (500 mg, 2.62 mmol) in THF:t-butanol:$H_2O$ (10 mL) at 0° C., was added sodium phosphate monobasic (1.02 g, 6.56 mmol) followed sequentially by 2-methyl-2-butene (473.4 mL, 2.29 mmol) and $NaClO_2$. The mixture allowed to warm up to room temperature and stirred for 1 h. After the completion of the reaction, the reaction mixture acidified with 1N HCl (5 mL) and extracted with EtOAc (2×25 mL). The combined organic layers was dried over $Na_2SO_4$ and concentrated to obtain 2-(difluoro methoxy)-5-fluorobenzoic acid as white solid (400 mg, 73.93%)$^1$H NMR (400 MHz, DMSO): δ 13.49 (s, 1H), 7.61 (dd, J=8.7, 3.2 Hz, 1H), 7.49 (ddd, J=8.9, 8.0, 3.3 Hz, 1H), 7.34 (dd, J=9.0, 4.5 Hz, 1H), 7.10 (t, J=74.3 Hz, 1H). GC-MS (ESI): m/z 206 (M)+

Step 3: 2-(difluoromethoxy)-5-fluoro-N-((5-(2-methoxyphenyl)-1H-1,2,4-triazol-3-yl) methyl) benzamide

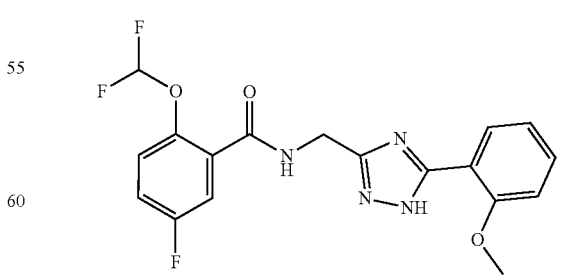

To a stirred to solution of 2-(difluoro methoxy)-5-fluorobenzoic acid (100 mg, 0.48 mmol) in dichloromethane (10 mL) at 0° C., were added EDC.HCl (113.02 mg, 0.72 mmol), HOBt (98.37 mg, 0.72 mmol) and TEA (147.07 mg, 1.45 mmol). The resulting mixture was stirred for 10 min followed by the addition of (5-(2-methoxyphenyl)-1H-1, 2,4-triazol-3-yl) methanamine hydrochloride (139.8 mg, 0.58 mmol). The mixture was warmed up to room temperature and stirred for 12 h. After the completion, reaction mixture was washed sequentially once with saturated $NH_4Cl$ (20 mL), saturated $NaHCO_3$ solution (20 mL) and brine (20 mL). The combined organic layer was dried over $Na_2SO_4$ and concentrated. The crude product thus obtained was purified by flash column chromatography (eluent: 40% ethyl acetate in hexane) to afford the compound 2-(difluoromethoxy)-5-fluoro-N-((5-(2-methoxyphenyl)-1H-1,2,4-triazol-3-yl)methyl)benzamide as off white solid (60 mg, 31.5%). $^1$H NMR (400 MHz, DMSO): δ 13.56 (s, 1H), 8.89 (s, 1H), 8.06 (d, J=7.6 Hz, 1H), 7.49-7.36 (m, 4H), 7.31 (t, J=4.3 Hz, 1H), 7.19 (d, J=8.4 Hz, 1H), 7.12 (t, J=68 Hz, 1H) 7.07 (t, J=7.5 Hz, 1H), 6.94 (s, 2H), 4.53 (d, J=5.6 Hz, 2H), 3.95 (s, 3H). LC-MS (ESI): m/z 393.3 (M+H)$^+$ Synthesis of 2-(difluoromethoxy)-5-fluoro-N-((5-(5-fluoro-2-methoxyphenyl)-1H-1,2,4-triazol-3-yl)methyl)benzamide

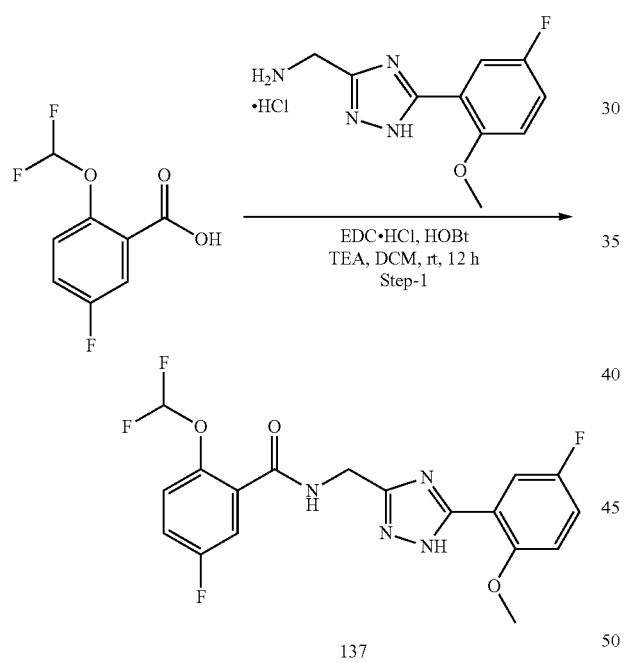

137

To a stirred to solution of 2-(difluoro methoxy)-5-fluorobenzoic acid (100 mg, 0.48 mmol) in dichloromethane (10 ml) at 0° C., were added EDC.HCl (113.02 mg, 0.72 mmol), HOBt (98.37 mg, 0.72 mmol) and TEA (147.07 mg, 1.45 mmol). The resulting mixture was stirred for 10 min followed by the addition of (5-(5-fluoro-2-methoxyphenyl)-1H-1,2,4-triazol-3-yl) methoxamine hydrochloride (129.36 mg, 0.58 mmol). The mixture was warmed up to room temperature and stirred for 12 h. Upon completion of the reaction, reaction mixture was washed sequentially once with saturated $NH_4Cl$ (20 mL), saturated $NaHCO_3$ solution (20 mL) and brine (20 mL). The combined organic layer was dried over $Na_2SO_4$ and concentrated. The crude product thus obtained was purified by flash column chromatography (eluent: 40% ethyl acetate in hexane) to afford 2-(difluoromethoxy)-5-fluoro-N-((5-(5-fluoro-2-methoxyphenyl)-1H-1,2,4-triazol-3-yl) methyl) benzamide off white solid (40 mg, 20.10%). $^1$H NMR (400 MHz, DMSO): δ 13.70 (s, 1H), 8.90 (s, 1H), 7.77 (s, 1H), 7.46-7.37 (m, 2H), 7.31 (t, J=4.4 Hz, 2H), 7.21 (dd, J=8.8, 4.3 Hz, 1H), 7.13 (t, J=64 Hz, 1H), 4.53 (d, J=5.5 Hz, 2H), 3.94 (s, 3H). LC-MS (ESI): m/z 411.1 (M+H)$^+$.

Synthesis of 2-(difluoromethoxy)-N-((5-(5-fluoro-2-methoxyphenyl)-1H-1,2,4-triazol-3-yl)methyl)nicotinamide (Compound 143) AND 2-(difluoromethoxy)-N-((5-(2-methoxyphenyl)-1H-1,2,4-triazol-3-yl)methyl)nicotinamide (Compound 144)

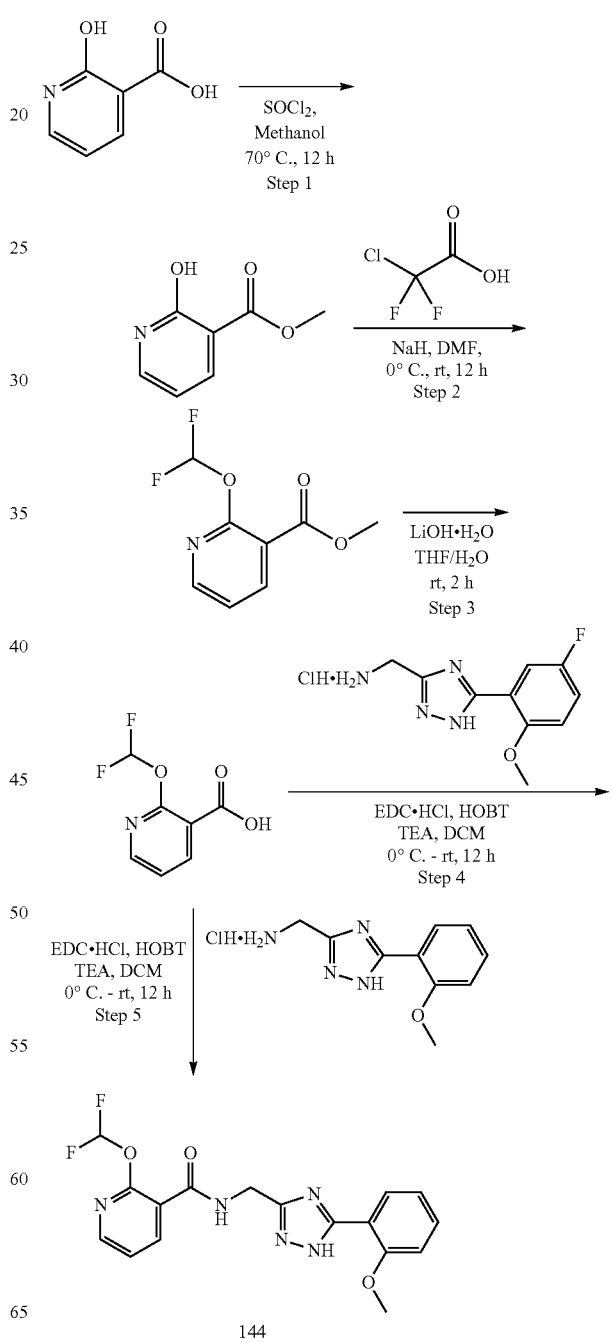

144

-continued

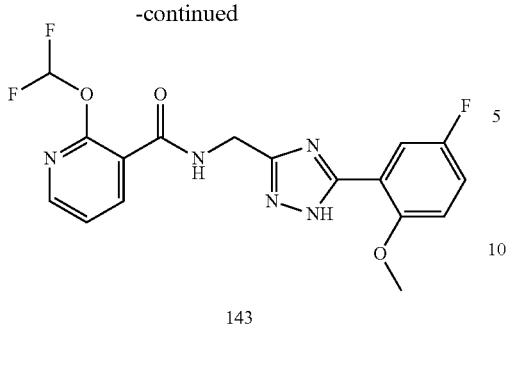

143

Step 1: methyl 2-hydroxynicotinate

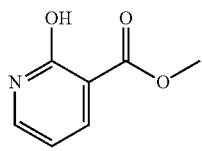

To a stirred solution of 2-hydroxynicotinic acid (5 g, 27.8 mmol), in methanol (75 mL), at 0° C., thionylchloride (5 mL) was added and stirred at 75° C. for 12 h. After the completion of reaction, the reaction mixture was concentrated under vacuum to obtain the crude product. The mixture was basified with saturated NaHCO$_3$ solution (20 mL) and extracted with 10% methanol in dichloromethane (2×25 mL). The combined organic layer was dried over Na$_2$SO$_4$, and concentrated. under reduced pressure to afford methyl 2-hydroxynicotinate as off-white solid (2.3 g, 41.8%). $^1$H NMR (400 MHz, DMSO): δ 12.08 (s, 1H), 8.04 (dd, J=7.1, 2.2 Hz, 1H), 7.65 (dd, J=6.3, 2.2 Hz, 1H), 6.25 (t, J=6.7 Hz, 1H), 3.71 (s, 3H). LC-MS (ESI): m/z 154.1 (M+H)

Step 2: methyl 2-(difluoro methoxy) nicotinate

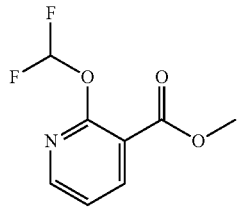

To a stirred solution of methyl 2-hydroxynicotinate (1.9 g, 12.4 mmol) in DMF at 0° C. was added sodium hydride (357 mg, 14.9 mmol) portion wise and stirred for 10 min, followed by the addition of 2-chloro-2,2-difluoroacetic acid (1.94 g, 14.9 mmol) and allowed to stir at 125° C. for 2 h. After the completion of the reaction, the mixture was diluted with ice-cold water (25 mL) and extracted with 10% methanol in dichloromethane (2×10 mL)). The combined organic layer was concentrated under reduced pressure to get the crude compound. It was purified by flash column chromatography to afford methyl 2-(difluoromethoxy) nicotinate as pale brown solid. (500 mg, 19.84%). $^1$H NMR (400 MHz, DMSO): δ 8.48 (dd, J=4.9, 1.9 Hz, 1H), 8.33 (dd, J=7.6, 1.9 Hz, 1H), 7.79 (t, J=72.2 Hz, 2H), 7.42 (dd, J=7.6, 4.9 Hz, 1H), 3.87 (s, 3H). LC-MS (ESI): m/z 154.1 (M+H)

Step 3: 2-(difluoro methoxy) nicotinic acid

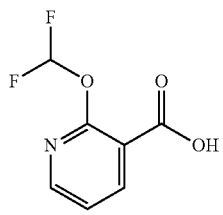 [SMILES: O=C(O)c1cccnc1OC(F)F]

To a stirred solution of methyl 2-(difluoro methoxy) nicotinate (260 mg, 1.27 mmol) in THF:H$_2$O (10 mL: 5 mL) at 0° C. was added LiOH (122.8 mg, 5.1 mmol) and the reaction mixture was allowed to stir at room temperature for 2 h. After the completion of reaction, the reaction mixture was concentrated, diluted with H$_2$O (10 mL) and extracted with EtOAc (2×10 mL). The aqueous layer was separated and acidified with 1N HCl solution (5 mL) and, then extracted with 10% methanol in dichloromethane (2×15 mL). The combined organic layer was dried over Na$_2$SO$_4$ and concentrated under vacuum to afford 2-(difluoromethoxy) nicotinic acid as off-white solid (60 mg, 24.7%). $^1$H NMR (400 MHz, DMSO): δ 13.44 (s, 1H), 8.43 (dd, J=4.9, 1.9 Hz, 1H), 8.30 (dd, J=7.6, 1.9 Hz, 1H), 7.78 (t, J=72.4 Hz, 1H), 7.39 (dd, J=7.6, 4.9 Hz, 1H).

Step 4: 2-(difluoro methoxy)-N-((5-(5-fluoro-2-methoxyphenyl)-1H-1, 2, 4-triazol-3-yl) methyl) nicotinamide (Compound 143)

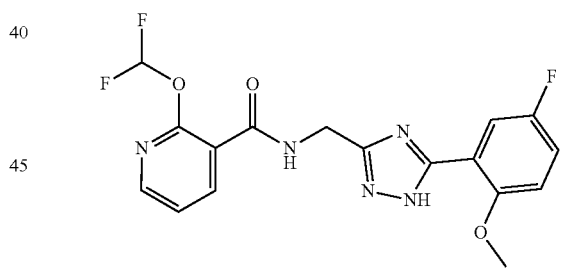

To a stirred to solution of 2-(difluoro methoxy) nicotinic acid (70 mg, 0.37 mmol) in CH$_2$Cl$_2$ (10 mL) at 0° C., was added EDC.HCl (106.4 mg, 0.55 mmol), HOBt (75.01 mg, 0.55 mmol) and triethyl amine (112 mg, 1.11 mmol). The resulting mixture was stirred for 10 min and (5-(5-fluoro-2-methoxyphenyl)-1H-1, 2, 4-triazol-3-yl) methanamine hydrochloride (95.74 mg, 0.37 mmol) was added and stirred at room temperature for 12 h. After the completion of the reaction, the mixture was washed sequentially with saturated NH$_4$Cl (20 mL), saturated NaHCO$_3$ solution (20 mL) and brine (20 mL). The combined organic layer was dried over Na$_2$SO$_4$ and concentrated to get the crude compound. The crude obtained then was purified by flash column chromatography (eluent: 50% ethyl acetate in hexane) to afford product 2-(difluoro methoxy)-N-((5-(5-fluoro-2-methoxyphenyl)-1H-1, 2, 4-triazol-3-yl) methyl) nicotinamide as off-white solid (60 mg, 41.23%)$^1$H NMR (400

MHz, DMSO): δ 13.73 (s, 1H), 8.83 (s, 1H), 8.35 (dd, J=4.9, 1.9 Hz, 1H), 8.11 (dd, J=7.5, 1.8 Hz, 1H), 7.74 (t, J=72.1 Hz, 1H), 7.81 (dd, J=9.4, 3.2 Hz, 1H), 7.42-7.29 (m, 2H), 7.22 (dd, J=9.1, 4.5 Hz, 1H), 4.56 (d, J=5.5 Hz, 2H), 3.95 (s, 3H). LC-MS (ESI): m/z 394.2 (M+H)

Step 5: 2-(difluoromethoxy)-N-((5-(2-methoxyphenyl)-1H-1,2,4-triazol-3-yl) methyl) nicotinamide (Compound 144)

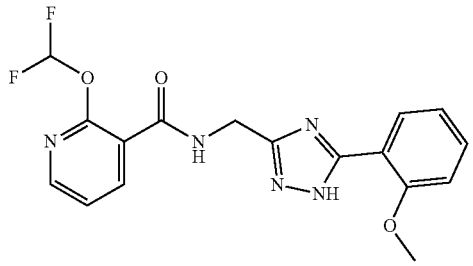 [SMILES: COc1ccccc1-c1nc(CNC(=O)c2cccnc2OC(F)F)n[nH]1]

To a stirred to solution of 2-(difluoro methoxy) nicotinic acid (50 mg, 0.26 mmol) in CH$_2$Cl$_2$ (10 mL) at 0° C. were added, 1-Ethyl-3-(3-dimethylaminopropyl) carbodiimide, (76.02 mg, 0.39 mmol), Hydroxybenzotriazole (53.58 mg, 0.39 mmol) and triethyl amine (80.10 mg, 0.79 mmol). The resulting mixture was stirred for 10 min followed by the addition of (5-(2-methoxyphenyl)-1H-1,2,4-triazol-3-yl) methanamine hydrochloride (63.6 mg, 0.26 mmol) and stirred at room temperature for 12 h. After the completion of the reaction, the mixture was diluted with aqueous NH$_4$Cl solution and extracted with dichloromethane. The organic was sequentially washed with 1N HCl, aqueous NH$_4$CO$_3$ and brine. The organic layer was dried over MgSO$_4$, concentrated under vacuum and the crude compound thus obtained was purified by flash column chromatography to afford product as a white solid (60 mg 0.76%).1H NMR (400 MHz, DMSO): δ 13.58 (s, 1H), 8.82 (s, 1H), 8.35 (dd, J=4.9, 1.8 Hz, 1H), 8.09 (t, J=8.1 Hz, 2H), 7.73 (t, J=72.1 Hz, 1H), 7.46 (t, J=7.5 Hz, 1H), 7.37 (dd, J=7.5, 4.9 Hz, 1H), 7.19 (d, J=8.4 Hz, 1H), 7.07 (t, J=7.5 Hz, 1H), 4.56 (d, J=5.4 Hz, 2H), 3.95 (s, 3H). LC-MS (ESI): m/z 376.1 (M+H)

The following compounds in Table 10 were prepared using similar procedures to those described above using the appropriate starting materials.

TABLE 10

| Example/ Compound Nos. | Structure | LC-MS [M + H]+ (m/z) | NMR Data |
|---|---|---|---|
| 139 | 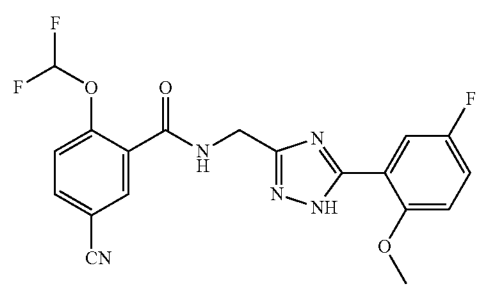 [SMILES: COc1ccc(F)cc1-c1nc(CNC(=O)c2cc(C#N)ccc2OC(F)F)n[nH]1] | 418.1 | $^1$H NMR (400 MHz, DMSO): δ 13.71 (s, 1H), 8.98 (d, J = 5.2 Hz, 1H), 8.04-8.01 (m, 1H), 7.89 (dd, J = 9.2, 3.2 Hz, 1H), 7.43 (d, J = 8.4 Hz, 1H), 7.35-7.29 (m, 2H), 7.23-7.20 (m, 1H), 7.37 (t, J = 73.2 Hz, 1H), 4.53 (d, J = 5.2 Hz, 2H), 3.94 (s, 3H) |
| 140 | 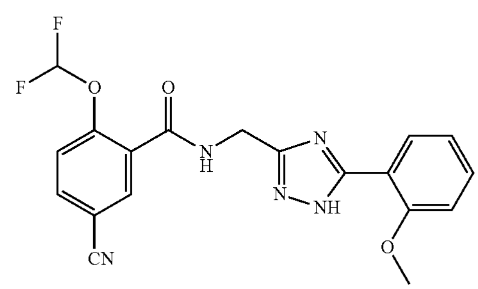 [SMILES: COc1ccccc1-c1nc(CNC(=O)c2cc(C#N)ccc2OC(F)F)n[nH]1] | 400.1 | $^1$H NMR (400 MHz, DMSO): δ 13.71 (s, 1H), 8.98 (d, J = 5.2 Hz, 1H), 8.04-8.01 (m, 1H), 7.89 (dd, J = 9.2, 3.2 Hz, 1H), 7.43 (d, J = 8.4 Hz, 1H), 7.35-7.29 (m, 3H), 7.23-7.20 (m, 1H), 7.37 (t, J = 73.2 Hz, 1H), 4.53 (d, J = 5.2 Hz, 2H), 3.94 (s, 3H) |
| 141 | 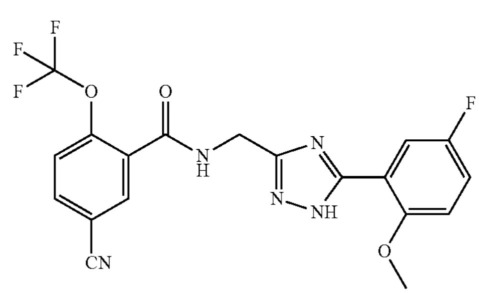 [SMILES: COc1ccc(F)cc1-c1nc(CNC(=O)c2cc(C#N)ccc2OC(F)(F)F)n[nH]1] | 436.1 | |

TABLE 10-continued

| Example/ Compound Nos. | Structure | LC-MS [M + H]+ (m/z) | NMR Data |
|---|---|---|---|
| 142 | 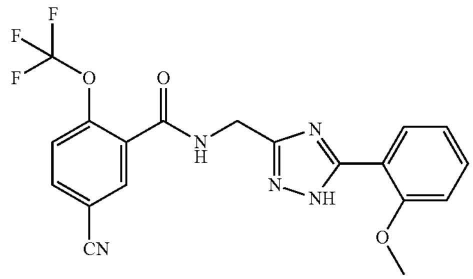 [SMILES: COc1ccccc1-c1nc(CNC(=O)c2cc(C#N)ccc2OC(F)(F)F)n[nH]1] | 418.1 | |
| 145 | 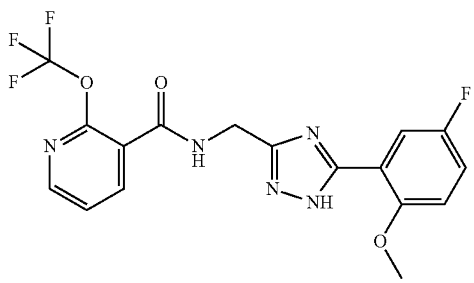 [SMILES: COc1ccc(F)cc1-c1nc(CNC(=O)c2cccnc2OC(F)(F)F)n[nH]1] | 412.1 | |
| 146 | 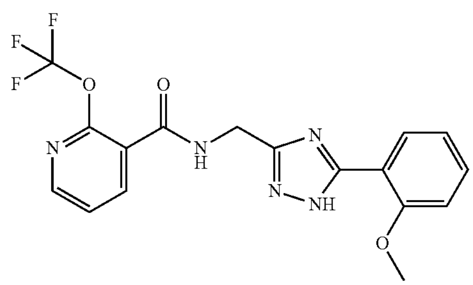 [SMILES: COc1ccccc1-c1nc(CNC(=O)c2cccnc2OC(F)(F)F)n[nH]1] | 394.0 | |
| 147 | 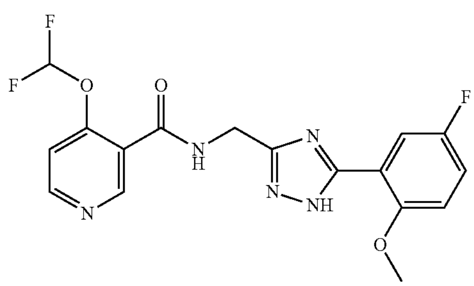 [SMILES: COc1ccc(F)cc1-c1nc(CNC(=O)c2cnccc2OC(F)F)n[nH]1] | 394.1 | ¹H NMR (400 MHz, DMSO): δ 13.74 (s, 1H), 10.33 (s, 1H), 8.83 (d, J = 2.4 Hz, 1H), 8.21 (dd, J = 7.8, 2.4 Hz, 1H), 7.78 (dd, J = 65.0, 52.0 Hz, 2H), 7.32 (d, J = 5.5 Hz, 1H), 7.26-7.17 (m, 1H), 6.58 (d, J = 7.8 Hz, 1H), 4.61 (d, J = 5.3 Hz, 2H), 3.94 (s, 3H) |
| 148 | 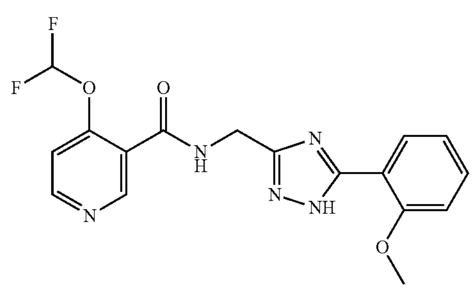 [SMILES: COc1ccccc1-c1nc(CNC(=O)c2cnccc2OC(F)F)n[nH]1] | 376.1 | ¹H NMR (400 MHz, DMSO): δ 13.60 (s, 1H), 10.32 (s, 1H), 8.83 (d, J = 2.5 Hz, 1H), 8.21 (dd, J = 7.8, 2.5 Hz, 1H), 8.04 (s, 1H), 7.79 (t, J = 58.5 Hz, 1H), 7.46 (t, J = 7.9 Hz, 1H), 7.19 (d, J = 8.5 Hz, 1H), 7.08 (t, J = 7.6 Hz, 1H), 6.58 (d, J = 7.8 Hz, 1H), 4.60 (d, J = 5.3 Hz, 2H), 3.94 (s, 2H) |

TABLE 10-continued
| Example/ Compound Nos. | Structure | LC-MS [M + H]+ (m/z) | NMR Data |
|---|---|---|---|
| 149 | 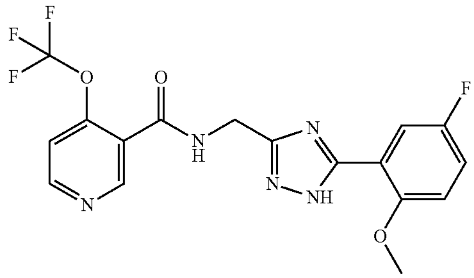 [SMILES: COc1ccc(F)cc1-c1nc(CNC(=O)c2cnccc2OC(F)(F)F)n[nH]1] | 412.0 | |
| 150 | 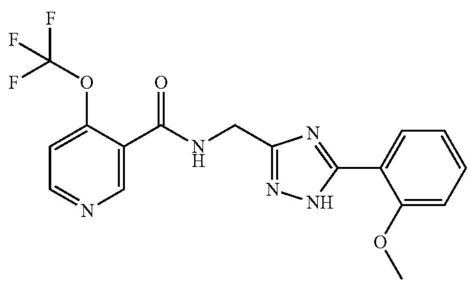 [SMILES: COc1ccccc1-c1nc(CNC(=O)c2cnccc2OC(F)(F)F)n[nH]1] | 394.1 | |
Synthesis of 2-(difluoromethoxy)-3-fluoro-N-((5-(5-fluoro-2-methoxyphenyl)-1H-1,2,4-triazol-3-yl)methyl) benzamide (Compound 135) AND 2-(difluoromethoxy)-3-fluoro-N-((5-(2-methoxyphenyl)-1H-1,2,4-triazol-3-yl) methyl) benzamide (Compound 136)
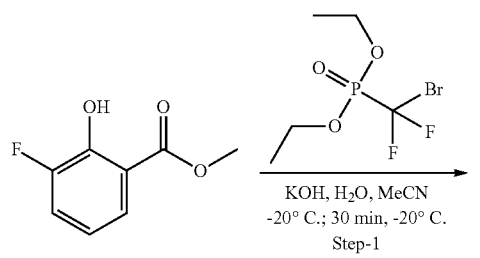
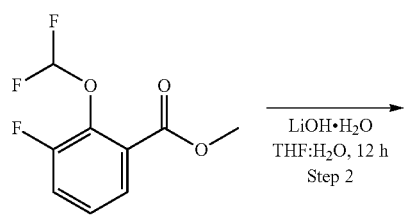
-continued
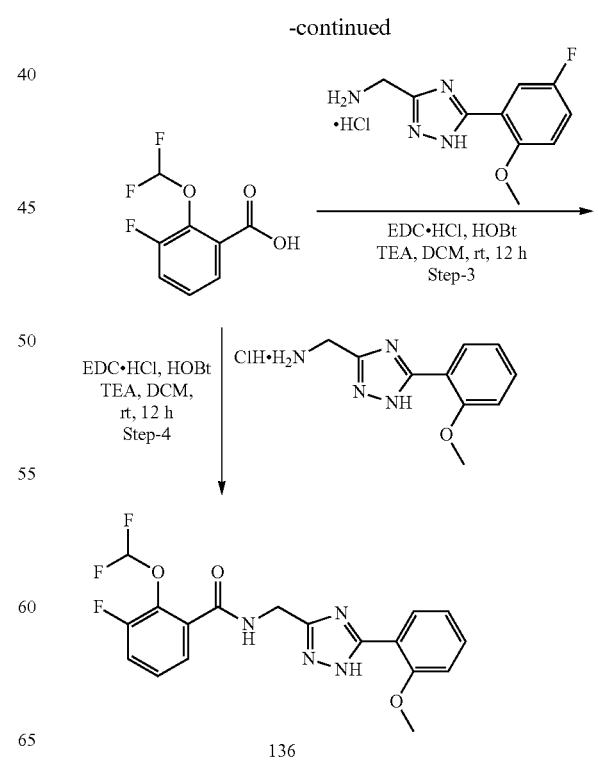

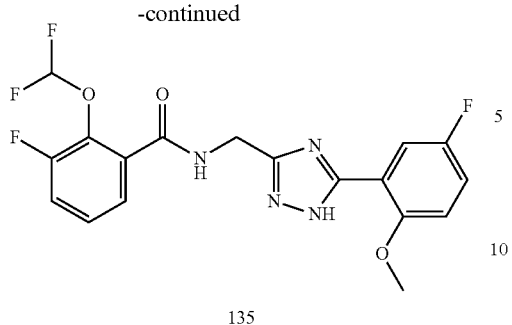

135

Step 1: methyl 2-(difluoro methoxy)-3-fluorobenzoate

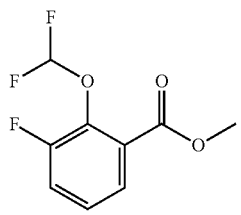

To a cold stirred solution of KOH (6.58 g, 117.5 mmol) in water (30 mL), was added acetonitrile (30 mL) and the solution was further cooled to −20° C. To the resultant mixture was added methyl 2-fluoro-6-hydroxybenzoate (1 g, 5.87 mmol) followed by drop wise addition of diethyl (bromodifluoromethyl) phosphonate (3.13 g, 11.7 mmol) and the reaction mixture allowed to stir at −20 C for 30 min. After the completion of reaction, the reaction mixture diluted with water and extracted with ethyl acetate. The organic layer was dried over MgSO$_4$ and concentrated under vacuum. The crude compound was purified by flash column chromatography to afford the compound methyl 2-(difluoro methoxy)-3-fluorobenzoate as yellow syrup (520 mg, 40.31%). $^1$H NMR (400 MHz, DMSO): δ 7.69-7.64 (m, 2H), 7.47-7.43 (m, 1H), 7.12 (t, J=73.6 Hz, 1H), 3.98 (s, 3H).

Step 2: 2-(difluoro methoxy)-3-fluorobenzoic acid

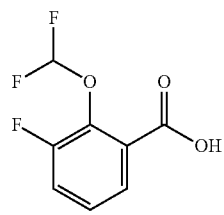 [SMILES: O=C(O)c1cccc(F)c1OC(F)F]

To a stirred solution of methyl 2-(difluoro methoxy)-6-fluorobenzoate (500 mg, 2.27 mmol) in THF:H$_2$O (2:1) at 0° C., was added LiOH (954.5 mg, 22.7 mmol) and allowed to stir at room temperature for 12 h. After the completion of reaction, the reaction mixture was acidified with 1N HCl, then extracted with 10% methanol in CH$_2$Cl$_2$, the organic layer was dried over MgSO$_4$ and concentrated under vacuum, to afford 2-(difluoromethoxy)-3-fluorobenzoic acid as a off-white solid. (210 mg, 44.8%). $^1$H NMR (400 MHz, DMSO): δ 13.53 (s, 1H), 7.70-7.57 (m, 2H), 7.44 (dt, J=13.2, 6.6 Hz, 1H), 7.10 (t, J=73.8 Hz, 1H).

Step 3: 2-(difluoromethoxy)-3-fluoro-N-((5-(5-fluoro-2-methoxyphenyl)-1H-1,2,4-triazol-3-yl) methyl) benzamide (Compound 135)

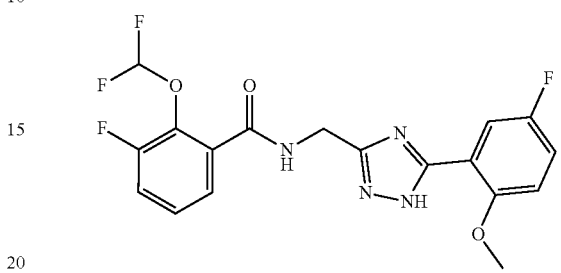

To a stirred to solution of 2-(difluoro methoxy)-3-fluorobenzoic acid (100 mg, 0.48 mmol) in CH$_2$Cl$_2$ (10 mL) at 0° C. was added EDC.HCl (139.07 mg, 0.72 mmol), HOBt (111.50 mg, 0.72 mmol) and triethyl amine (147 mg, 1.45 mmol). The resulting mixture was stirred for 10 min and (5-(5-fluoro-2-methoxyphenyl)-1H-1, 2, 4-triazol-3-yl) methanamine hydrochloride (125 mg, 0.48 mmol) was added and stirred at room temperature for 12 h. After the completion of the reaction, the mixture was diluted with aqueous NH$_4$Cl solution and extracted with CH$_2$Cl$_2$. The organic layer was then sequentially washed with 1N HCl, aqeuous NH$_4$CO$_3$ and brine. The organic layer was then dried over MgSO$_4$, concentrated under vacuum to afford the crude product. It was then purified by flash column chromatography to afford product 2-(difluoromethoxy)-3-fluoro-N-((5-(5-fluoro-2-methoxyphenyl)-1H-1,2,4-triazol-3-yl) methyl) benzamide as off-white solid (70 mg, 35.17 $^1$H NMR (400 MHz, DMSO): δ 13.71 (s, 1H), 8.98 (d, J=5.2 Hz, 1H), 8.04-8.01 (m, 1H), 7.89 (dd, J=9.2, 3.2 Hz, 1H), 7.43 (d, J=8.4 Hz, 1H), 7.35-7.29 (m, 2H), 7.23-7.20 (m, 1H), 7.37 (t, J=73.2 Hz, 1H), 4.53 (d, J=5.2 Hz, 2H), 3.94 (s, 3H)

Step 4: 2-(difluoromethoxy)-6-fluoro-N-((5-(2-methoxyphenyl)-1H-1,2,4-triazol-3-yl) methyl) benzamide (Compound 36)

To a stirred to solution of 2-(difluoro methoxy)-3-fluorobenzoic acid (100 mg, 0.48 mmol) in dichloromethane (10 mL at 0° C., was added EDC.HCl (139.07 mg, 0.72 mmol), HOBt (111.50 mg, 0.72 mmol) and triethyl amine (147 mg, 1.45 mmol). The resulting mixture was stirred for 10 min and ((5-(2-methoxyphenyl)-1H-1,2,4-triazol-3-yl) methanamine hydrochloride (116.53 mg, 0.48 mmol) was added and stirred at room temperature for 12 h. After the completion of the reaction, the mixture was diluted with aqueous NH$_4$Cl solution and extracted with CH$_2$Cl$_2$. The organic layer was then sequentially washed with 1N HCl, aqueous NH$_4$CO$_3$ and brine. The organic layer was then dried over MgSO$_4$ and concentrated to obtain the crude product. The crude compound was purified by flash column chromatography to afford product 2-(difluoromethoxy)-6-fluoro-N-((5-(2-methoxyphenyl)-1H-1,2,4-triazol-3-yl) methyl) benzamide as white solid (70 mg, 36.75%). $^1$H NMR (400 MHz, DMSO): δ 13.55 (s, 1H), 8.97 (s, 1H), 8.06 (d, J=7.7 Hz, 1H), 7.56-7.38 (m, 4H), 7.12 (ddd, J=67.7, 53.3, 45.4 Hz, 3H), 4.52 (d, J=5.6 Hz, 2H), 3.95 (s, 3H). LC-MS (ESI): m/z 393.29 (M+H)

Example of N-((5-(5-fluoro-2-methoxyphenyl)-1H-1,2,4-triazol-3-yl) methyl)-2-(trifluoro methoxy) benzamide (Compound 127)

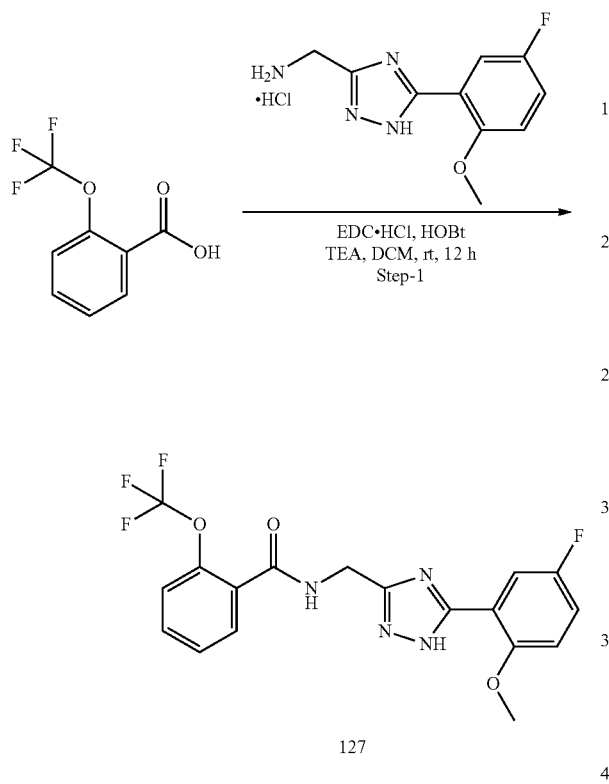

127

To a stirred to solution of 2-(trifluoro methoxy) benzoic acid (250 mg, 1.21 mmol) in CH$_2$Cl$_2$ (10 mL) at 0° C., was added EDC.HCl (348.93 mg, 1.82 mmol), HOBt (278.72 mg, 1.82 mmol), triethyl amine (367.68 mg, 3.63 mmol). The resulting mixture was stirred for 10 min and (5-(5-fluoro-2-methoxyphenyl)-1H-1, 2, 4-triazol-3-yl) methanamine hydrochloride (313.12 mg, 1.21 mmol) was added and further stirred at room temperature for 12 h. After the completion of the reaction, the mixture was diluted with aqueous NH$_4$Cl solution and extracted with CH$_2$Cl$_2$. The organic layer was then sequentially washed with 1N HCl, aqueous NH$_4$CO$_3$ and brine. It was then dried over MgSO$_4$ and concentrated under vacuum to afford the crude compound, which was purified by flash column chromatography to afford product N-((5-(5-fluoro-2-methoxyphenyl)-1H-1, 2,4-triazol-3-yl) methyl)-2-(trifluoromethoxy) benzamide as a off-white solid (300 mg, 60%). $^1$H NMR (400 MHz, DMSO): δ 13.68 (s, 1H), 8.92 (s, 1H), 7.79 (d, J=7.8 Hz, 1H), 7.60 (dd, J=16.6, 7.6 Hz, 2H), 7.45 (dd, J=21.1, 7.7 Hz, 2H), 7.32 (s, 1H), 7.22 (s, 1H), 4.52 (d, J=5.3 Hz, 2H), 3.94 (s, 3H). LC-MS (ESI): m/z 411.24 (M+H)

Synthesis of 2-(difluoromethoxy)-N-((5-(2-hydroxyphenyl)-1H-1,2,4-triazol-3-yl) methyl) benzamide (Compound 60)

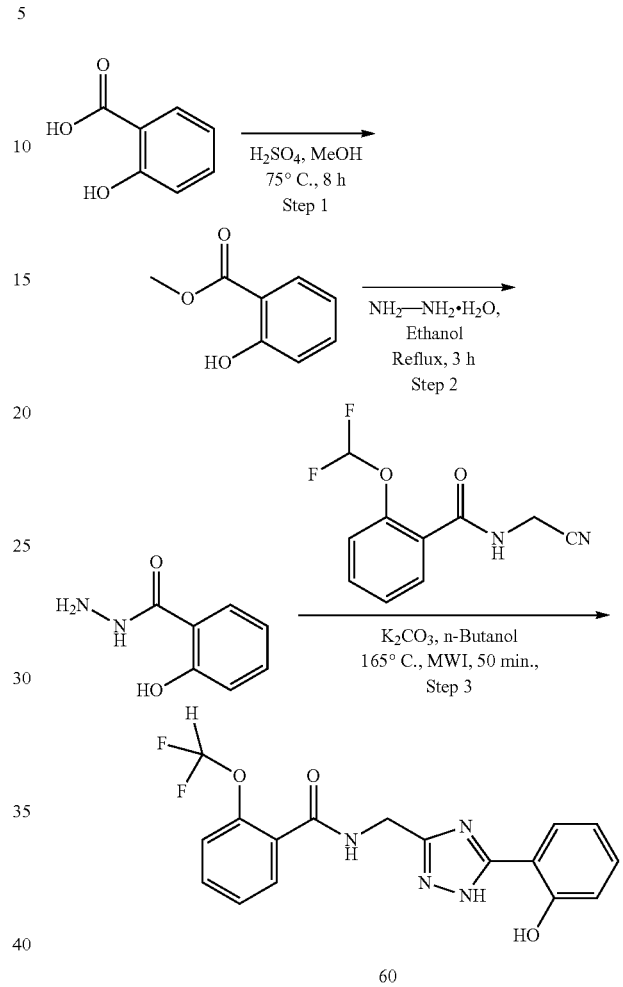

60

Step 1: Methyl 2-hydroxybenzoate

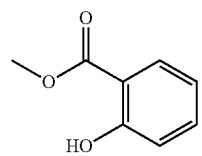

To a stirred solution of 2-hydroxybenzoic acid (1 g, 6.57 mmol) in methanol was added H$_2$SO$_4$ (0.8 mL) at 0° C. The reaction mixture was then heated to 75° C. and stirred for 8 h. After the completion of reaction, the mixture was concentrated under vacuum, diluted with water and extracted with ethyl acetate. The organic layer was dried over anhydrous sodium sulphate and concentrated to obtain methyl 2-hydroxybenzoate (1.8 g, yield: 81%) as a colourless liquid. $^1$H NMR (400 MHz, DMSO-d$_6$): δ 10.49 (s, 1H), 7.83 (d d, J=8.0 Hz, 1.6 Hz, 1H), 7.54-7.50 (m, 1H), 6.90-6.91 (m, 2H), 3.88 (s, 3H).

Step 2:2-Hydroxybenzohydrazide

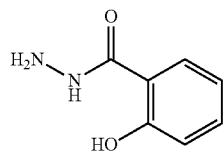 [SMILES: NNC(=O)c1ccccc1O]

To a stirred solution of methyl 2-hydroxybenzoate (1 g, 6.57 mmol) in ethanol was added hydrazine hydrate (1 mL) at room temperature. The reaction mixture was heated to reflux for 3 h. After the completion of the reaction, the mixture was concentrated under vacuum, diluted with water and extracted with ethyl acetate. The organic layer was dried over anhydrous sodium sulphate and concentrated to obtain 2-hydroxybenzohydrazide (480 mg, yield: 48%) as a white solid. $^1$H NMR (400 MHz, DMSO-d$_6$): δ 12.50 (brs, 1H), 10.05 (brs, 1H), 15.60 (d d, J=8.0 Hz, 1.2 Hz, 1H), 7.38-7.34 (m, 1H), 6.89-8.82 (m, 2H), 4.64 (brs, 2H). LC-MS (m/z): 153.1 (M+H)$^+$

Step 3:2-(Difluoromethoxy)-N-((5-(2-hydroxyphenyl)-1H-1,2,4-triazol-3-yl) methyl) benzamide (Compound 60)

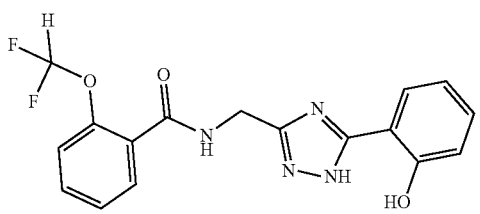 [SMILES: O=C(NCc1n[nH]c(-c2ccccc2O)n1)c1ccccc1OC(F)F]

To a stirred solution of N-(cyan methyl)-2-(difluoro methoxy) benzamide (200 mg, 0.88 mmol) and 2-hydroxybenzohydrazide (202 mg, 1.32 mmol) in n-BuOH was added K$_2$CO$_3$ (61 mg, 0.44 mmol) at room temperature. The resultant reaction mixture was irradiated at 165° C. for 50 min under microwave. After the completion of reaction, the mixture was concentrated under vacuum to get the crude product which was purified by flash column chromatography to obtain 2-(difluoromethoxy)-N-((5-(2-hydroxyphenyl)-1H-1,2,4-triazol-3-yl) methyl) benzamide (110 mg, yield: 35%) as an off-white solid. $^1$H NMR (400 MHz, DMSO-d$_6$): δ 14.18 (brs, 1H), 11.42 (brs, 1H), 8.85 (brs, 1H), 7.92 (brs, 1H), 7.64-7.53 (m, 2H), 7.33-6.96 (m, 6H), 4.61 (d, J=2.8 Hz, 2H). LC-MS (m/z): 361.1 (M+H)$^+$

Synthesis of 2-(difluoromethoxy)-N-((5-(2,3-dihydroxyphenyl)-1H-1,2,4-triazol-3-yl)methyl)benzamide (Compound 61)

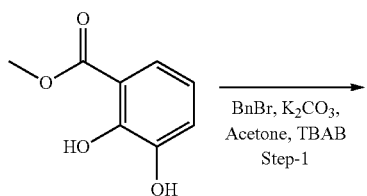

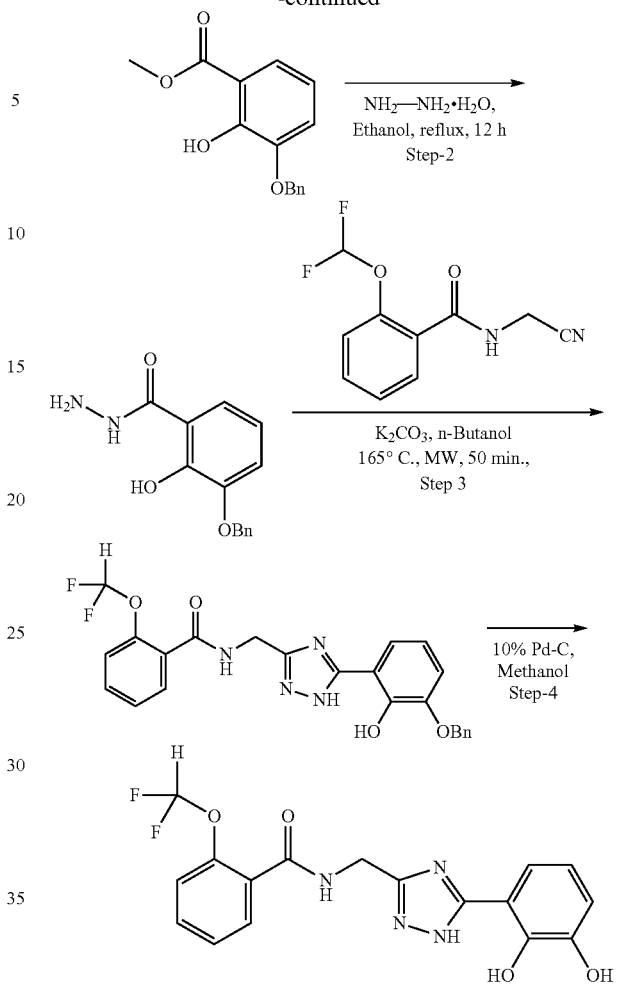

61

Step 1: Methyl 3-(benzyloxy)-2-hydroxybenzoate

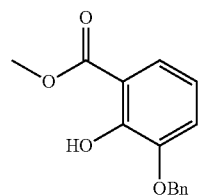 [SMILES: COC(=O)c1cccc(OCc2ccccc2)c1O]

To a stirred solution of methyl 2,3-dihydroxybenzoate (1 g, 5.95 mmol) in a mixture of chloroform and methanol, were added K$_2$CO$_3$ (3.3 g, 23.8 mmol) and benzyl bromide (0.85 mL, 7.14 mmol). The reaction mixture was stirred for 8 h at 60° C. After the completion of reaction, the mixture was concentrated under vacuum, the reaction mixture was diluted with water and extracted with ethyl acetate. The organic layer was dried over anhydrous sodium sulphate and concentrated to obtain the crude product which was purified by flash column chromatography to obtain methyl 5-(benzyloxy)-2-hydroxybenzoate (600 mg, yield: 38%) as a colorless liquid. $^1$H NMR (400 MHz, DMSO-d$_6$): δ 10.09 (s, 1H), 7.43 (d, J=7.2 Hz, 2H), 7.38 (t, J=7.2 Hz, 2H), 7.33-7.29 (m, 2H), 7.24-7.21 (m, 1H), 6.93 (d, J=8.8 Hz, 1H), 5.05 (s, 2H), 3.88 (s, 3H). LC-MS (m/z): 259.07 (M+H)+

Step 2: 3-(Benzyloxy)-2-hydroxybenzohydrazide

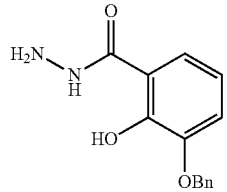 [SMILES: NNC(=O)c1cccc(OCc2ccccc2)c1O]

To a stirred solution of methyl 5-(benzyloxy)-2-hydroxybenzoate (600 mg, 2.32 mmol) in ethanol was added hydrazine hydrate (1 mL) at room temperature. The reaction mixture was then refluxed for 3 h. After the completion of reaction, the mixture was concentrated under vacuum and the reaction mixture was diluted with water and extracted with ethyl acetate. The organic layer was dried over anhydrous sodium sulphate and concentrated to obtain 3-(benzyloxy)-2-hydroxybenzohydrazide (430 mg, yield: 43%) as an off-white solid. $^1$H NMR (400 MHz, DMSO-$d_6$): δ 9.21 (s, 1H), 7.43 (d, J=7.2 Hz, 2H), 7.37 (t, J=6.8 Hz, 2H), 7.32-7.30 (m, 2H), 7.09 (dd, J=9.2 Hz, 3.2 Hz, 1H), 7.08 (d, J=8.8 Hz, 1H), 5.07 (s, 2H), 4.51 (brs, 2H), 3.79 (s, 1H). LC-MS (m/z): 273.17 (M+H)+

Step 3: N-((5-(3-(Benzyloxy)-2-hydroxyphenyl)-1H-1,2,4-triazol-3-yl) methyl)-2-(difluoromethoxy) benzamide

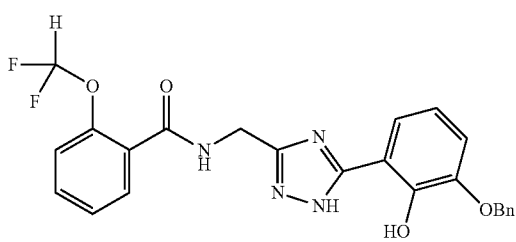 [SMILES: O=C(NCc1n[nH]c(-c2cccc(OCc3ccccc3)c2O)n1)c1ccccc1OC(F)F]

To a stirred solution of N-(cyan methyl)-2-(difluoro methoxy) benzamide (200 mg, 0.88 mmol) and 3-(benzyloxy)-2-hydroxybenzohydrazide (300 mg, 1.16 mmol) in n-BuOH was added K$_2$CO$_3$ (61 mg, 0.44 mmol) at room temperature. The reaction mixture was irradiated at 165° C. for 50 min under microwave. After the completion of the reaction, the mixture was concentrated under vacuum to obtain the crude product. It was then purified by flash column chromatography to obtain N-((5-(3-(benzyloxy)-2-hydroxyphenyl)-1H-1,2,4-triazol-3-yl) methyl)-2-(difluoro methoxy) benzamide (120 mg, yield: 29%) as an off white solid. $^1$H NMR (400 MHz, DMSO-$d_6$): δ 14.37 (s, 1H), 11.53 (brs, 1H), 11.25 (brs, 1H), 8.90 (brs, 1H), 7.53-7.52 (m, 2H), 7.47 (d, J=7.6 Hz, 2H), 7.40-7.30 (m, 5H), 7.25 (d, J=7.6 Hz, 1H), 7.14 (s, 1H), 6.83 (brs, 1H), 5.15 (S, 2H), 4.65 (brs, 2H). LC-MS (m/z): 467.2 (M+H)+

Step 4: 2-(Difluoromethoxy)-N-((5-(2,3-dihydroxyphenyl)-1H-1,2,4-triazol-3-yl) methyl) benzamide (Compound 61)

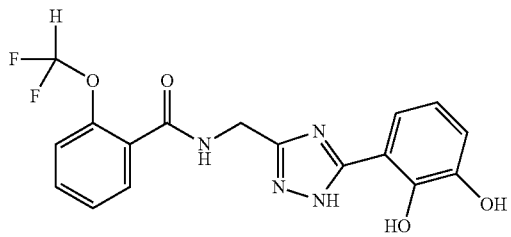 [SMILES: O=C(NCc1n[nH]c(-c2cccc(O)c2O)n1)c1ccccc1OC(F)F]

To a stirred solution of N-((5-(3-(benzyloxy)-2-hydroxyphenyl)-1H-1,2,4-triazol-3-yl) methyl)-2-(difluoro methoxy) benzamide (120 mg, 0.25 mmol) in ethanol was added Pd/C (100 mg) at room temperature. The reaction mixture was stirred for 12 h at room temperature under hydrogen atmosphere at 50 Psi. After the completion of reaction, the reaction mixture was filtered through celite bed and concentrated under reduced pressure to get the crude product, which was purified by preparative HPLC to obtain 2-(difluoromethoxy)-N-((5-(2,3-dihydroxyphenyl)-1H-1,2, 4-triazol-3-yl) methyl) benzamide (30 mg, yield: 18%) as a white solid. $^1$H NMR (400 MHz, DMSO-$d_6$): δ 11.27 (brs, 1H), 9.20 (brs, 1H), 9.17 (s, 1H), 7.60 (d, J=7.2 Hz, 1H), 7.55 (t, J=8.0 Hz, 1H), 7.37-7.32 (m, 2H), 7.26 (d, J=8.4 Hz, 1H), 7.15 (s, 1H), 6.75 (t, J=8 Hz, 1H), 4.60 (brs 2H), 3.15 (s, 1H). LC-MS (m/z): 377.10 (M+H)+

Synthesis of 2-(difluoromethoxy)-N-((5-(5-hydroxy-2-methoxyphenyl)-1H-1,2,4-triazol-3-yl)methyl) benzamide (Compound 63)

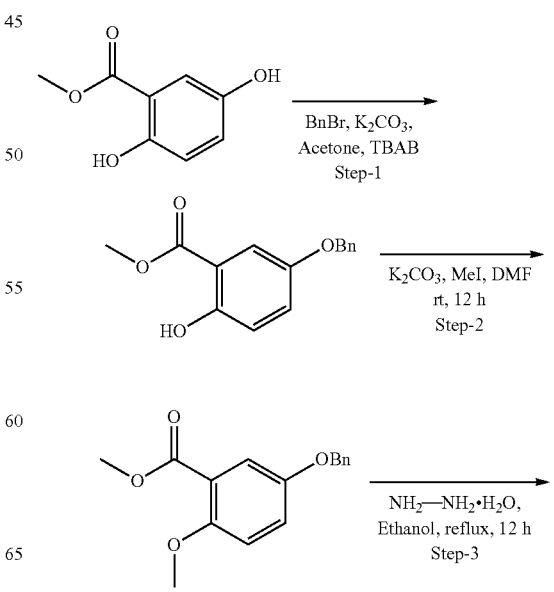

111

-continued

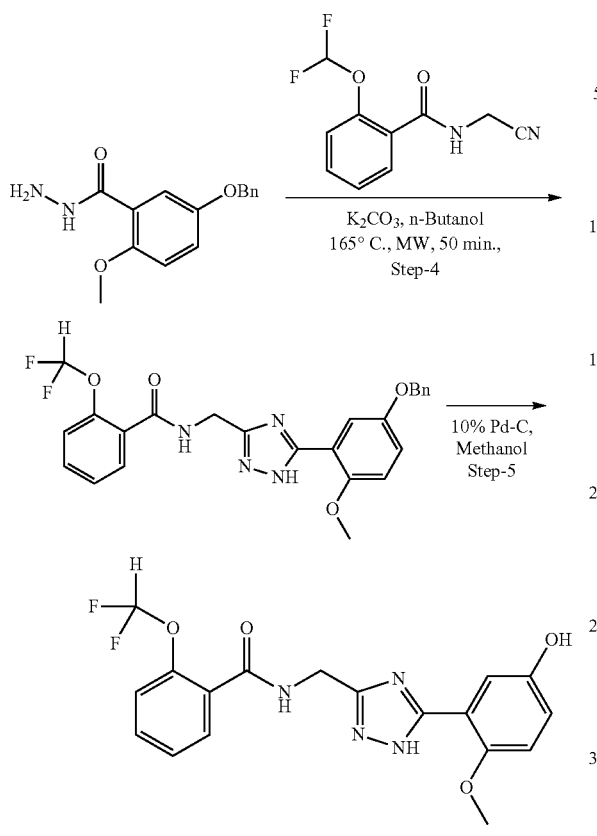

Step 1: Methyl 5-(benzyloxy)-2-hydroxybenzoate

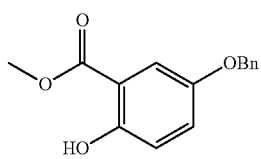 [SMILES: COC(=O)c1cc(OCc2ccccc2)ccc1O]

To a stirred solution of methyl 2,5-dihydroxybenzoate (1 g, 5.95 mmol) in chloroform and methanol, were added K$_2$CO$_3$ (3.3 g, 23.8 mmol) and benzyl bromide (0.85 mL, 7.14 mmol). The reaction mixture was then stirred for 8 h at 60° C. Upon completion of reaction, the mixture was concentrated under vacuum, diluted with water and extracted with ethyl acetate. The organic layer was dried over anhydrous sodium sulphate and concentrated. The crude product thus obtained was purified by flash column chromatography to obtain methyl 5-(benzyloxy)-2-hydroxybenzoate (470 mg, yield: 30%) as a colourless liquid. $^1$H NMR (400 MHz, DMSO-d$_6$): δ 10.09 (s, 1H), 7.43 (d, J=7.2 Hz, 2H), 7.38 (t, J=7.2 Hz, 2H), 7.33-7.29 (m, 2H), 7.24-7.21 (m, 1H), 6.93 (d, J=8.8 Hz, 1H), 5.05 (s, 2H), 3.88 (s, 3H). LC-MS (m/z): 259.07 (M+H)$^+$

112

Step 2: Methyl 5-(benzyloxy)-2-methoxybenzoate

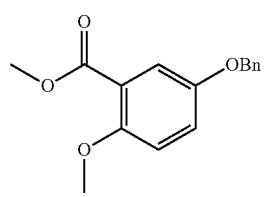 [SMILES: COC(=O)c1cc(OCc2ccccc2)ccc1OC]

To a stirred solution of methyl 5-(benzyloxy)-2-hydroxybenzoate (1.2 g, 4.65 mmol) in DMF, were added K$_2$CO$_3$ (1.29 g, 9.3 mmol) and methyl iodide (0.44 mL, 6.9 mmol). The resultant reaction mixture was stirred for 12 h at room temperature. Upon completion of the reaction, the mixture was diluted with water and extracted with ethyl acetate. The organic layer was dried over anhydrous sodium sulphate and concentrated to obtain methyl 5-(benzyloxy)-2-methoxybenzoate (1.0 g) as a colourless liquid. $^1$H NMR (400 MHz, DMSO-d$_6$): δ 7.42 (d, J=6.8 Hz, 2H), 7.38 (t, J=7.2 Hz, 2H), 7.32 (t, J=4.8 Hz, 1H), 7.25 (d, J=3.2 Hz, 1H), 7.15 (d d, J=8.8 Hz, 3.2 Hz, 1H), 7.07 (d, J=8.0 Hz, 1H), 5.07 (s, 2H), 3.76 (s, 3H), 3.74 (s, 3H). LC-MS (m/z): 273.10 (M+H)$^+$ Step 3: 5-(Benzyloxy)-2-methoxybenzohydrazide

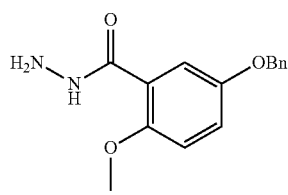 [SMILES: COc1ccc(OCc2ccccc2)cc1C(=O)NN]

To a stirred solution of methyl 5-(benzyloxy)-2-methoxybenzoate (1 g, 3.6 mmol) in ethanol was added hydrazine hydrate (1 mL) at room temperature. The resultant reaction mixture refluxed for 3 h. After the completion of the reaction, the mixture was concentrated under vacuum, diluted with water and extracted with ethyl acetate. The organic layer was dried over anhydrous sodium sulphate and concentrated to obtain 5-(benzyloxy)-2-methoxybenzohydrazide (430 mg, yield: 43%) as an off-white solid. $^1$H NMR (400 MHz, DMSO-d$_6$): δ 9.21 (s, 1H), 7.43 (d, J=7.2 Hz, 2H), 7.37 (t, J=6.8 Hz, 2H), 7.32-7.30 (m, 2H), 7.09 (dd, J=9.2 Hz, 3.2 Hz, 1H), 7.08 (d, J=8.8 Hz, 1H), 5.07 (s, 2H), 4.51 (brs, 2H), 3.79 (s, 1H). LC-MS (m/z): 273.17 (M+H)$^+$ Step 4: N-((5-(5-(Benzyloxy)-2-methoxyphenyl)-1H-1,2,4-triazol-3-yl)methyl)-2-(difluoromethoxy)benzamide

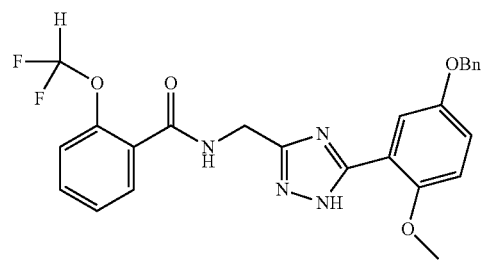 [SMILES: COc1ccc(OCc2ccccc2)cc1-c1nc(CNC(=O)c2ccccc2OC(F)F)n[nH]1]

To a stirred solution of N-(cyan methyl)-2-(difluoro methoxy) benzamide (200 mg, 0.88 mmol) and 5-(benzyloxy)-2-methoxybenzohydrazide (360 mg, 1.32 mmol) in n-BuOH was added K₂CO₃ (61 mg, 0.44 mmol) at room temperature. The reaction mixture was irradiated at 165° C. for 50 min under microwave. The resultant reaction mixture was then concentrated under vacuum to get the crude product (200 mg) which was used in the next step without further purification.

Step 5: 2-(Difluoromethoxy)-N-((5-(5-hydroxy-2-methoxyphenyl)-1H-1,2,4-triazol-3-yl) methyl) benzamide (Compound 63)

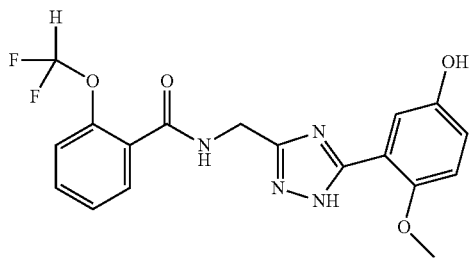 [SMILES: COc1ccc(O)cc1-c1nc(CNC(=O)c2ccccc2OC(F)F)n[nH]1]

To a stirred solution of N-((5-(5-(benzyloxy)-2-methoxyphenyl)-1H-1,2,4-triazol-3-yl)methyl)-2-(difluoromethoxy) benzamide (200 mg, 0.42 mmol) in ethanol was added Pd/C (160 mg) at room temperature. The reaction mixture was stirred for 12 h at room temperature under hydrogen atmosphere (50 Psi). The resultant reaction mixture was filtered through celite bed and concentrated under reduced pressure to get the crude product. It was further purified by preparative HPLC to obtain 2-(difluoromethoxy)-N-((5-(5-hydroxy-2-methoxyphenyl)-1H-1,2,4-triazol-3-yl)methyl) benzamide (30 mg, yield: 18%) as a white solid. ¹H NMR (400 MHz, DMSO-d₆): δ 13.45 (s, 1H), 9.20 (s, 1H), 8.75 (brs, 1H), 7.60 (d, J=7.6 Hz, 1H), 7.54-7.50 (m, 2H), 7.35-7.33 (m, 1H), 7.24 (d, J=8.4 Hz, 1H), 7.16 (s, 1H), 7.01-6.98 (m, 1H), 6.82 (d, J=3.2 Hz, 1H), 4.52 (d, J=5.6 Hz, 2H), 3.85 (s, 3H). LC-MS (m/z): 391.10 (M+H)⁺

Synthesis of 2-(difluoromethoxy)-N-((5-(3-hydroxy-2-methoxyphenyl)-1H-1,2,4-triazol-3-yl) methyl) benzamide (Compound 62)

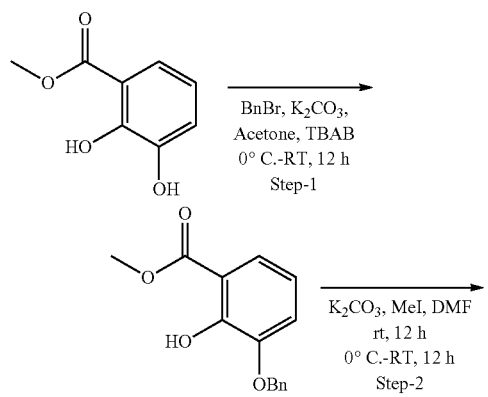

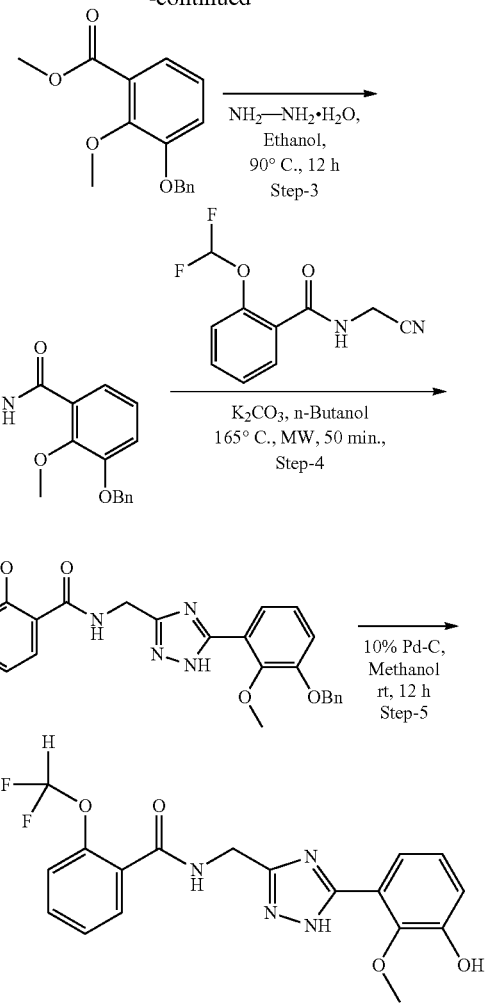

Step-1: Synthesis of methyl 3-(benzyloxy)-2-hydroxybenzoate

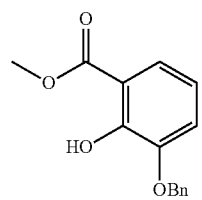 [SMILES: COC(=O)c1cccc(OCc2ccccc2)c1O]

To the stirred solution of methyl 2,3-dihydroxybenzoate (1) (500 mg, 2.973 mmol) in acetone (10 mL) at 0° C., was added K₂CO₃ (410 mg, 2.973 mmol) followed by (bromomethyl)benzene (423.8 mg, 3.568 mmol) and tetrabutylammonium bromide (191.7 mg, 0.594 mmol). The reaction mixture stirred at room temperature for 12 h. The resultant reaction mixture was concentrated under reduced pressure and the crude product thus obtained was diluted with cold water and extract with ethyl acetate (2×20 mL). The combined organic layer was washed with brine (20 mL), dried over anhydrous Na₂SO₄ and concentrated under reduced pressure. The crude product thus obtained was purified by column chromatography using 2% EtOAc in n-hexane to get white solid as a methyl 3-(benzyloxy)-2-hydroxybenzoate (100 mg, 13%). ¹H NMR (400 MHz, DMSO-d₆): δ 10.60 (s, 1H), 7.45 (d, J=7.2 Hz, 2H), 7.40-7.29 (m, 4H), 7.27 (d, J=8 Hz, 1H), 6.84 (t, J=8 Hz, 1H), 5.14 (s, 2H), 3.89 (s, 3H). LC-MS (m/z): 259.30 (M+H)⁺

Step-2: Synthesis of methyl 3-(benzyloxy)-2-methoxybenzoate

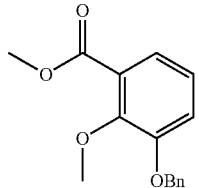 [SMILES: COC(=O)c1cccc(OCc2ccccc2)c1OC]

To a stirred solution of methyl 3-(benzyloxy)-2-hydroxybenzoate (500 mg, 1.937 mmol) in DMF (20 mL) at 0° C., was added K₂CO₃ (410 mg, 2.973 mmol) followed by Iodomethane (412.4 mg, 2.905 mmol). The reaction mixture was stirred at room temperature for 12 h. After the completion of the reaction, the mixture was quenched with ice-cold water and extracted with ethyl acetate (3×20 mL). The combined organic layer was washed with brine (20 mL), dried over anhydrous Na₂SO₄ and concentrated under reduced pressure. The obtained solid was triturated with diethyl ether and dried under vacuum to get methyl 3-(benzyloxy)-2-methoxybenzoate (450 mg, 85.3%) as off-white solid. ¹H NMR (400 MHz, DMSO-d₆): δ 17.45 (d, J=7.2 Hz, 2H), 7.39 (t, J=7.2 Hz, 2H), 7.35-7.31 (m, 2H), 7.09 (dd, J=8.4 Hz, 1.6 Hz, 1H), 7.04 (t, J=7.6 Hz, 1H), 5.14 (s, 2H), 3.95 (s, 3H), 3.91 (s, 3H).

Step-3: Synthesis of 3-(benzyloxy)-2-methoxybenzohydrazide

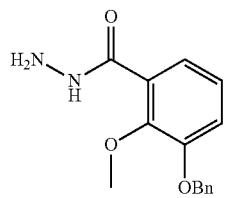 [SMILES: COc1c(OCc2ccccc2)cccc1C(=O)NN]

To the stirred solution of methyl 3-(benzyloxy)-2-methoxybenzoate (450 mg, 1.65 mmol) in EtOH (20 mL) at 0° C., was added hydrazine hydrate (0.5 mL). The resultant reaction mixture was stirred at 90° C. for 12 h and concentrated. The obtained residue was diluted with ice-cold water and extract with ethyl acetate (3×20 mL). The combined organic layer was washed with brine (20 mL), dried over anhydrous Na₂SO₄ and concentrated under reduced pressure. The obtained solid was triturated with diethyl ether and dried under vacuum to get 3-(benzyloxy)-2-methoxybenzohydrazide (250 mg, 55.5%) as off-white solid. ¹H NMR (400 MHz, DMSO-d₆): δ 9.27 (s, 1H), 7.47 (d, J=7.6 Hz, 2H), 7.40 (t, J=7.2 Hz, 2H), 7.33 (t, J=7.2 Hz, 1H), 7.21 (dd, J=8.0 Hz, 1.6 Hz, 1H), 7.09-7.01 (m, 2H), 5.15 (s, 2H), 4.47 (brs, 2H), 2.93 (s, 3H).

Step-4: Synthesis of N-((5-(3-(benzyloxy)-2-methoxyphenyl)-1H-1,2,4-triazol-3-yl)methyl)-2-(difluoromethoxy)benzamide

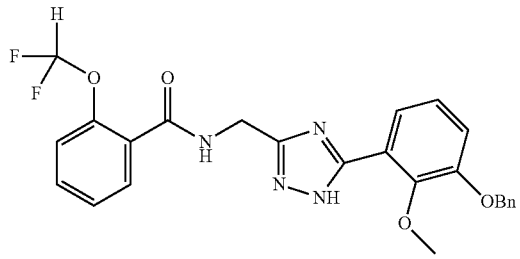 [SMILES: COc1c(OCc2ccccc2)cccc1-c1nc(CNC(=O)c2ccccc2OC(F)F)n[nH]1]

To the stirred solution of N-(cyanomethyl)-2-(difluoro methoxy) benzamide (250 mg, 1.105 mmol) in n-BuOH (10 mL) at 0° C., was added K₂CO₃ (76.2 mg, 0.552 mmol) followed by 3-(benzyloxy)-2-methoxybenzohydrazide (331 mg, 1.215 mmol). The resultant reaction mixture stirred at 165° C. for 50 min under microwave irradiation. Upon completion of reaction, the mixture was diluted with water and extracted with ethyl acetate (3×20 mL). The combined organic layer was washed with brine (20 mL), dried over anhydrous Na₂SO₄ and concentrated under reduced pressure. The crude product thus obtained was purified by column chromatography using 60% EtOAc in n-hexane to obtain N-((5-(3-(benzyloxy)-2-methoxyphenyl)-1H-1,2,4-triazol-3-yl) methyl)-2-(difluoro methoxy) benzamide (170 mg, 32%) as brown solid. ¹H NMR (400 MHz, DMSO-d₆): δ 13.63 (s, 1H), 8.54 (t, J=5.6 Hz, 1H), 7.60 (t, J=8.4 Hz, 2H), 7.54-7.49 (m, 3H), 7.42 (t, J=7.2 Hz, 2H), 7.36-7.30 (m, 2H), 7.26 (t, J=8.8 Hz, 2H), 7.17 (t, J=7.6 Hz, 2H), 5.19 (s, 2H), 4.53 (d, J=5.6 Hz, 2H), 3.84 (s, 3H). LC-MS (m/z): 481.20 (M+H)⁺

Step-5: Synthesis of 2-(difluoromethoxy)-N-((5-(3-hydroxy-2-methoxyphenyl)-1H-1,2,4-triazol-3-yl) methyl) benzamide (Compound 62)

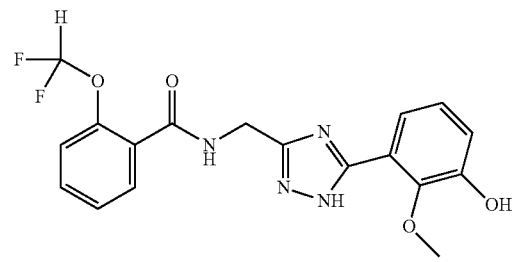 [SMILES: COc1c(O)cccc1-c1nc(CNC(=O)c2ccccc2OC(F)F)n[nH]1]

To a stirred solution of N-((5-(3-(benzyloxy)-2-methoxyphenyl)-1H-1,2,4-triazol-3-yl) methyl)-2-(difluoro methoxy) benzamide (170 mg, 0.354 mmol) in methanol (20 mL), was added Pd/C (170 mg). The reaction mixture was stirred under hydrogen balloon for 12 h at room temperature. Upon completion of reaction, the mixture was filtered through a short celite bed, washed with methanol, dried over anhydrous Na₂SO₄, and concentrated. The crude product thus obtained was purified by column chromatography using 50% EtOAc in n-hexane to obtain 2-(difluoromethoxy)-N-((5-(3-hydroxy-2-methoxyphenyl)-1H-1,2,4-triazol-3-yl) methyl) benzamide (45 mg, 32.6%) as brown solid. ¹H NMR (400 MHz, DMSO-d₆): 9.71 (brs, 1H), 8.79 (t, J=5.2 Hz, 1H), 7.62 (dd, J=8.0 Hz, 1.6 Hz, 1H), 7.55-7.50 (m, 1H), 7.39-7.31 (m, 2H), 7.24 (d, J=8.4 Hz, 1H), 7.17 (s, 1H), 7.03-6.95 (m, 2H), 4.54 (d, J=7.6 Hz, 2H), 3.78 (s, 3H). LC-MS (m/z): 391.1 (M+H)⁺

Synthesis of N-((5-(2-methoxyphenyl)-1H-1,2,4-triazol-3-yl) sulfonyl)-2-(trifluoro methoxy) benzamide (Compound 123) AND 2-(difluoromethoxy)-N-((5-(2-methoxyphenyl)-1H-1,2,4-triazol-3-yl) sulfonyl) benzamide (Compound 124)

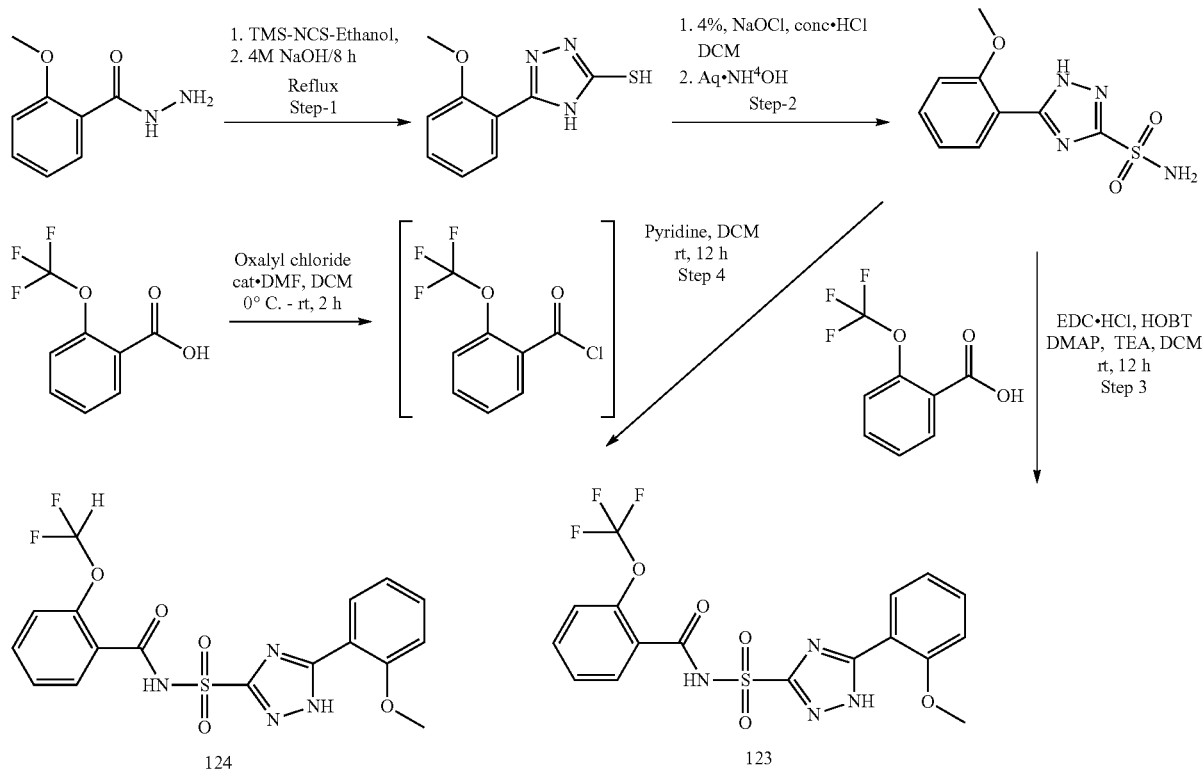

Step-1: 5-(2-methoxyphenyl)-4H-1,2,4-triazole-3-thiol

To a stirred solution of 2-methoxy benzhydrazide (2.5 g, 15.04 mmol) in ethanol (25 mL) at 0° C., was added trimethylsilyl isothiocyanate (1.97 g, 15.04 mmol) and the reaction was heated at 90° C. for 4 h. To the resultant reaction mixture was then added 4M NaOH solution (25 mL) and was further at 90° C. for another 4 h. The reaction mixture was then concentrated, diluted with H$_2$O (10 mL) and acidified with HCl (40 mL, 4M). The resultant precipitate was filtered and dried under vacuum to afford 5-(2-methoxyphenyl)-4H-1,2,4-triazole-3-thiol as off-white solid (2.1 g mg, 67.37%). $^1$H NMR (400 MHz, DMSO) δ 13.61 (s, 1H), 13.11 (s, 1H), 7.63 (d, J=6.4 Hz, 1H), 7.49 (t, J=7.2 Hz, 1H), 7.15 (d, J=8.4 Hz, 1H), 7.04 (t, J=7.2 Hz, 1H), 3.83 (s, 3H). LC-MS (ESI): m/z 208.1 (M+H)

Step-2: 5-(2-methoxyphenyl)-1H-1,2,4-triazole-3-sulfonamide

To a stirred solution of 5-(2-methoxyphenyl)-4H-1,2,4-triazole-3-thiol (500 mg, 15.04 mmol) in dichloromethane (10 mL) at 0° C., was added 4M HCl (10 mL) and 4% NaOCl (10 mL) dropwise while maintaining the temperature below 5° C., followed by further stirring at the same temperature for 15 min. From the resultant mixture the organic layer was separated and to it was added aqueous NH$_4$OH solution and stirred for 12 h. After the completion of reaction, the organic layer was collected and concentrated under reduced pressure and co-evaporated with toluene to remove water to afford 5-(2-methoxyphenyl)-1H-1,2,4-triazole-3-sulfonamide as off-white solid (2.1 g, 67.37%). LC-MS (ESI): m/z 255.1 (M+H)

Step-3: N-((5-(2-methoxyphenyl)-1H-1,2,4-triazol-3-yl) sulfonyl)-2-(trifluoro methoxy) benzamide (Compound 123)

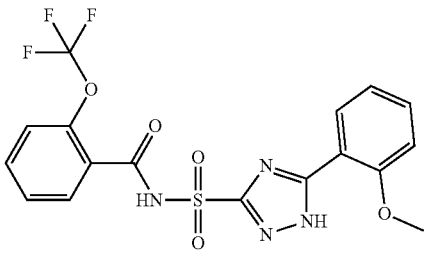 [SMILES: COc1ccccc1-c1nc(S(=O)(=O)NC(=O)c2ccccc2OC(F)(F)F)n[nH]1]

To a stirred solution of 5-(2-methoxyphenyl)-1H-1, 2, 4-triazole-3-sulfonamide (100 mg, 0.393 mmol) and 2-(trifluoromethoxy) benzoic acid (81.06 mg, 0.393) in dichloromethane (20 mL) at 0° C., were added EDC.HCl (113.09 mg, 0.589 mmol), HOBt (79.58 mg, 0.588 mmol), DMAP (5 mg) and triethylamine (98.98 mg, 0.98 mmol). The resulting reaction mixture was stirred at room temperature for 12 h and concentrated. The resultant residue was diluted with H$_2$O (10 mL) and extracted with 10% methanol in dichloromethane (3×15 mL). The combined organic layer was dried over Na$_2$SO$_4$ and concentrated to get the crude compound. The crude compound was purified by preparative HPLC to afford N-((5-(2-methoxyphenyl)-1H-1,2,4-triazol-3-yl) sulfonyl)-2-(trifluoro methoxy) benzamide as off-white solid (14 mg, 8%). $^1$H NMR (400 MHz, DMSO) δ 13.75 (s, 1H), 8.08 (d, J=6.8 Hz, 1H), 7.33 (d, J=8.0 Hz, 1H), 7.46 (t, J=7.2 Hz, 1H), 7.40 (t, J=8.4 Hz, 1H), 7.32 (t, J=7.6 Hz, 1H), 7.20 (t, J=9.6 Hz, 2H), 7.09 (t, J=8.0 Hz, 1H), 3.95 (s, 3H). LC-MS (ESI): m/z 443.1 (M+H)

Step-4: 2-(difluoro methoxy)-N-((5-(2-methoxyphenyl)-1H-1, 2, 4-triazol-3-yl) sulfonyl) benzamide (Compound 124)

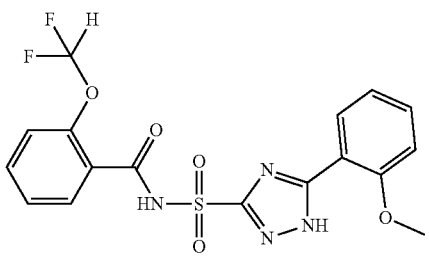 [SMILES: COc1ccccc1-c1nc(S(=O)(=O)NC(=O)c2ccccc2OC(F)F)n[nH]1]

To a stirred solution of 5-(2-methoxyphenyl)-1H-1, 2, 4-triazole-3-sulfonamide (261.20 mg, 1.065 mmol) in dichloromethane (20 mL) at 0° C., were added pyridine (168.48 mg, 2.130 mmol) followed by freshly prepared 2-(difluoromethoxy)benzoyl chloride (220 mg, 1.065 mmol). The resulting reaction mixture was stirred at room temperature for 12 h. After the completion of the reaction, the mixture was diluted with H$_2$O (20 mL) and extracted with 10% methanol in dichloromethane (3×15 mL). The combined organic layer was dried over Na$_2$SO$_4$ and concentrated to obtain the crude compound. It was purified by preparative HPLC to afford 2-(difluoro methoxy)-N-((5-(2-methoxyphenyl)-1H-1, 2, 4-triazol-3-yl) sulfonyl) benzamide as off-white solid (22 mg, 4.86%). $^1$H NMR (400 MHz, DMSO) δ 7.99 (d, J=8.0 Hz, 1H), 7.67 (m, 1H), 7.46 (t, J=8.4 Hz, 1H), 7.35 (t, J=7.2 Hz, 1H), 6.88-7.21 (m, 6H), 3.94 (s, 3H). LC-MS (ESI): m/z 425.1 (M+H)

Synthesis of 2-(difluoro methoxy)-N-((5-(2-methoxyphenyl)-1H-pyrazol-3-yl)sulfonyl)benzamide (Compound 121)

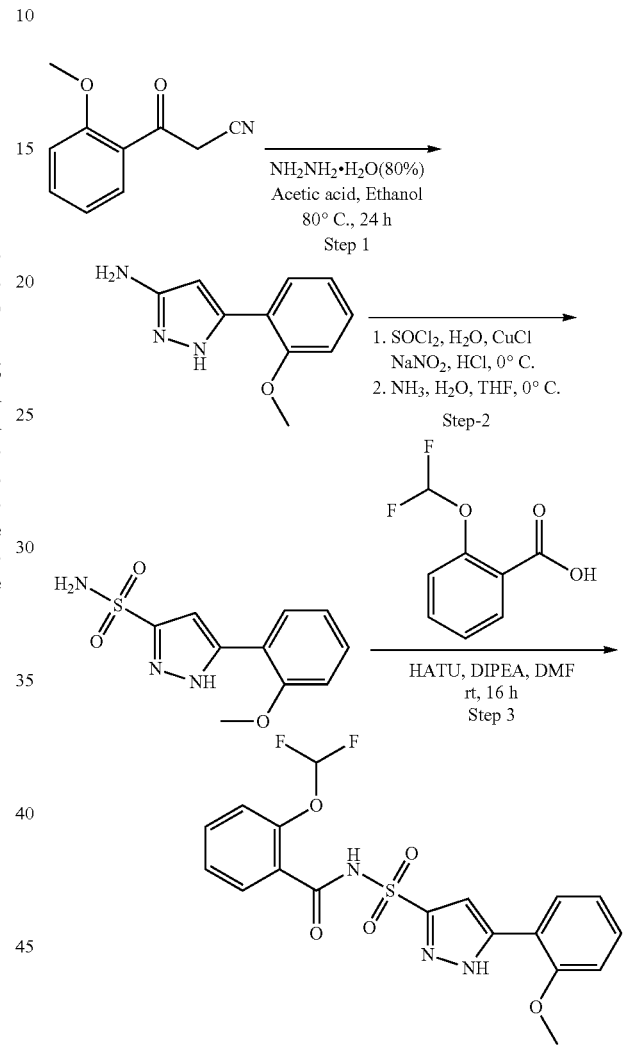

121

Step 1: 5-(2-methoxyphenyl)-1H-pyrazol-3-amine

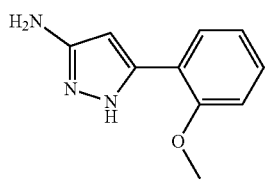

To a stirred solution of methyl 3-(2-methoxyphenyl)-3-oxopropanenitrile (2.5 g, 14.27 mmol) in ethanol (10 mL) and was added hydrazine hydrate (10 mL) followed by catalytic amount of acetic acid. The resultant mixture was stirred at 80° C. for 24 h and concentrated. The residue was washed twice with toluene (10 mL) and dried under vacuum to afford 5-(2-methoxyphenyl)-1H-pyrazole-3-amine as a yellow viscous liquid (2 g, 74%). $^1$H NMR (400 MHz, DMSO) δ 11.56 (bs, 1H), 7.62 (d, J=7.6 Hz, 1H), 7.26 (dd, J=1.6, 8.8 Hz, 1H), 7.07 (d, J=8.4 Hz, 1H), 6.95 (t, J=7.2 Hz, 1H), 4.58 (bs, 2H), 3.84 (s, 3H). LC-MS m/z (M+H): 190.1.

Step 2:
5-(2-methoxyphenyl)-1H-pyrazole-3-sulfonamide

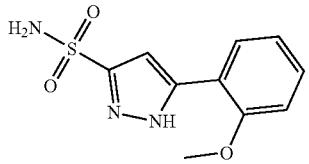 [SMILES: COc1ccccc1-c1cc(S(N)(=O)=O)n[nH]1]

To a suspension of CuCl (0.204 g, 2.1 mmol) in water (265 mL) was added thionyl chloride (44.85 mL, 0.618 mmol) dropwise at 0° C. with vigorous stirring. The resultant solution was stirred at room temperature overnight to give a light yellow solution. Separately, to a solution of 5-(2-methoxyphenyl)-1H-pyrazol-3-amine (0.62 g, 4.1 mmol) in concentrated HCl (4 mL) was added dropwise a solution of NaNO$_2$ (0.33 g, 4.8 mmol) in water (4 mL) at −10° C. The resulting dark orange solution was stirred at −10° C. for 30 minutes and then added to the solution (10.6 mL) of copper (I) chloride from first step at −5° C. over 5 minutes. The resultant reaction mixture was stirred at −5° C. for 1 hour and extracted with ethyl acetate (10 mL×3). The combined organic layer was concentrated in vacuum to give yellow solid. This solid was dissolved in THF (20 mL) and cooled to 0° C., followed by the dropwise addition of ammonia (10 mL, 28% wt). The resultant reaction mixture was stirred for 2 hours at 0° C. and then concentrated under vacuum. The crude product thus obtained was purified by flash chromatography by using dichloromethane and methanol as eluting solvent to afford 5-(2-methoxyphenyl)-1H-pyrazole-3-sulfonamide as off-white solid (85 mg, 10%). $^1$H NMR (400 MHz, DMSO) δ 13.53 (s, 1H), 7.71 (dd, J=1.2, 7.6 Hz, 1H), 7.40-7.37 (m, 3H), 7.18-7.16 (d, J=8.4 Hz, 1H), 7.05 (t, J=7.6 Hz, 1H), 6.97 (d, J=2.0 Hz, 1H), 3.89 (s, 3H). LC-MS m/z (M+H): 254.09.

Step 3: 2-(difluoro methoxy)-N-((5-(2-methoxyphenyl)-1H-pyrazol-3-yl) sulfonyl) benzamide (Compound 121)

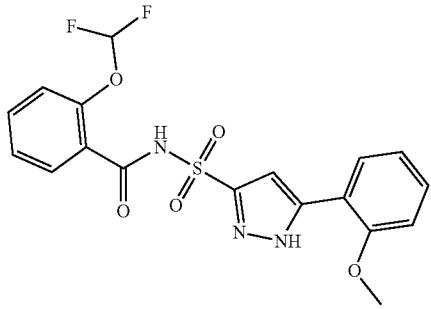 [SMILES: COc1ccccc1-c1cc(S(=O)(=O)NC(=O)c2ccccc2OC(F)F)n[nH]1]

To a stirred solution of 2-(difluoro methoxy) benzoic acid (44 mg, 0.2371 mmol) in DMF (1 mL) at 0° C., was added HATU (72.13 mg, 0.1897 mmol), 5-(2-methoxyphenyl)-1H-pyrazole-3-sulfonamide (40 mg, 0.1581 mmol) and DIPEA and the resultant mixture was stirred at room temperature for 16 h. It was then quenched with ice cold water and extracted with ethyl acetate (2×50 mL). The combined organic layer washed with brine solution (50 mL), dried over sodium sulfate and concentrated to obtain the crude product. The crude product was further purified by preparative HPLC to afford 2-(difluoro methoxy)-N-((5-(2-methoxyphenyl)-1H-pyrazol-3-yl) sulfonyl) benzamide off-white solid (28 mg, 41.87%). $^1$H NMR (400 MHz, DMSO) δ 13.84 (s, 1H), 12.61 (s, 1H), 7.76 (d, J=7.2 Hz, 1H), 7.58 (t, J=6.8 Hz, 1H), 7.52 (d, J=7.2 Hz, 1H), 7.41 (t, J=7.2 Hz, 1H), 7.31 (t, J=6.8 Hz, 1H), 7.24-6.95 (m, 5H), 3.91 (s, 3H). LC-MS m/z (M−H): 423.39.

N-[[5-(2-methoxyphenyl)-1H-pyrazol-3-yl]sulfonyl]-2-(trifluoromethoxy)benzamide (Compound 122)

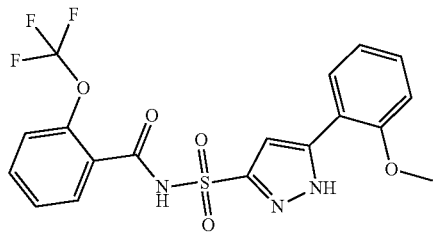 [SMILES: COc1ccccc1-c1cc(S(=O)(=O)NC(=O)c2ccccc2OC(F)(F)F)n[nH]1]

Compound 122 was synthesized using the protocol described for compound 121. Yield: 25%. LC-MS m/z (M−H): 442.1.

Biochemical and Cellular Assays

Biochemical Modulation of UBE2K Poly Ubiquitination Activity by Small Molecules Modulators.

In vitro poly-ubiquitination activity assays were performed using 3 µM UBE2K, 300 nM UBE1, and 200 µM Ub in 50 mM Tris pH 8.0, 1 mM TCEP buffer containing 0.05% tween 20, 4 mM ATP, and 10 mM MgCl2. Reactions were performed at various concentrations of compounds, incubated at 37 C for 3 hours, and quenched with non-reducing sample loading dye. Samples were analyzed using 4-20% Criterion™ TGX Stain-Free™ Protein Gel and 4-20% Criterion Stained Gel and imaged stain-free and post-Coomassie staining using BioRad Imager. Compound titrations were performed in 1×PBS-P+(GE) buffer containing 3% DMSO. Freshly opened DMSO was used to prepare the running buffer immediately before the experiment. Compound stocks (in DMSO provided by Berg) were first diluted into 1×PBS-P+ without DMSO to match to 3% DMSO. The final concentration of this 3% DMSO matched solution was determined by the concentration of the original stock (i.e. for 100 mM DMSO stock, 3% match stock is 3 mM). The match stock was then diluted to 100 uM using 1×PBS-P+(GE) buffer containing 3% DMSO, and serially diluted.

Compounds were observed to stabilize the Mono-Ubiquitinated UBE2K in the poly-ubiquitination assay in a stain free gel leading to a decrease in Poly-Ub product. The converse was also observed in stained gel where in lesser ubiquitin was used in the poly-ubiquitination-polymerization upon compound treatment. Both effects were dose dependent. FIG. 1 shows the analysis performed from 5 independent experiments (N=5). Stain Free gel utilizes an in-gel compound that enhances the fluorescence of tryptophan amino acids when exposed to UV light. Native Ubiquitin has no tryptophan residue, while UBE2K and UBE1 contains tryptophan. Hence it easier to detect the Mono-Ub UBE2K band on a Stain free gel.

UBE2K Selectivity Assay

Figure 2:
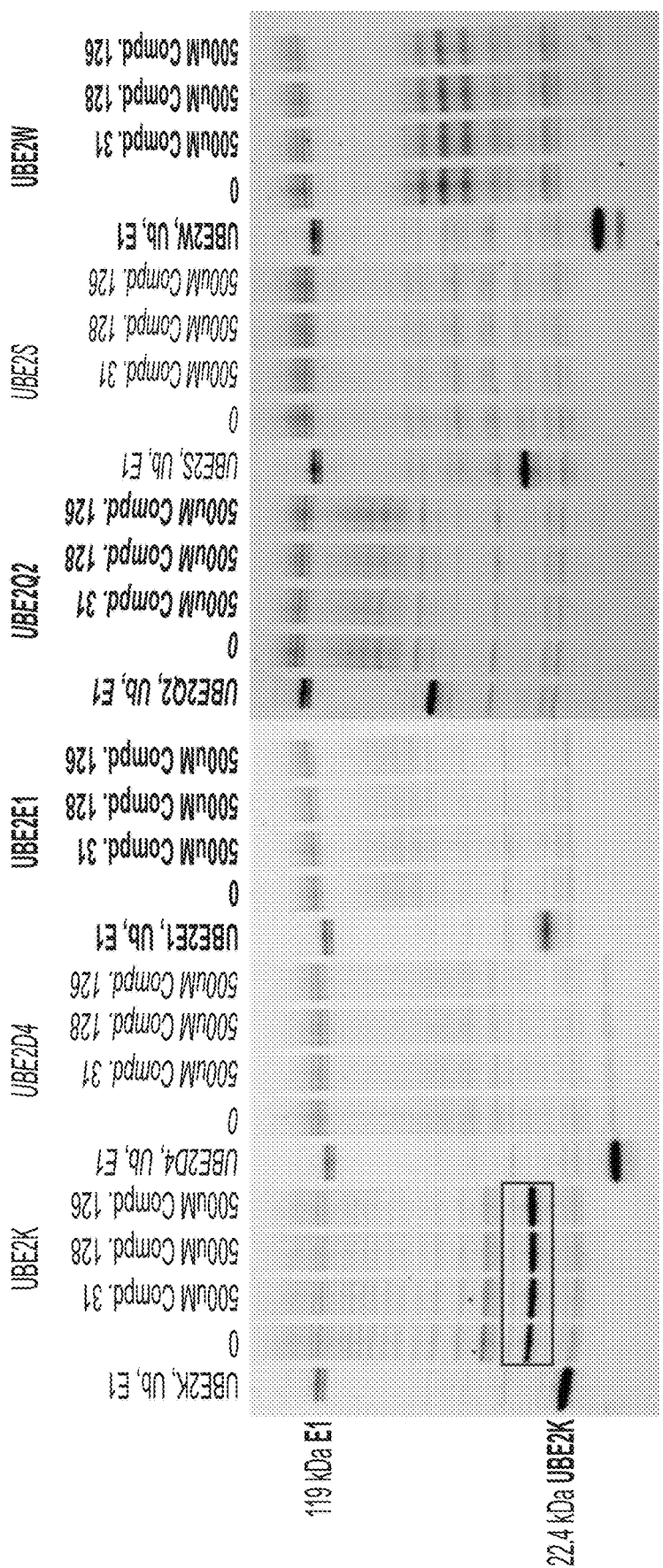
FIG. 2 illustrates selective stabilization of mono-ubiquitinated UBE2K by certain inventive compounds.

The selectivity of inventive compounds for UbE2K versus other E2s were tested in the in vitro poly-ubiquitination assay as described previously. E2-ubiquitin conjugating enzymes namely UBE2D4, UBE2E1, UBE2Q2, UBE2S and UBE2W from E2 family of enzymes were selected. The ability of inventive compounds at 500 µM to stabilize mono ubiquitinated E2s and poly Ub products were observed. While inventive compounds stabilized mono-Ub UBE2K and decreased poly Ub chains, the same was not observed for other class representatives of E2s in the assay. E2s have a highly conserved active site, the observation that the inventive compounds did not impact or modulate other E2s confirm an allosteric site that these molecules engage. Results are shown in FIG. 2.

Praja 1 Assay

The assay uses UBE2K thioester linked Ubiquitin and the ability of small molecule modulators to affect the discharge of Ubiquitin to Praja1 RING domain and the ability to poly ubiquitinate PRAJA1. Levels of Poly ubiquitination were measure using an ELISA format using an anti Ub A5 primary antibody (AF594) in combination with a secondary antibody (Goat polyclonal antimouse AP) conjugated to Alkaline phosphatase and Attophos AP fluorescent substrate system. The fluorescence was read using a Teacan Spark 10M plate reader at an Excitation wavelength of 435 and Emission wavelength of 555.

Figure 3:
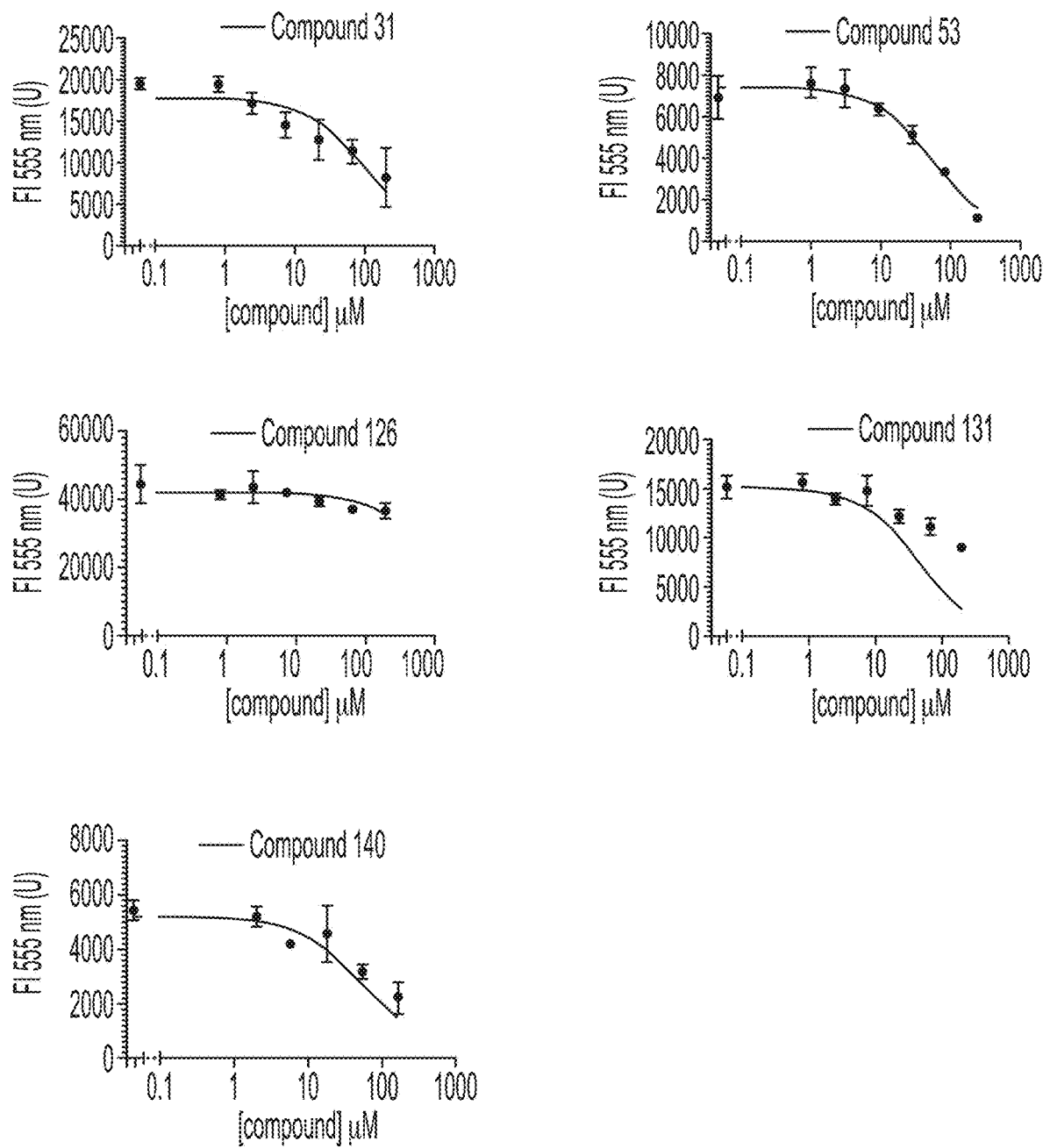
FIG. 3 illustrates the UBE2K-Ub Discharge Activity by certain inventive compounds.

Inventive compounds were observed to modulate the extent of Ubiquitin discharge from UBE2K and the polyubiquitination of Praja1 RING protein in a concentration dependent manner. A decrease in ELISA signal means a decrease in discharge of ubiquitin to create Poly Ub Praja1 RING. Inventive compounds were observed to decrease Poly Ub Praja1. See FIG. 3.

Cellular Viability Assay

Cell viability were performed using the Cell Titer Fluor™ Assays (Promega G6080). MIA PaCa-2 cells are grown in DMEM media with 10% FBS, 1% Pen/Strep/Amphotericin B. Cells are trypsinized and counted using the Nexcelom cellometer. 5,000 cells/100 µl are plated per well in Greiner black/clear 96-well plates. Cells should be within 10 passages of stock vial for use in workflow. Three distinct lineages of these cells are cultured in parallel for multiple passages and 5 full plates of each lineage are seeded for one run. Small molecule compounds are provided as 100 mM stock solutions in DMSO. Dilution series plates are prepared using 1:3 dilution to achieve a 7 point concentration on a half log scale. After addition of compounds, cells are incubated 37° C., 5% $CO_2$ for 72 hours.

For each test compound condition, triplicate technical replicates are used. For each reference compound, duplicate technical replicates are used. At the end of the 72-hour incubation, spent media is discarded. Then, 100 µl of GF-AFC diluted in DMEM (serum and phenol red-free) is added at 1:2000 concentration (5 µl/10 ml). Cells are incubated with reaction buffer for 1 h at 37° C. Fluorescence is then read on the plate reader with excitation wavelength of 390 nm and emission wavelength of 505 nm. All raw data are analyzed on Microsoft Excel 2010 and normalized to the DMSO vehicle control. Relative results are copied into GraphPad Prism for non-linear regression analysis and determination of IC50 and other dose curve parameters (min, max, Hill slope, etc.) using the log (inhibitor) vs. response equation. Results are shown in Table 11. Values are as follows: A represents an IC50 of <1.0 mM, B represents an IC50 of 1 mM to 10 mM, C represents an IC50 of >10 mM.

TABLE 11

| Comp No. | IC50 (mM) |
|---|---|
| 4 | C |
| 5 | C |
| 8 | C |
| 13 | C |
| 14 | C |
| 15 | C |
| 16 | C |
| 17 | C |
| 20 | C |
| 21 | C |
| 22 | C |
| 24 | C |
| 25 | C |
| 27 | C |
| 28 | C |
| 29 | C |
| 30 | C |
| 31 | A |
| 33 | B |
| 34 | B |
| 35 | B |
| 36 | A |
| 37 | C |
| 39 | C |
| 40 | C |
| 43 | C |
| 44 | B |
| 47 | C |
| 48 | B |
| 49 | B |
| 50 | C |
| 51 | A |
| 52 | C |
| 53 | A |
| 55 | A |
| 56 | A |
| 57 | A |
| 58 | A |
| 59 | C |
| 60 | A |
| 61 | B |
| 62 | B |
| 63 | B |
| 64 | B |
| 65 | A |
| 66 | A |
| 67 | A |
| 68 | A |
| 69 | A |
| 70 | C |
| 71 | B |
| 72 | A |
| 73 | C |
| 74 | C |
| 75 | A |
| 76 | B |
| 77 | A |
| 78 | A |
| 79 | B |
| 80 | A |
| 81 | B |
| 82 | B |
| 83 | B |
| 84 | B |
| 85 | A |
| 86 | C |

TABLE 11-continued

| Comp No. | IC50 (mM) |
|---|---|
| 87 | C |
| 88 | C |
| 89 | C |
| 90 | C |
| 91 | A |
| 92 | A |
| 93 | A |
| 94 | A |
| 95 | A |
| 96 | A |
| 97 | B |
| 98 | A |
| 99 | A |
| 100 | A |
| 101 | A |
| 102 | A |
| 103 | A |
| 104 | A |
| 105 | A |
| 110 | A |
| 114 | C |
| 115 | C |
| 116 | C |
| 117 | C |
| 118 | B |
| 119 | B |
| 120 | B |
| 121 | C |
| 122 | C |
| 123 | B |
| 124 | B |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 143 | A |
| 144 | A |
| 147 | B |
| 148 | B |

Tumor Growth Inhibition - In vivo PoC Studies in a Murine Xenograft Model
MATERIALS AND METHODS

| Material | Supplier |
|---|---|
| IMDM medium | Sigma |
| Foetal Bovine Serum (FBS) | Invitrogen |
| Phosphate Buffer Saline (PBS) | Invitrogen |
| Trypsin-EDTA | Invitrogen |
| Penicillin-streptomycin | Invitrogen |
| Matrigel (Cat # 354234) | Corning |
| Individually ventilated animal cages | Tecniplast, UK |
| Rodent Diet | Nutrilab Rodent Feed, India |
| 1 ml Syringe | BD- Biosciences |

Cell Line and Tumor Model:

K-562 cancer cell line sourced from American Type Culture Collection (ATCC), USA. Cells were grown in IMDM medium (Sigma, Cat #30-2005) supplemented with 10% FBS (Invitrogen, Cat #10438-026), and 1% penicillin streptomycin (Invitrogen, Cat #15140-122). To establish xenograft, the cells were harvested by trypsinization when they reach around 70 to 80% confluence and 5 million K-562 cells were suspended in 200 µL of serum-free medium and mixed at 1:1 ratio with matrigel before implanting subcutaneously into the dorsal right flank of SCID Bg mice using a 1 mL BD syringe attached to a 24-gauge needle.

Randomization

K-562 tumor grafts were measured after 10 days of cell inoculation once they became palpable. When the average tumor volume reached around 85 mm$^3$, animals were dosed after randomization into different treatment groups keeping tumor volume and number of animals in such a way so that the average tumor volume of each group remained same across the groups.

Species: Mouse (*Mus musculus*)
Strain: SCID Bg mice
Gender: Female
Source: Taconic
Total Number of Animals in Study: 30
Number of Study Groups: 05
Number of Animals per Group: 06
Body Weight at Start of Treatment: 16-18 g
Age of Animals at Start of Treatment: 7-8 weeks

STUDY DESIGN

Compounds were formulated in 0.5% CMC+0.1% Tween 80 and given for 12 consecutive days BID with 8 hour gaps. The results on tumor growth inhibition are shown below in Table 11.

TABLE 11

| Group | Treatment | % Tumor Growth Inhibition (TGI) on days | | | | |
|---|---|---|---|---|---|---|
| | | 3 | 5 | 8 | 10 | 12 |
| 2 | Cmp 126 (75 mg/kg/dose, bid., p.o.) | 41 | 32 | 27 | 27 | 36 |
| 3 | Cmp 126 (200 mg/kg/dose, bid., p.o.) | 55 | 51 | 51 | 43 | 44 |
| 4 | Cmp 133 (25 mg/kg/dose, bid., p.o.) | 43 | 37 | 48 | 45 | 43 |
| 5 | Cmp 133 (75 mg/kg/dose, bid., p.o.) | 47 | 56 | 61 | 60 | 64 |

Figure 4:
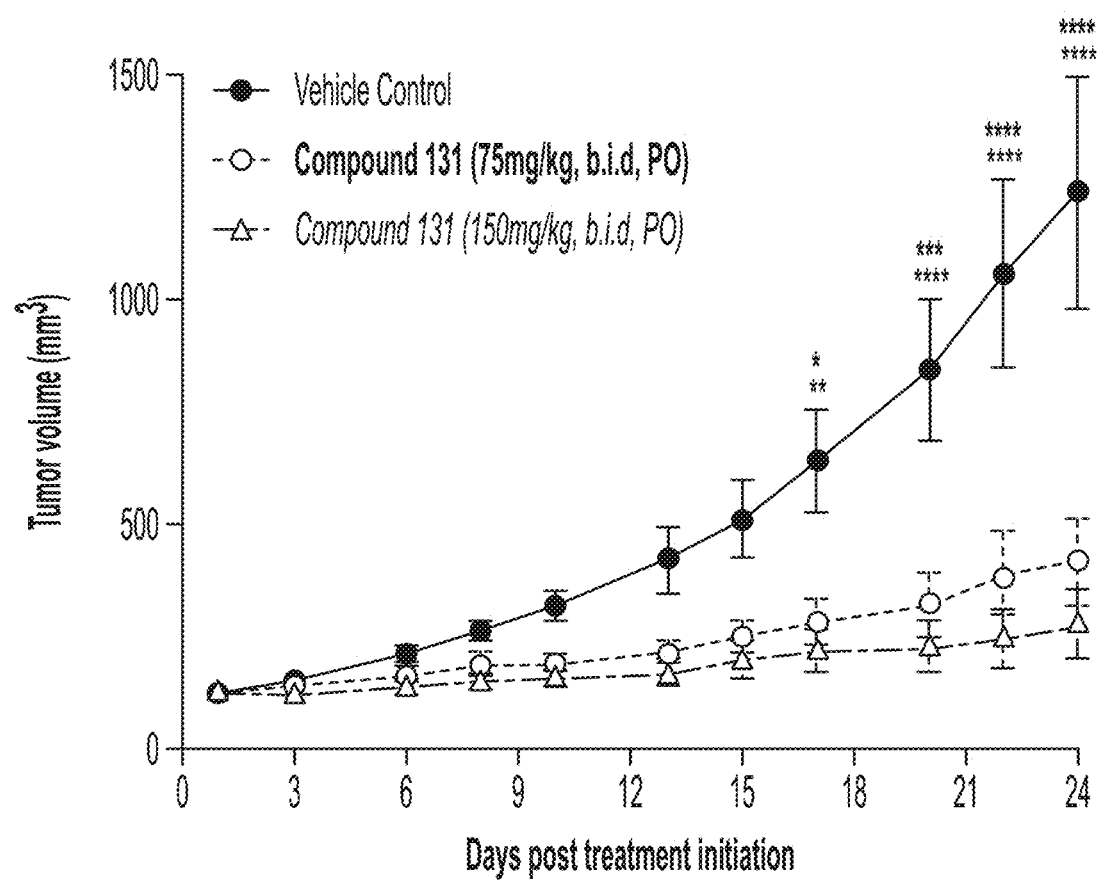
FIG. 4 illustrates the anti-tumor efficacy of Compound 131 in MV.4.11 cell (B myelomonocytic leukemia) line derived xenograft model in nude mice.

Anti-Tumor Efficacy of Compound 131 in MV.4.11 Cell (B Myelomonocytic Leukemia) Line Derived Xenograft Model in Nude Mice Nude mice were implanted with 5×10$^6$ cells MV.4.11 cells subcutaneously in the right flank region. Mice were randomized into 3 groups (8 mice each) on day 12 post cells implantation. Vehicle control was administered with formulation of test compound and treatment group was administered with compound 131 at doses 75 and 150 mg/kg orally as a suspension in 0.1% Tween-80+0.5% CMC (carboxymethyl cellulose) twice daily (b.i.d) for 24 days. Tumor measurements and body weight were recorded thrice weekly during the study period till study completion (day 24). The tumor growth inhibition for the dose groups (75 mg/kg and 150 mg/kg) were 73.6% and 86.3%, respectively. See FIG. 4.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of the Formula:

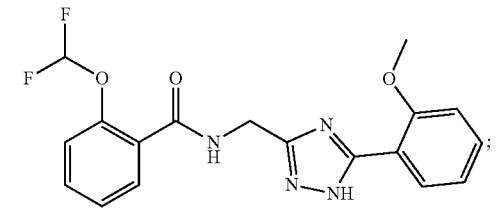 [SMILES: COc1ccccc1-c1nc(CNC(=O)c2ccccc2OC(F)F)n[nH]1]

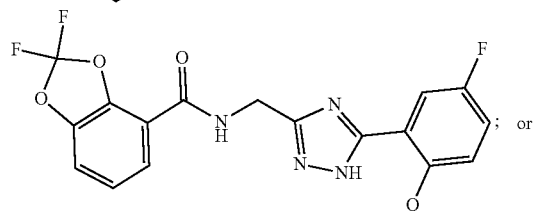 ; or

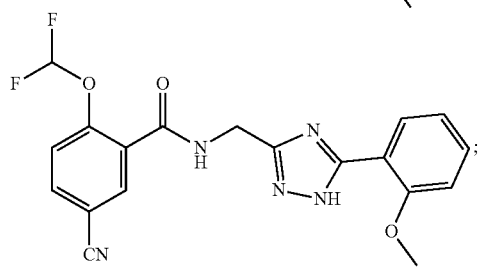

or a pharmaceutically acceptable salt of any of the foregoing.

2. The compound of claim 1, wherein the compound is of the Formula:

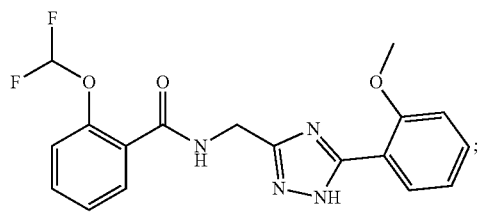

or a pharmaceutically acceptable salt thereof.

3. The compound of claim 1, wherein the compound is of the Formula:

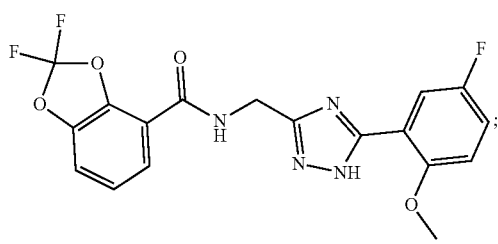 [SMILES: COc1ccc(F)cc1-c1nc(CNC(=O)c2cccc3c2OC(F)(F)O3)n[nH]1]

or a pharmaceutically acceptable salt thereof.

4. The compound of claim 1, wherein the compound is of the Formula:

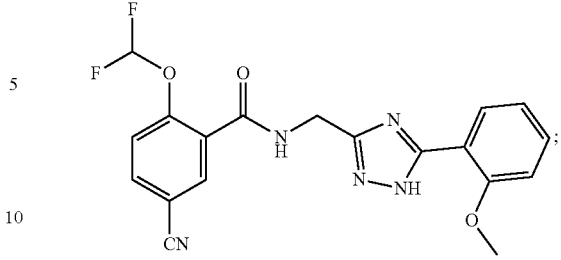

or a pharmaceutically acceptable salt thereof.

5. A pharmaceutical composition comprising a compound of the Formula:

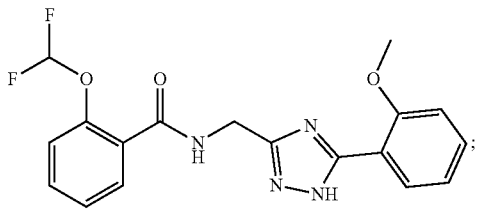

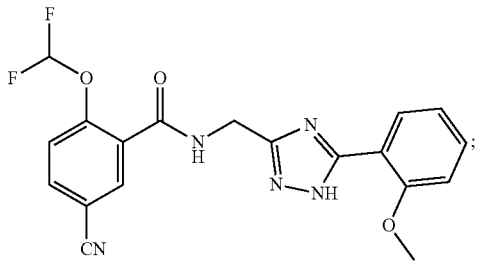 [SMILES: COc1ccccc1-c1nc(CNC(=O)c2cc(C#N)ccc2OC(F)F)n[nH]1] ; or

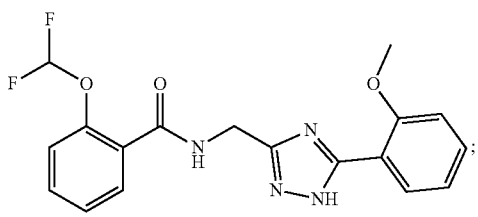 [SMILES: COc1ccccc1-c1nc(CNC(=O)c2ccccc2OC(F)F)n[nH]1]

or a pharmaceutically acceptable salt of any of the foregoing; and a pharmaceutically acceptable carrier.

6. The composition of claim 5, wherein the compound is of the Formula:

or a pharmaceutically acceptable salt thereof.

7. The composition of claim 5, wherein the compound is of the Formula:

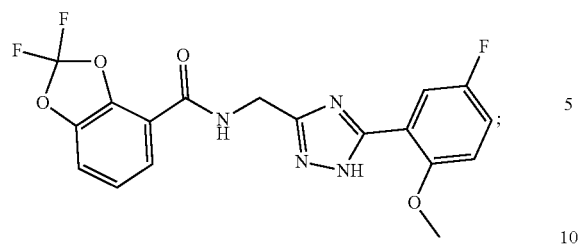
or a pharmaceutically acceptable salt thereof.
8. The composition of claim 5, wherein the compound is of the Formula:
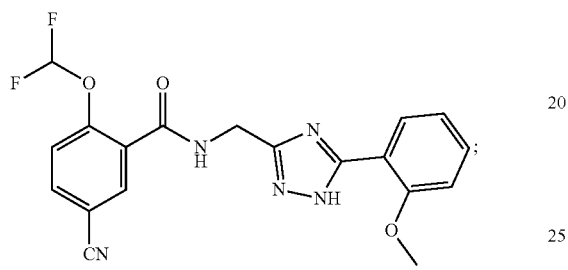
or a pharmaceutically acceptable salt thereof.
* * * * *